United States Patent
Liu et al.

(10) Patent No.: US 11,026,972 B2
(45) Date of Patent: Jun. 8, 2021

(54) METHODS FOR GENERATING MACROPHAGES WITH ENHANCED CANCER PHAGOCYTOSIS

(71) Applicant: Georgia State University Research Foundation, Inc., Atlanta, GA (US)

(72) Inventors: Yuan Liu, Decatur, GA (US); Zhen Bian, Atlanta, GA (US); Ke Zen, Decatur, GA (US)

(73) Assignee: Georgia State University Research Foundation, Inc., Atlanta, GA (US)

( * ) Notice: Subject to any disclaimer, the term of this patent is extended or adjusted under 35 U.S.C. 154(b) by 0 days.

(21) Appl. No.: 16/156,146

(22) Filed: Oct. 10, 2018

(65) Prior Publication Data

US 2019/0134089 A1 May 9, 2019

Related U.S. Application Data

(63) Continuation-in-part of application No. PCT/US2017/026821, filed on Apr. 10, 2017.

(60) Provisional application No. 62/320,588, filed on Apr. 10, 2016, provisional application No. 62/379,454, filed on Aug. 25, 2016.

(51) Int. Cl.
| | |
|---|---|
| *A61K 35/15* | (2015.01) |
| *A61K 31/739* | (2006.01) |
| *A61K 38/19* | (2006.01) |
| *A61K 45/06* | (2006.01) |
| *C07K 16/24* | (2006.01) |
| *A61K 39/395* | (2006.01) |
| *A61K 38/20* | (2006.01) |
| *A61K 31/7088* | (2006.01) |
| *A61P 35/00* | (2006.01) |
| *C07K 16/28* | (2006.01) |
| *C12N 5/0786* | (2010.01) |
| *C12N 15/113* | (2010.01) |
| *A61K 39/00* | (2006.01) |

(52) U.S. Cl.
CPC .......... *A61K 35/15* (2013.01); *A61K 31/7088* (2013.01); *A61K 31/739* (2013.01); *A61K 38/19* (2013.01); *A61K 38/191* (2013.01); *A61K 38/204* (2013.01); *A61K 38/2006* (2013.01); *A61K 39/395* (2013.01); *A61K 45/06* (2013.01); *A61P 35/00* (2018.01); *C07K 16/244* (2013.01); *C07K 16/2896* (2013.01); *C12N 5/0645* (2013.01); *C12N 15/1138* (2013.01); *A61K 2039/505* (2013.01); *C07K 2317/76* (2013.01)

(58) Field of Classification Search
CPC ...................................................... A61K 35/15
See application file for complete search history.

(56) References Cited

U.S. PATENT DOCUMENTS

| | | | |
|---|---|---|---|
| 2009/0227676 | A1 | 10/2009 | Theone |
| 2011/0070269 | A1 | 3/2011 | Wood et al. |

FOREIGN PATENT DOCUMENTS

| | | | |
|---|---|---|---|
| WO | 2009064300 | A1 | 5/2009 |
| WO | 2009131453 | A1 | 10/2009 |

OTHER PUBLICATIONS

Cooper et al, J. Immunol. (1984), 133(2), 913-922.*
Smith et al, Neurochemical Research, vol. 23, No. 3, (1998), pp. 427-434.*
Cioffi et al., Inhibition of CD47 Effectively Targets Pancreatic Cancer Stem Cells via Dual Mechanisms, Clinical Cancer Research, p. 2325-2337, 2015.
Kong et al., LPS-induced down-regulations of signal regulatory protein a contributes to innate immune activation in macrophages, The Journal of Experimental Medicine, vol. 204, No. 11, p. 2719-2731, 2001.
Murata et al., The CD47-SIRPα signalling system: its physiological roles and therapeutic application, J. Biochem., 155(6):335-344, 2104.
Search Report issued by the European Patent Office for application 17782922.3, dated Sep. 17, 2019.
International Search Report for application PCT/US2017/026821, dated Jul. 20, 2017.
Zhu et al., MicroRNA-17/20a/106a modulate macrophage inflammatory responses through targeting signal-regulatory protein α, J Allergy Clin Immunol. 132(2):426-36, 2013.

* cited by examiner

Primary Examiner — Prema M Mertz
(74) Attorney, Agent, or Firm — Thomas|Horstemeyer LLP

(57) ABSTRACT

The present invention relates to compositions and methods variously useful in treating cancer, inhibiting graft rejection, and treating autoimmune disease. The compositions and methods include those in which macrophages are conditioned to down regulate or upregulate the expression or activity of SIRPα or its interaction with CD47.

11 Claims, 51 Drawing Sheets

Specification includes a Sequence Listing.

Transferred MØ
B cells

US 11,026,972 B2

METHODS FOR GENERATING MACROPHAGES WITH ENHANCED CANCER PHAGOCYTOSIS

CROSS-REFERENCE TO RELATED APPLICATIONS

This application is a continuation-in-part of Application Serial No. PCT/US2017/026821, filed Apr. 10, 2017, which claims benefit of U.S. Provisional Application No. 62/320,588, filed Apr. 10, 2016, and U.S. Provisional Application No. 62/379,454, filed Aug. 25, 2016 which are hereby incorporated herein by reference in their entirety.

STATEMENT REGARDING FEDERALLY SPONSORED RESEARCH OR DEVELOPMENT

This invention was made with Government Support under Grant No. A1106839 awarded by the National Institutes of Health. The Government has certain rights in the invention.

SEQUENCE LISTING

This application contains a sequence listing filed in electronic form as an ASCII.txt file entitled "220702-1380 Sequence Listing_ST25" created on Oct. 9, 2018. The content of the sequence listing is incorporated herein in its entirety.

TECHNICAL FIELD

The present invention relates to compositions and methods that are variously useful in treating cancer, inhibiting graft rejection, and treating autoimmune disease, including compositions and methods that rely on at least two active agents to alter the phagocytic activity of macrophages. For example, to treat cancer, macrophages are treated or conditioned to down regulate the expression of surface signal regulatory protein α (SIRPα), to inhibit the activity of SIRPα, or to disrupt its interaction with CD47, thereby limiting the signal that would otherwise suppress phagocytic activity and allowing the macrophage to attack cancerous cells. The compositions and methods related to macrophage activation can also include distinct agents or steps that activate macrophage phagocytosis (as described further herein for, e.g., treating cancer).

SUMMARY

The present invention features, inter alia, various methods of treating a patient who has cancer, who has received, or is scheduled to receive, a cell, tissue, or organ graft, or who has an autoimmune disease. In the event of cancer, the compositions and methods enhance phagocytic activity such that cancerous cells are targeted by activated macrophages. In the event of a cell, tissue, or organ graft, or where a patient has an autoimmune disease that causes an unwanted destruction of the patient's own cells (self-cells), the compositions and methods suppress phagocytic activity such that the cells within the graft or the self-cells are not targeted for destruction by phagocytic macrophages. In the latter instance, the compositions and methods deactivate macrophages. The methods related to cancer treatment or, more generally to macrophage activation, can be carried out by administering to the patient a first agent that suppresses the expression of SIRPα, inhibits the activity of SIRPα, or disrupts the interaction between SIRPα and CD47 and a second agent that activates macrophage phagocytosis (e.g., of cancer cells). In any embodiment, the doses of the first and second agents can be doses that are therapeutically effective (i.e., that are expected to achieve a clinically beneficial outcome). Where the patient has cancer, the cancer can be a leukemia (e.g., T cell acute lymphoblastic leukemia (T-ALL), B cell acute lymphoblastic leukemia (B-ALL), or acute myeloid leukemia (AML)), a lymphoma (e.g., Hodgkins lymphoma or non-Hodgkins lymphoma), a sarcoma, a melanoma, an adenoma, a carcinoma of solid tissue (e.g., an ovarian carcinoma, breast carcinoma, pancreatic carcinoma, colon carcinoma, squamous cell carcinoma (e.g., a squamous cell carcinoma of the mouth, throat, larynx, or lung), or a transitional cell carcinoma), a hypoxic tumor, a genitourinary cancer (e.g., cervical cancer, ovarian cancer, uterine cancer, prostate cancer, penile cancer, urethral cancer, or bladder cancer), a head and neck cancer, a nervous system cancer (e.g., a glioma, an astrocytoma, or a meningioma), or a benign lesion (e.g., a papilloma).

In any of the compositions and methods described herein for enhancing the phagocytic activity of a SIRPα-expressing cell, such as a macrophage, the first agent that suppresses the expression of SIRPα can be a nucleic acid that suppresses the expression of SIRPα (e.g., a nucleic acid that mediates RNAi, an antisense oligonucleotide, a microRNA, or a targeting sequence used in conjunction with a gene editing technique such as CRISPR), a ligand for a Toll-like receptor (TLR) (e.g., lipopolysaccharide (LPS), polyinosinic:polycytidylic acid (poly I:C), lipoteichoic acid (LTA), flagellin, GARDIQUIMOD™ (an imidazoquinoline compound currently manufactured by InvivoGen; CAS number 1020412-43-4), IMIQUIMOD™ (1-isobutyl-1H-imidazo[4,5-c]quinoline-4-amine; CAS number 99011-02-6), or a CpG oligonucleotide), or a cytokine such as IFNγ, IL-1, or IL-6 (these three cytokines may advantageously be used together). Where the first agent enhances the phagocytic activity of a SIRPα-expressing cell by inhibiting the activity of SIRPα or disrupting its interaction with CD47, the first agent can be a chemical compound or an antibody (e.g., an anti-SIRPα monoclonal antibody) or other protein scaffold that suppresses the activity of SIRPα or disrupts its interaction with CD47. For example, the antibody or other protein scaffold can specifically bind a target such as SIRPα or a downstream component within a SIRPα-mediated pathway without activating the bound target. The first agent can be, for example, a soluble SIRPα extracellular domain or a fragment thereof that is engineered by molecular techniques to be the same as or different from a naturally occurring SIRPα extracellular domain. Such agents can bind but not activate CD47, thereby disrupting SIRPα's interaction with CD47.

In combination with any one or more of these types of first agents, the second agent included in a composition or administered in a method that activates macrophages can be a cytokine (e.g., an interleukin such as IL-1, IL-1β, IL-6, IL-17 (also known as IL-17A), a lipopolysaccharide (LPS), tumor necrosis factor-alpha (TNFα), or phorbol 12-myristate 13-acetate (PMA). As PMA is a PKC stimulator, it is an agent that activates macrophages by stimulating the PKC-Syk pathway. Biologically active variants of these second agents can be used as well. One or more first agents and one or more second agents can be used. In other words, the invention features compositions and methods including therapeutically effective combinations of one or more of the agents described herein as the first agent and/or one or more of the agents described herein as the second agent. As noted, the second agent, which can activate macrophages by enhancing their phagocytic activity, can be a lipopolysaccharide (LPS) or a biologically active variant thereof. Because both macrophages and some cancer cells (e.g., breast cancer cells) express TLRs, ligands for TLRs or agents that activate TLRs can be used as either a first or second agent in compositions and methods for activating macrophages and subsequently treating cancer. Thus, the second agent can also be a ligand for a Toll-like receptor (TLR) (e.g., lipopolysaccharide (LPS), polyinosinic:polycytidylic acid (poly I:C), lipoteichoic acid (LTA), flagellin, GARDIQUIMOD™ (an imidazoquinoline compound currently manufactured by InvivoGen; CAS number 1020412-43-4), IMIQUIMOD™ (1-isobutyl-1H-imidazo[4,5-c]quinoline-4-amine; CAS number 99011-02-6), or a CpG oligonucleotide).

Where the methods are directed to patients who have received, or who are scheduled to receive, a cell, tissue, or organ transplant, the steps can include administering to the patient a first agent that enhances the expression or activity of SIRPα and a second agent that deactivates macrophage phagocytosis of cells within the cell, tissue or organ transplant. The agents are administered for a time and in an amount sufficient to reduce the likelihood that the patient will reject the transplant. Thus, in any of the compositions and methods described herein for suppressing or inhibiting the phagocytic activity of a SIRPα-expressing cell, such as a macrophage, the first agent can be a nucleic acid construct that expresses SIRPα, a cytokine that increases SIRPα expression such as IL-4 or IL-10, or a compound that increases the activity of SIRPα and/or facilitates its interaction with CD47. The second agent that works to deactivate macrophage phagocytosis of, for example, transplanted cells or self-cells, can be IL-10, other IL-10 family members, such as IL-19, IL-20, IL-22, IL-24, IL-26, IL-28, IL-29, or TGFβ, or biologically active variants thereof. Due to IL-10's ability to increase SIRPα expression as well as its ability to deactivate macrophage phagocytosis, at least IL-10 can be used as either the first agent, the second agent, or the only therapeutically active agent of the compositions and methods in which it is used according to the present teaching.

In any of the present methods, the first agent and the second agent can be administered simultaneously by the same or different routes of administration or can be administered sequentially by the same or different routes of administration. Where the agents are administered simultaneously by the same route of administration, the agents may be contained within a single formulation. Accordingly, the kits of the invention may include agents (e.g., first and second agents as designated herein) within single containers or distributed between multiple containers (e.g., a vial).

Also disclosed is a method for enhancing radiation treatment in a subject with cancer, the method comprising administering to the subject to a therapeutically effective amount of a first agent that suppresses the expression of SIRPα, inhibits the activity of SIRPα, or disrupts the interaction between SIRPα and CD47; administering to the subject to a therapeutically effective amount of a second agent that activates macrophage phagocytosis; and exposing the subject to a therapeutically effective amount of radiation.

In a specific embodiment, a method of treating a patient (e.g., a patient who has cancer), according to the present invention, can be carried out by a method that includes the following steps: (a) providing a biological sample from the patient, wherein the sample comprises macrophages; (b) exposing the sample to a first agent that suppresses the expression of SIRPα, the activity of SIRPα, or the interaction between SIRPα and CD47 and a second agent that activates macrophage phagocytosis (e.g., phagocytosis of cancer cells), thereby generating activated macrophages; and (c) administering the activated macrophages to the patient. In some embodiments, the biological sample further comprises cancer cells. In some embodiments, the biological sample further comprises dendritic cells. In some embodiments, the biological sample has been enriched for myeloid cells, which include granulocytes, macrophages, and dendritic cells. This can be accomplished, for example, using CD11b and CD11c magnetic beads.

The second treatment (e.g., a treatment for cancer) can also be carried out by methods that include the following steps: (a) providing a biological sample from the patient, wherein the sample comprises macrophages that can be (or are) isolated; (b) providing a tumor sample from the same patient (e.g., a biopsy sample), from which tumor cells can be (or are) isolated; (c) exposing the sample (e.g., the biological sample comprising macrophages or macrophages isolated therefrom) to a first agent that suppresses the expression of SIRPα, the activity of SIRPα, or the interaction between SIRPα and CD47 and a second agent that activates macrophage phagocytosis (e.g., phagocytosis of cancer cells), thereby generating activated macrophages; (d) co-culturing phagocytic-activated macrophages with patient tumor cells to allow phagocytosis (i.e., under conditions and for a time sufficient to allow phagocytosis); and (e) administering the tumor cell-phagocytosed macrophages (e.g., a therapeutically effective amount of the macrophages that have phagocytosed tumor cells while in co-culture) to the patient. This treatment scheme is based on our finding that SIRPα-depleted macrophages, after phagocytosis of tumor cells, can produce anti-tumor immunity through effective antigen presentation, and hence induce anti-tumor immunity through activation of tumor-responsive T cells and B cells, which produce anti-tumor antibodies.

In another embodiment, a method of treating a patient (e.g., a patient who has cancer) can be carried out by a method that includes administering to the patient an antibody generated by a subject (whether as originally generated by the patient being treated or another patient with cancer (e.g., a cancer of the same or similar type as the cancer of the patient being treated), and in either case the antibody may be clonally reproduced and/or engineered) that (a) has a cancer of the same type as the patient to be treated; and (b) has been treated with a first agent that suppresses the expression of SIRPα, the activity of SIRPα, or the interaction between SIRPα and CD47 and a second agent that activates macrophage phagocytosis of cancer cells.

In another aspect, the present invention features various pharmaceutical compositions that can be used for treating cancer, reducing the risk of graft rejection, or treating autoimmune disease. Where the compositions are intended for a stated use (e.g., in treating a condition as described herein or for use as a medicament) and, in particular, for use in treating cancer (or for use as a medicament for treating cancer), the compositions can include at least one first agent that suppresses the expression of SIRPα (e.g., a human miRNA such as hsa-miR-17a, has-miR-20a or has-miR-106a, or a cytokine such as IFNγ, IL-1, IL-6, or a ligand for a TLR), inhibits the activity of SIRPα, or disrupts the interaction between SIRPα and CD47 and at least one second agent that activates macrophage phagocytosis (of, e.g., cancer cells). For example, the second agent can be one that stimulates the PKC-Syk pathway (e.g., or phorbol 12-myristate 13-acetate (PMA)). The second agent within a composition that activates macrophages can also be a cytokine (e.g., an interleukin such as IL-1, IL-1β, IL-6, IL-17

(also known as IL-17A), a ligand for a Toll-like receptor (TLR) (e.g., lipopolysaccharide (LPS), polyinosinic: polycytidylic acid (poly I:C), lipoteichoic acid (LTA), flagellin, GARDIQUIMOD™ (an imidazoquinoline compound currently manufactured by InvivoGen; CAS number 1020412-43-4), IMIQUIMOD™ (1-isobutyl-1H-imidazo[4,5-c]quinoline-4-amine; CAS number 99011-02-6), or a CpG oligonucleotide), tumor necrosis factor-alpha (TNFα), or biologically active variants thereof. Where the compositions are intended for use in the treatment of graft rejection or an autoimmune disease, the compositions can include at least one first agent that enhances the expression of SIRPα (e.g. IL-4 or IL-10), increases the activity of SIRPα, or facilitates the interaction between SIRPα and CD47 and at least one second agent that deactivates macrophage phagocytosis (of, e.g., a grafted cell or self-cell). For example, the second agent can be one that inhibits the PKC-Syk pathway.

In another aspect, the present invention features kits that can be used, for example, in treating cancer, treating autoimmune disease, or reducing the risk of graft rejection. Where the contents of the kit are meant to enhance macrophage phagocytic activity, the kits can include one or more of the first and second agents described herein for that purpose. For example, such a kit can include: (a) a first agent (e.g., in a first composition) that suppresses the expression of SIRPα, inhibits the activity of SIRPα, or disrupts the interaction between SIRPα and CD47; and (b) a second agent (e.g., in a second composition) that activates macrophage phagocytosis of cancer cells. In other embodiments, for example, where the contents of the kit are meant to suppress or inhibit macrophage phagocytic activity, the kits can include one or more of: (a) a first agent (e.g., in a first composition) that enhances the expression of SIRPα, promotes the activity of SIRPα, or facilitates the interaction between SIRPα and CD47; and (b) a second agent (e.g., in a second composition) that deactivates macrophage phagocytosis of grafted cells or self-cells. In any embodiment, the kits can also include instructions for use and paraphernalia for administering the compositions to a patient.

In some embodiments, the agent that deactivates macrophage phagocytosis of, for example, transplanted cells or self-cells (generally designated herein as a "second" agent) is IL-10, or an IL-10 family member including IL-19, IL-20, IL-22, IL-24, IL-26, IL-28, or IL-29, TGFβ, or biologically active variants thereof. In specific embodiments, the agent that deactivates macrophage phagocytosis of transplanted cells or self-cells can inhibit the PKC-Syk pathway.

As discussed, the present invention relies, in part, on our work with activated macrophages and their ability to directly phagocytize cells (e.g., cancer cells). Therefore, the invention may be particularly important in treating certain types of cancers where there is no anti-cancer antibody available. In certain embodiments of the invention, the compositions and methods are free from (i.e., do not include or employ) an anti-cancer antibody. As used in various embodiments of the present invention, the mechanism through which SIRPα inhibits macrophage phagocytosis can be CD47-dependent or CD47-independent. Through downregulation of SIRPα expression in macrophages, the compositions and methods described herein may overcome the CD47-SIRPα-mediated phagocytic inhibition towards cancer cells. Downregulation of SIRPα can also eliminate CD47-independent SIRPα inhibition of macrophage phagocytosis, resulting in significantly enhanced phagocytic capacity. In addition, downregulation of SIRPα expression in macrophages (and also, likely, in dendritic cells) can also enable "correct" antigen presentation and effectively induce anticancer immunity.

In another aspect, the present invention features methods of enhancing radiation treatment for cancer. These methods can include a step of treating a patient who has cancer as described herein (i.e., with one or more first and second agents that activate macrophages) or with only one or more of the "first" agents described herein as useful in activating macrophages (e.g., an agent that inhibits the expression or activity of SIRPα) and exposing the patient to a radiation therapy for the cancer. The amount of radiation to which the patient must be subjected may be reduced by the treatment with a first or first and second agent, as described herein.

Any of the methods of the invention can include a step of identifying a patient in need of treatment.

The present invention also relies, in part, on our discovery that, alternatively, certain agents can deactivate macrophages phagocytosis. Therefore, the invention may be particularly important in treating patients who have received a cell, tissue, or organ transplant or who have an autoimmune disease.

Other features and advantages of the invention will be apparent from the following detailed description, and from the claims.

DESCRIPTION OF DRAWINGS

FIG. 1A includes a schematic drawing of a wild type (WT) and targeted allele of SIRPα ("SIRPα") and data related to the generation of SIRPα "knock out" (KO) mice. PCR genotyping shows that the WT allele produces a DNA fragment of 228 bp whereas the mutated allele produces a fragment of 502 bp. Western blot (WB) analysis confirmed the depletion of SIRPα (~120 kDa) protein in bone marrow leukocytes from SIRPα$^{-/-}$ mice. FIG. 1B includes a photograph of intestinal tissue and a line graph charting the change in body weight of mice in which colitis had been induced by treatment with 1% or 2% DSS. The colitic progression in SIRPα$^{-/-}$ mice induced by 1% DSS was comparable to that in WT mice induced with 2% DSS. FIGS. 1C and 1D include data related to acute anemia and splenomegaly developed in SIRPα$^{-/-}$ mice with colitis. WT mice and SIRPα$^{-/-}$ mice treated with DSS (2% DSS for WT and 1% DSS for SIRPα$^{-/-}$) for 10 days were analyzed for the presence of peritoneal cavities (FIG. 1C) and the content of hemoglobin in peripheral blood (FIG. 1D). FIG. 1E includes a panel of photomicrographs in which hematoxylin and eosin (H&E) was used to stain sections of spleens from WT and SIRPα$^{-/-}$ mice treated with 2% and 1% DSS for 10 days. The bar graph of FIG. 1E illustrates the hemoglobin content in the spleens of WT and SIRPα$^{-/-}$ mice treated with water or DSS. FIG. 1F is a pair of line graphs showing the time course over which anemia developed in SIRPα$^{-/-}$ mice when colitis was induced with DSS and the levels of IL-17 in the serum over that same period of time. FIG. 1G is a diagram showing that IL-17 neutralization ameliorates anemia and splenomegaly in SIRPα$^{-/-}$ mice with colitis. An anti-IL-17 antibody (10 μg, i.v.) was given on days 6 and 8 (arrows) during DSS-induction of colitis. FIG. 1H is a diagram showing that IL-17-containing colitic serum induces acute anemia in SIRPα$^{-/-}$ mice. Serum samples collected from healthy (Ctl.) and colitic WT mice (2% DSS, 10 d) were administered to healthy SIRPα$^{-/-}$ mice (i.v., 3×, arrows) with or without an anti-IL-17 antibody. FIGS. 1I and 1J are illustrative graphs showing that IL-17 directly induces acute anemia and splenomegaly in SIRPα$^{-/-}$ mice and Cd47$^{-/-}$ mice. Healthy mice were given recombinant IL-17 (10 μg/kg, i.v.) on days 1 and 3 (arrows, FIG. 1J); anemia and splenomegaly were analyzed on day 5 (FIG. 1I) or in a time course manner (FIG. 1J). FIG. 1K includes diagrams showing that acute anemia and splenomegaly in SIRPα$^{-/-}$ and Cd47$^{-/-}$ mice under zymosan-peritonitis (3×, every other day), IL-6 administration (2×0 μg/kg, i.v.), LPS (0.25 mg/kg, i.p.), and CFA (1×, s.c.) administrations. Error bars are ±SEM P<0.01, *P<0.001 vs. control or the beginning time point. Data presented in each panel represent at least three independent experiments with n≥4, if applicable.

FIGS. 2A-C are illustrative graphs showing clearance of adoptively transferred CD47-positive (Cd47$^+$) or CD47-negative (Cd47$^-$) RBC in recipient mice. More specifically, FIG. 2A shows FACS analyses of CFSE-RBCs in peripheral blood at 30 min (initial time point) and 18 h after transfer. FIG. 2B shows a time course clearance of CFSE-labeled RBCs, and FIG. 2C describes the half-time ($t^{1/2}$) of RBC clearance. Error bars are ±SEM. P<0.01, *P<0.001 vs. WT mice clearance of Cd47$^+$ RBCs. FIG. 2D demonstrates RBC clearance in mice having DSS-induced colitis. Mice treated with DSS (1% for SIRPα$^{-/-}$ mice, 2% for WT and Cd47$^{-/-}$ mice) for 8 d (d8) were transfused with CFSE-RBCs followed by determination of RBC clearance after 24 h. FACS data of Cd47$^+$ RBCs and Cd47$^-$ RBCs in different mice at 30 min and 24 h after transfer were selectively shown. Total RBC phagocytosis was calculated based on the rates of CFSE-RBC clearance and the fact that SIRPα$^{-/-}$ mice eliminate both Cd47$^-$ RBC and Cd47$^+$ RBC, whereas WT mice and Cd47$^{-/-}$ mice eliminate only Cd47$^-$ RBCs. FIG. 2E shows RBC clearance in mice treated with IL-17. Mice treated once with IL-17 (10 μg/kg, i.v.) were transfused with CFSE-labeled Cd47$^+$ or Cd47$^-$ RBCs a day later. Error bars are ±SEM. P<0.01, *P<0.001 vs. control or the initial time point. Data presented in each panel represent at least three independent experiments with n≥4, if applicable.

FIGS. 3A and 3B show macrophage phagocytosis of RBCs. Freshly isolated splenic macrophages (MØ) and peritoneal macrophages (PEM) and in vitro-derived BMDM (bone marrow-derived macrophages) were tested for phagocytosis toward CFSE-labeled Cd47$^+$ or Cd47$^-$ RBCs. FIG. 3C shows that only red pulp macrophages are RBC phagocytes. FIG. 3D demonstrates activation of splenic MØ from SIRPα$^{-/-}$ and Cd47$^{-/-}$ mice for phagocytosis toward RBCs by LPS and IL-17. FIG. 3E shows activation of PEM for phagocytosis toward RBCs by LPS, IL-6, IL-1β, IL-17, and TNFα, but not IFN-γ. FIGS. 3F and 3G illustrate LPS and IL-17-activated PEM phagocytosis toward splenocytes (FIG. 3F), B16, and EL4 (FIG. 3G). Error bars are ±SEM. P<0.01, *P<0.001 vs. no treatment controls. FIG. 3H shows that thioglycollate activates PEM phagocytosis toward RBCs. PEM lavaged without (ctl.) or with Brewer thioglycollate (3%, i.p.) elicitation was tested. Error bars are ±SEM. ***P<0.001 vs. control PEM. Data presented in each panel represent at least three independent experiments with n≥4, if applicable.

FIG. 4A is a panel of illustrative line graphs showing that IL-10 inhibits macrophage phagocytosis toward "self." PEMs were treated with LPS and activating cytokines along with various concentrations of IL-10 before testing their ability to phagocytose RBCs. FIG. 4B illustrates the phagocytic plasticity of WT red pulp macrophages. The phagocytic capacity toward Cd47$^-$ RBCs displayed by freshly isolated WT splenic macrophages was lost after 2 d (d2) of in vitro culturing. Treatments of cultured macrophages with LPS and IL-17 re-elicited their phagocytosis toward RBCs. FIG. 4C shows phagocytosis of Cd47$^-$ RBCs, E. coli, zymosan, apoptotic cells, and antibody or complement-bound hRBCs. Error bars are ±SEM. ***P<0.001 vs. freshly isolated splenic macrophages. FIG. 4D includes microscopic images of RBC phagocytosis by LPS- and IL-17-treated splenic macrophages. FIG. 4E shows SIRPα ITIM phosphorylation and SHP-1 association under LPS and IL-17 treatments with or without Cd47 ligation. WT PEMs treated with LPS or IL-17 were further treated with Cd47$^+$ RBCs or Cd47-AP (10 min, 37° C.) followed by cell lysis, SIRPα immunoprecipitation, and WB detection of SIRPα phosphorylation (SIRPα$^{pY}$) and SHP-1 association. Data presented in each panel represent at least three independent experiments with n≥4, if applicable.

FIG. 5A shows the results of testing cell signaling inhibitors on LPS/cytokine-induced macrophage phagocytic activation. PEMs were treated with LPS and cytokines in the presence of various inhibitors. After washing, inhibitor-free macrophages were tested for phagocytosis toward RBCs. FIG. 5B shows that the Syk inhibitors piceatannol and R406 dose-dependently inhibited LPS-induced PEM phagocytic activation. FIG. 5C shows that Syk activity is regulated by phagocytic stimuli and IL-10. PEMs treated with LPS and activating cytokines, or together with IL-10, were tested for total Syk and phosphorylated Syk (Syk$^{pY}$, specific at Y519/520). FIG. 5D describes PMA-induced macrophages phagocytosis toward RBCs. WT and SIRPα$^{-/-}$ PEMs were treated with PMA (37° C., 30 min) before testing phagocytosis toward RBCs. FIG. 5E is a schematic depiction of PKC-Syk-mediated macrophage phagocytic activation toward self. FIG. 5F shows that Syk is downstream of PKC. Left: Inhibition of Syk by piceatannol and R406 prevented PMA-induced phagocytic activation. Right: PMA treatment failed to rescue LPS-mediated phagocytic activation-suppressed by Syk inhibition. Error bars are ±SEM. *P<0.001 vs. the respective controls. FIG. 5G shows inhibition of SHP by pervanadate eliminates Cd47-dependent phagocytic recognition. LPS-treated WT PEMs were further briefly treated with pervanadate before testing for phagocytosis toward RBCs. Error bars are ±SEM. *P<0.001 vs. the respective controls. FIG. 5H shows that PMA treatment does not affect SIRPα expression or Cd47 ligation-induced SIRPα phosphorylation and SHP-1 association. Data presented in each panel represent at least three independent experiments with n≥4, if applicable.

FIG. 6A shows that blocking CRT or LRP1 failed to inhibit LPS/cytokine-induced PEM phagocytosis toward RBCs. LPS/cytokine-activated PEM phagocytosis toward RBCs was tested in the presence of anti-CRT antibody 1 (Abcam) and 2 (CST) (10 μg/mL each), anti-LRP1 (20 μg/mL), and the LRP1 receptor-associated protein (RAP; 20 μg/mL), all dialyzed free of sodium azide (note: sodium azide potently inhibits phagocytosis toward self-cells even at low concentrations). FIG. 6B shows that CRT-LRP1 controls macrophage phagocytosis toward apoptotic cells. PEM (unstimulated) phagocytosis toward apoptotic B16 cells was tested in the presence of same antibodies and RAP as in A. Error bars are ±SEM. *P<0.001 vs. phagocytosis in the presence of control IgG. FIG. 6C shows that macrophage cell surface CRT or LRP1. PEMs, with or without (ctl.) treatment with LPS, IL-17, IL-6, or PMA, were labeled for cell surface LRP1 and CRT followed by FACS. Increased and decreased expressions were marked by arrows. FIG. 6D shows results of our exploration of other phagocytic receptors. Activated PEM phagocytosis toward RBCs was tested in the presence of antibodies against SR-A, Fc receptor Cd16/32 (10 µg/mL of each), inhibitors against SR-B (BLT1, 5 µM), dectin (laminarin, 100 µg/mL), complement (heparin, 40 U/mL), and antibody against Cd11b (10 µg/mL). Error bars are ±SEM. *P<0.001 vs. the respective control without inhibition. Data presented in each panel represent at least three independent experiments with n≥4, if applicable.

FIGS. 7A-C show that monocytes/macrophages (2×10$^7$) derived from bone marrow cells of WT or SIRPα$^{-/-}$ mice were labeled with CMTMR and transferred into three strains of recipient mice. More specifically, FIG. 7A shows that only SIRPα$^{-/-}$ macrophages in WT mice displayed phagocytosis toward RBCs, resulting in anemia and splenomegaly. Error bars are ±SEM. *P<0.05, P<0.01 vs. control 960 by transferring WT monocytes/macrophages into WT mice. FIG. 7B shows that cotransfer of CFSE-labeled Cd47$^+$ RBCs along with SIRPα$^{-/-}$ monocyte/macrophages into WT mice confirmed rapid RBC clearance. Error bars are ±SEM. *P<0.001 vs. the initial time point. FIG. 7C shows distribution of CMTMR-labeled SIRPα$^{-/-}$ macrophages in spleen red pulp (RP) but not white pulp (WP). FIG. 7D shows that higher levels of IL-10 and lesser IL-17 produced by spleen cells and in serum from SIRPα$^{-/-}$ and Cd47$^{-/-}$ mice. FIG. 7E shows decreases in Cd11c$^+$Cd8$^-$ DC and Cd4$^+$ helper (Th) lymphocytes in the spleen of SIRPα$^{-/-}$ and Cd47$^{-/-}$ mice. FIG. 7F shows transcription profiling of red pulp macrophages from WT and SIRPα$^{-/-}$ mice. F4/80$^+$ red pulp macrophages were affinity isolated before mRNA isolation and profiling. The red-colored molecules (most being activating) are expressed at higher levels in WT than in SIRPα$^{-/-}$ red pulp macrophages, whereas the blue-colored molecules (most being suppressive) are expressed oppositely. FIG. 7G shows reduction of CD11c$^+$CD8$^-$ DCs in the spleens of MyD88$^{-/-}$ mice and germ-free (GF)-conditioned mice. FIG. 7H shows attenuated clearance of CD47$^-$ RBC in MyD88$^{-/-}$ mice and GF mice. Data presented in each panel represent at least three independent experiments with n≥4, if applicable.

FIG. 8A shows the experimental scheme; FIG. 8B shows tumor volumes before & after irradiation and animal survival rates.

DETAILED DESCRIPTION

Figure 1A:
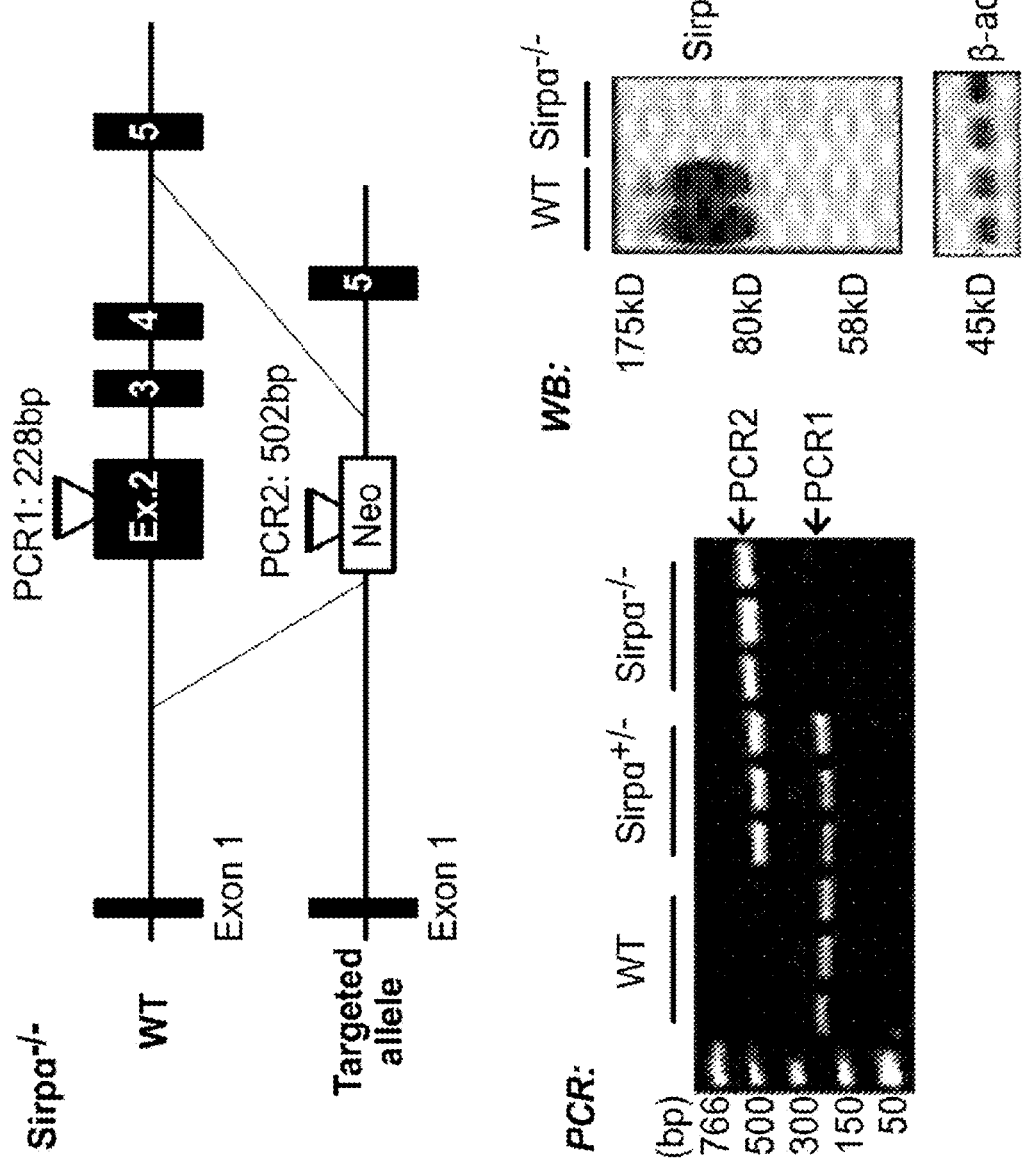
FIGS. 1A-1K illustrate our assessment of acute anemia in mice deficient of CD47-SIRPα-mediated inhibition under inflammatory conditions.

Macrophage phagocytosis of cancer cells is regarded as a promising and powerful way to eradicate cancer. Previous studies have suggested that macrophage surface signal regulatory protein α (SIRPα; van den Berg et al., *J. Immunol.*, 175 (12):7788-7789, 2005) interacting with the broadly-expressed cellular receptor CD47 plays a crucial role in controlling macrophage phagocytosis (Oldenborg et al., *Science*, 288 (5473):2051-2054, 2000; Matozaki et al., *Trends in Cell Biology* 2009, 19 (2):72-80, 2009; Barclay et al., *Current Opinion in Immunology*, 21 (1):47-52, 2009; Chao et al., *Current Opinion in Immunology*, 24 (2):225-232, 2012). Between these two proteins, CD47 acts as a marker of "self"; through the extracellular interaction with SIRPα, CD47 protects host tissue cells from being phagocytized by macrophages. SIRPα, an inhibitory regulator expressed on myeloid leukocytes (Seiffert et al., Blood, 94 (11):3633-3643, 1999; Matozaki et al., Trends Cell Biol., 19 (2):72-80, 2009; Barclay et al., Nat. Rev. Immunol., 6 (6):457-464, 2006), delivers key signaling events through the cytoplasmic domain that contains two immunoreceptor tyrosine-based inhibition motifs (ITIMs; Kharitonenkov et al., Nature, 386:181-186, 1997). It has been suggested that, upon CD47 extracellular binding, SIRPα alters tyrosine phosphorylation in the intracellular ITIMs, which subsequently recruit SH2-containing tyrosine phosphatase (SHP1/2) and initiate inhibitory signaling events that suppress macrophage phagocytosis. Conversely, deficiency of CD47 on potential target cells, or absence of SIRPα or its ITIM domain on macrophages, promotes macrophage phagocytosis. Experiments supporting this CD47-SIRPα mechanism were first reported by Oldenborg et al. (Science, 288 (5473): 2051-2054, 2000), who showed that adoptive transfer of CD47$^{-/-}$ RBC derived from CD47 deficient mice into congenic wild-type (WT) recipients results in rapid clearance in the spleen by red pulp macrophages without facilitation by antibodies or complement opsonization. Decreases in SIRPα ITIM phosphorylation were observed to correlate with the fast removal of the donor CD47$^{-/-}$ RBC. Similar results were also shown by others (Blazar et al., J. Exp. Med., 194 (4):541-549, 2001; Yamao et al., J. Biol. Chem., 277 (42):39833-39839, 2002), confirming that the absence of CD47 on target cells alone is sufficient to trigger WT macrophages to phagocytize those CD47-deficient target cells. The importance of CD47/SIRPα mechanism is underlined in cancer research in which upregulation of CD47 expression on tumor cells is considered to be associated with cancer establishment in vivo and evasion of immunological clearance (Chao et al., Current Opinion in Immunology, 24 (2):225-232, 2012), whereas perturbation of CD47-SIRPα interaction provides opportunities for macrophage-mediated cancer eradication (Chao et al., Cancer Res., 71 (4):1374-1384, 2011; Zhao et al., Proc. Natl. Acad. Sci. USA, 108 (45):18342-18347, 2011). In addition, the mechanism of CD47/SIRPα-controlled macrophage phagocytosis has also been implicated in xenotransplantation in which donor tissues often lack compatible CD47 to ligate macrophage SIRPα in recipients. Expression of human CD47 on porcine cells has been shown to improve the human macrophage tolerance (Del Rio et al., Xenotransplantation, 20 (6):397-406, 2013; Ide et al., Proc. Natl. Acad. Sci., 104 (12):5062-5066, 2007; Maeda et al., Transpl. Immunol., 29 (1-4):76-81, 2013; Wang et al., Blood, 109 (2):836-842, 2007).

While the above studies are promising, some experimental observations suggest that the mechanism by which CD47/SIRPα controls macrophage phagocytosis requires further investigation. In particular, mice lacking CD47 (CD47$^{-/-}$) or SIRPα (SIRPα$^{-/-}$, established in the current study (see below)) are relatively healthy, without manifesting macrophage phagocytosis-mediated tissue destruction. Similarly, the mice in which the SIRPα intracellular signaling domain was deleted (Tomizawa et al., *The Journal of Immunology*, 179 (2):869-877, 2007) are also generally healthy; only one study reported mild anemia at advanced ages possibly attributable to enhanced macrophage phagocytosis (Ishikawa-Sekigami et al., *Blood*, 107 (1):341-348, 2006). Since macrophages in these mice lack CD47/SIRPα-mediated suppression, the CD47-SIRPα mechanism alone provides no explanation for how and when macrophages are triggered to attack self-cells, nor does it describe how this phagocytic process is carried out. Thus, at least one other mechanism must exist restraining macrophages from attacking self-cells.

This invention is partially based on our work showing that, during inflammatory conditions, interaction between CD47 and SIRPα prevents macrophage phagocytosis of self-cells. Accordingly, disrupting this interaction can allow certain factors (inflammatory factors) to activate macrophage phagocytosis of self-cells. The invention is also based on our demonstration of conditions enabling a robust activation of macrophage phagocytosis that completely eliminates pulmonary metastatic B16 melanoma in SIRPα$^{-/-}$ mice. Transferring the anti-cancer immunity induced following SIRPα$^{-/-}$ macrophage phagocytosis effectively suppressed B16 melanoma in WT mice. Accordingly, in addition to administering first and second agents to patients, as described herein, the invention also features methods in which a sample or samples from the same patient, containing macrophages and cancer cells, are placed in culture under conditions permitting the macrophages to phagocytose the cancer cells with or without the benefit of any of the first and/or second agents described herein, after which the macrophages are "re-administered" to the patient from whom they were obtained.

The invention is also partially based on our discovery that, in addition to the CD47/SIRPα mechanism, macrophage phagocytosis of self-cells is partially controlled by activation of the cytokine-stimulated protein kinase C (PKC)-Syk pathway. In the CD47/SIRPα mechanism, the interaction between CD47 and SIRPα may trigger inhibitory signaling through SIRPα cytoplasmic immunoreceptor tyrosine-based inhibition motifs and tyrosine phosphatase SHP-1/2. Thus, the PKC-Syk pathway may activate one or more receptors that the CD47-SIRPα triggered SHP activity inhibits.

Our strategy of using activated macrophages to directly phagocytize cancer cells is especially advantageous when there is no cancer-specific therapeutic antibody available, since macrophages generally would not phagocytose live cancer cells that normally have high levels of CD47 expression on the cell surface. In addition, if there is a humanized antibody against the cancer available, macrophage phagocytosis of the cancer cells can also be enhanced by down regulation of SIRP☐ and/or activation of phagocytosis using the first and second agents described herein. In the presence of antibody, macrophage phagocytosis can be initiated by the Fc-mediated mechanism provided the CD47-SIRPα-mediated inhibition is removed. The invention can use an antibody or a competitive peptide to block CD47-SIRPα interaction. Our invention also provides a new strategy for direct down-regulation of SIRPα expression on macrophages. Reduction of SIRPα not only removes the CD47-dependent phagocytic inhibition but also CD47-independent phagocytic inhibition of macrophages, resulting in remarkably enhanced phagocytic capacity.

As described further herein, we have developed methods of treating a patient who has cancer. The compositions administered to the patient include a first agent that suppresses the expression or activity of SIRPα or the interaction between SIRPα and CD47. In some embodiments, the composition can further include, or be administered with (simultaneously or sequentially by the same or different routes of administration), a second agent that activates macrophage phagocytosis of cancer cells.

Any agent described herein, whether referred to as a first agent, a second agent, or a biologically active variant of the first or second agent and regardless of its intended use, can be a small molecule (i.e., an organic molecule having a molecular weight of about 1000 Da or less), an amino acid, a peptide, a nucleic acid (e.g., RNAs or DNAs whether single- or double-stranded and whether contained in or free from an expression vector), a protein (e.g., an antibody or other protein scaffold), a peptidomimetic, a non-peptide oligomer, or any combination of one or more of these types of agents. Peptides and proteins are both polymers of amino acid residues; we may use the term "peptide" to refer to a short polymer (e.g., a trimer) or to a fragment of a full-length, naturally occurring protein. The first agent or the second agent, regardless of its intended use, can be wholly naturally occurring (and may be formulated or used such that it acquires a markedly different characteristic), derived from a naturally existing agent (i.e., it may be a part of a hybrid or chimeric molecule having one or more naturally occurring component parts), or non-naturally occurring (i.e., distinct from any known, naturally occurring counterpart with, preferably a modification that gives rise to a markedly different characteristic). For example, the agent can be a nucleic acid that mediates an RNAi, an antisense oligonucleotide, a nucleic acid that initiates a gene editing program (e.g., a nucleic acid that reduces gene expression using the CRISPR or CRISPR/cas9 system), or a microRNA, any of which can be contained within or encoded by an expression vector (e.g., a plasmid or viral vector). The first or second agents can also be antibodies (e.g., an anti-SIRPα antibody (e.g., an anti-SIRPα monoclonal antibody).

As noted, a first agent that suppresses the expression or activity of SIRPα and/or inhibits the interaction between SIRPα and CD47 is useful in macrophage activation and, more specifically, cancer treatment. In some embodiments, the first agent, perhaps by disrupting the interaction between SIRPα and CD47 can be an engineered SIRPα variant as described by Weiskopf et al. (Science, 2013 341 (6141):88-91). These high-affinity SIRPα variants demonstrate about a 50,000-fold increased affinity for human CD47 relative to wild-type SIRPα.

In any of the compositions and methods described herein for enhancing the phagocytic activity of a SIRPα-expressing cell, such as a macrophage, the first agent that suppresses the expression of SIRPα can be a nucleic acid that suppresses the expression of SIRPα (e.g., a nucleic acid that mediates RNAi, an antisense oligonucleotide, a microRNA, or a targeting sequence used in conjunction with a gene editing technique such as CRISPR), a ligand for a Toll-like receptor (TLR) (e.g., lipopolysaccharide (LPS), polyinosinic: polycytidylic acid (poly I:C), lipoteichoic acid (LTA), flagellin, GARDIQUIMOD™ (an imidazoquinoline compound currently manufactured by InvivoGen; CAS number 1020412-43-4), IMIQUIMOD™ (1-isobutyl-1H-imidazo[4, 5-c]quinoline-4-amine; CAS number 99011-02-6), or a CpG oligonucleotide), or a cytokine such as IFNγ, IL-1, or IL-6.

Exemplary and useful RNA molecules useful as the first agent include the miRNAs designated hsa-miR-17a, has-miR-20a and has-miR-106a in J. Allergy Clin. Immunol. 132 (2):426-436, 2013).

The sense strand of miR-17 is 5'-CAAAGUGCUUA-CAGUGCAGGUAG-3' (SEQ ID NO:1); the sense strand of miR-20a is 5;-UAAAGUGCUUAUAGUGCAGGUAG-3' (SEQ ID NO:2); the sense strand of miR-106a-5p is 5'-AAAAGUGCUUACAGUGCAGGUAG-3' (SEQ ID NO:3); the antisense strand of miR-17 is 5'-CUACCUGCA-CUGUAAGCACUUUG-3' (SEQ ID NO:4); the antisense strand of miR-20a is 5'-CUACCUGCACUAUAAGCAC-UUUA-3' (SEQ ID NO:5), and the antisense strand of miR-106a is 5'-CUACCUGCACUGUAAGCACUUUU-3' (SEQ ID NO:6).

Where the first agent enhances the phagocytic activity of a SIRPα-expressing cell by inhibiting the activity of SIRPα or disrupting its interaction with CD47, the first agent can be a chemical compound or an antibody (e.g., an anti-SIRPα monoclonal antibody) or other protein scaffold that suppresses the activity of SIRPα or disrupts its interaction with CD47. For example, the antibody or other protein scaffold can specifically bind a target such as SIRPα or a downstream component within a SIRPα-mediated pathway without activating the bound target. The first agent can be, for example, a soluble SIRPα extracellular domain or a fragment thereof that is engineered by molecular techniques to be the same as or different from a naturally occurring SIRPα extracellular domain. Such agents can bind but not activate CD47, thereby disrupting SIRPα's interaction with CD47.

SIRPα can also be inhibited by inhibiting the SIRPα signaling pathway. We have conducted studies showing that several tyrosine kinase inhibitors (e.g. those targeting a Src family tyrosine kinase and/or Btk) inhibit SIRPα cytoplasmic domain phosphorylation and recruitment of SHP-1/2. Accordingly, these agents are useful in the present methods.

In combination with any one or more of these types of first agents, the second agent included a composition or administered in a method that activates macrophages can be a cytokine (e.g., an interleukin such as IL-1, IL-1β, IL-6, IL-17 (also known as IL-17A), a lipopolysaccharide (LPS), tumor necrosis factor-alpha (TNFα), or phorbol 12-myristate 13-acetate (PMA). As PMA is a PKC stimulator, it is an agent that activates macrophages by stimulating the PKC-Syk pathway. Biologically active variants of these second agents can be used as well. One or more first agents and one or more second agents can be used. In other words, the invention features compositions and methods including therapeutically effective combinations of one or more of the agents described herein as the first agent and/or one or more of the agents described herein as the second agent. As noted, the second agent, which can activate macrophages by enhancing their phagocytic activity, can be a lipopolysaccharide (LPS) or a biologically active variant thereof. Because both macrophages and some cancer cells (e.g., breast cancer cells) express TLRs, ligands for TLRs or agents that activate TLRs can be used as either a first or second agent in compositions and methods for activating macrophages and subsequently treating cancer. Thus, the second agent can also be a ligand for a Toll-like receptor (TLR) (e.g., lipopolysaccharide (LPS), polyinosinic: polycytidylic acid (poly I:C), lipoteichoic acid (LTA), flagellin, GARDIQUIMOD™ (an imidazoquinoline compound currently manufactured by InvivoGen; CAS number 1020412-43-4), IMIQUIMOD™ (1-isobutyl-1H-imidazo[4, 5-c]quinoline-4-amine; CAS number 99011-02-6), or a CpG oligonucleotide).

In some embodiments, the first agent or the second agent that activates macrophages, perhaps by disrupting the interaction between SIRPα and CD47 can be Surfactant Protein (e.g., Surfactant Protein A, B or D).

Kits: As another aspect of the invention, we have developed kits that package together at least one of the agents described herein and instructions for use. We may refer to the kits as "pharmaceutical kits" as they are intended for use in the treatments described herein (e.g., for treating cancer, inhibiting graft rejection, or treating an autoimmune disease). The kits can include ready-to-use compositions or stock solutions thereof that include one or more of the first and second agents described herein. The ready-to-use compositions can be aliquoted in dosage units such that each aliquot contains a therapeutically effective amount of a single dose for a patient, and the stock solutions can include a dosage unit that, upon reconstitution or dilution, similarly contains a therapeutically effective amount of a single dose for a patient. The first and second agents can be mixed together in a single container or contained within separate containers, allowing them to be mixed in varying amounts prior to administration or administered sequentially or via separate routes of administration. In any embodiment, the kit can include instructions for use and, optionally, paraphernalia such as a needle, syringe, tubing, additional vials for diluting one or more of the agents included therein, the diluents, compositions for sterilizing a site of injection, gloves, and the like. The instructions can be printed (e.g., as a conventional product insert or label) or can be an audio or visual medium or link to a website or other information resource.

Methods of Treatment: In a different respect of the invention, we have developed another method of treating a patient who has cancer. To practice the method, one can obtain a biological sample from the patient that includes macrophages. The method can further include exposing the sample to a first agent that suppresses the expression or activity of SIRPα or the interaction between SIRPα and CD47 and a second agent that activates macrophage phagocytosis of cells (e.g., cancer cells), thereby generating activated macrophages. One then can administer the activated macrophages to the patient.

To practice any of the present methods of treating cancer, one can also administer to the patient an antibody generated by a subject who has a cancer of the same type as the patient to be treated.

As another aspect of the invention, we have developed a method of treating a patient to reduce the risk of transplant tissue rejection. To practice the method, one can administer to the patient an agent that deactivates macrophage phagocytosis of transplanted tissue cells. In some embodiments, one can further administer to the patient an agent that enhances the expression or activity of SIRPα or the interaction between SIRPα and CD47.

As another aspect of the invention, we have developed a method of treating a patient who has an autoimmune disease. To practice the method, one can administer to the patient an agent that deactivates macrophage phagocytosis of self-cells. In certain embodiments, one can further administer to the patient an agent that enhances the expression or activity of SIRPα or the interaction between SIRPα and CD47.

Although the invention was developed with human subjects in mind, it is not so limited. The present methods can be carried out for the benefit of any vertebrate animal, including a mammal or avian. In some embodiments, the patient can be a human or another mammal. The patient can also be a domesticated animal (e.g., a dog or cat). The patient can also be an animal kept as livestock (e.g., cattle, sheep, chickens, horses, pigs, or goats).

One or more of the first and second agents described herein can also be brought into contact with a cell, tissue, organ, organ system, or a medium containing one or more of these biological agents ex vivo. Thus, the methods can be carried out with a "subject" that is less than an intact organism (e.g., a human being).

Various types of cancers can be treated by the methods described herein. For example, the cancer can be adrenal cancer, anal cancer, bile duct cancer, bladder cancer, bone cancer, brain cancer, breast cancer, Castleman disease, cervical cancer, colon/rectum cancer, endometrial cancer, esophageal cancer, eye cancer, gallbladder cancer, gastrointestinal carcinoid tumors, gastrointestinal stromal tumor (gist), gestational trophoblastic disease, Hodgkin disease, Kaposi sarcoma, kidney cancer, laryngeal and hypopharyngeal cancer, leukemia, liver cancer, lung cancer, lymphoma, malignant mesothelioma, multiple myeloma, myelodysplastic syndrome, nasal cavity and paranasal sinus cancer, nasopharyngeal cancer, neuroblastoma, non-Hodgkin lymphoma, oral cavity and oropharyngeal cancer, osteosarcoma, ovarian cancer, pancreatic cancer, penile cancer, pituitary tumors, prostate cancer, retinoblastoma, rhabdomyosarcoma, salivary gland cancer, sarcoma, skin cancer, small intestine cancer, stomach cancer, testicular cancer, thymus cancer, thyroid cancer, uterine sarcoma, vaginal cancer, vulvar cancer, Waldenstrom macroglobulinemia, Wilms tumor, melanoma, adenoma, carcinoma of solid tissue, hypoxic tumor, genitourinary cancer, head and neck cancer, nervous system cancer, benign lesion, or any combination thereof.

The autoimmune disease treated by the method according to the invention may be associated with various diseases, such as acute disseminated encephalomyelitis (ADEM), acute necrotizing hemorrhagic leukoencephalitis, Addison's disease, agammaglobulinemia, alopecia areata, amyloidosis, ankylosing spondylitis, anti-gbm/anti-tbm nephritis, antiphospholipid syndrome (APS), autoimmune angioedema, autoimmune aplastic anemia, autoimmune dysautonomia, autoimmune hepatitis, autoimmune hyperlipidemia, autoimmune immunodeficiency, autoimmune inner ear disease (AIED), autoimmune myocarditis, autoimmune oophoritis, autoimmune pancreatitis, autoimmune retinopathy, autoimmune thrombocytopenic purpura (ATP), autoimmune thyroid disease, autoimmune urticaria, axonal and neuronal neuropathies, Balo disease, Behcet's disease, bullous pemphigoid, cardiomyopathy, Castleman disease, celiac disease, Chagas disease, chronic fatigue syndrome, chronic inflammatory demyelinating polyneuropathy (CIDP), chronic recurrent multifocal osteomyelitis (CRMO), Churg-Strauss syndrome, cicatricial pemphigoid/benign mucosal pemphigoid, Crohn's disease, Cogans syndrome, cold agglutinin disease, congenital heart block, coxsackie myocarditis, crest disease, essential mixed cryoglobulinemia, demyelinating neuropathies, dermatitis herpetiformis, dermatomyositis, Devic's disease (neuromyelitis optica), discoid lupus, Dressler's syndrome, endometriosis, eosinophilic esophagitis, eosinophilic fasciitis, erythema nodosum, experimental allergic encephalomyelitis, Evans syndrome, fibromyalgia, fibrosing alveolitis, giant cell arteritis (temporal arteritis), giant cell myocarditis, glomerulonephritis, Goodpasture's syndrome, granulomatosis with polyangiitis (gpa) (formerly called Wegener's granulomatosis), Graves' disease, Guillain-Barre syndrome, Hashimoto's encephalitis, Hashimoto's thyroiditis, hemolytic anemia, Henoch-Schonlein purpura, herpes gestationis, hypogammaglobulinemia, idiopathic thrombocytopenic purpura (ITP), IgA nephropathy, IgG4-related sclerosing disease, immunoregulatory lipoproteins, inclusion body myositis, interstitial cystitis, juvenile arthritis, juvenile diabetes (type 1 diabetes), juvenile myositis, Kawasaki syndrome, Lambert-Eaton syndrome, leukocytoclastic vasculitis, lichen planus, lichen sclerosus, ligneous conjunctivitis, linear, IgA disease (LAD), lupus (SLE), Lyme disease, Meniere's disease, microscopic polyangiitis, mixed connective tissue disease (mctd), Mooren's ulcer, Mucha-habermann disease, multiple sclerosis, myasthenia gravis, myositis, narcolepsy, neuromyelitis optica (Devic's), neutropenia, ocular cicatricial pemphigoid, optic neuritis, palindromic rheumatism, pandas (pediatric autoimmune neuropsychiatric disorders associated with $Streptococcus$), paraneoplastic cerebellar degeneration, paroxysmal nocturnal hemoglobinuria (pnh), Parry-Romberg Syndrome, Parsonnage-Turner Syndrome, pars planitis (peripheral uveitis), pemphigus, peripheral neuropathy, perivenous encephalomyelitis, pernicious anemia, Poems syndrome, polyarteritis nodosa, Type I, II, and III autoimmune polyglandular syndromes, polymyalgia rheumatic, polymyositis, postmyocardial infarction syndrome, postpericardiotomy syndrome, progesterone dermatitis, primary biliary cirrhosis, primary sclerosing cholangitis, psoriasis, psoriatic arthritis, idiopathic pulmonary fibrosis, pyoderma gangrenosum, pure red cell aplasia, Raynauds phenomenon, reactive arthritis, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm and testicular autoimmunity, stiff person syndrome, subacute bacterial endocarditis (SBE), Susac's Syndrome, sympathetic ophthalmia, Takayasu's arteritis, temporal arteritis/giant cell arteritis, thrombocytopenic purpura (TTP), tolosa-hunt syndrome, transverse myelitis, Type 1 diabetes, ulcerative colitis, undifferentiated connective tissue disease (UCTD), uveitis, vasculitis, vesiculobullous dermatosis, vitiligo, Wegener's granulomatosis (now termed granulomatosis with polyangiitis (GPA)).

The second agent that activates macrophage phagocytosis of cancer cells can be a small molecule, an amino acid, a peptide, a nucleic acid (e.g., RNAs or DNAs), a protein (e.g., an antibody) or a combination of one or more thereof. The second agent can be naturally occurring, derived from a naturally existing agent, or synthesized. In some embodiments, the second agent activates the PKC-Syk pathway in the subject. For example, the second agent can be a cytokine (e.g., IL-17, IL-1β, IFNγ, IL-6, or a biologically active variant thereof). The second agent can also be a lipopolysaccharide (LPS) or a biologically active variant thereof. In some embodiments, the second agent can be IL-1, TNFα, PMA (phorbol 12-myristate 13-acetate), or a biologically active variant thereof. In certain embodiments, the invention can include a step of identifying an agent that activates macrophage phagocytosis of cancer cells.

The agent that enhances the expression or activity of SIRPα or the interaction between SIRPα and CD47 can be a small molecule, an amino acid, a peptide, a nucleic acid (e.g., an RNA or DNA), a protein (e.g., an antibody or other protein scaffold) or a combination of one or more thereof. The agent can be naturally occurring, derived from a naturally existing agent, or non-naturally occurring. For example, the agent can be a nucleic acid that expresses SIRPα or a biologically active variant thereof that interacts with CD47.

In some embodiments, the invention can include a step of identifying an agent that enhances the expression or activity of SIRPα or the interaction between SIRPα and CD47.

The agent that deactivates macrophage phagocytosis of self-cells or graft tissue can be a small molecule, an amino acid, a peptide, a nucleic acid (e.g., RNAs or DNAs), a protein (e.g., antibodies) or a combination of one or more thereof. The agent can be naturally occurring, derived from a naturally existing agent, or synthesized. The agent can deactivate one or more types of macrophage (e.g., M1 microphage). In some embodiments, the agent can be a cytokine (e.g., interleukin), preferably, a cytokine in the IL-10 family, such as IL-10, IL-19, IL-20, IL-22, IL-24, IL-26, IL-28, IL-29, or a biologically active variant thereof. In some embodiments, the agent inhibits one or more pathways (e.g., the PKC-Syk pathway) in the subject.

In certain embodiments, the invention can include a step of identifying an agent that deactivates macrophage phagocytosis of self-cells or graft tissue.

In some embodiments, the small molecule(s) can be but is/are not limited to pharmaceutical agents or drugs. For example, the small molecule can be an alkaloid, glycoside, lipid, non-ribosomal peptide (e.g., actinomycin-D), phenazine, natural phenol (e.g., a flavonoid), polyketide, terpene (e.g., a steroid), tetrapyrrole, or other metabolite.

In some embodiments, the peptides can include isoleucine-proline-proline (IPP), valine-proline-proline (VPP)), ribosomal peptides, nonribosomal peptides, peptones, and peptide fragments. The peptides can also include tachykinin peptides (e.g., substance P, kassinin, neurokinin A, eledoisin, neurokinin B), vasoactive intestinal peptides (e.g., vasoactive intestinal peptide (VIP), pituitary adenylate cyclase activating peptide (PACAP), peptide histidine isoleucine 27 (Peptide PHI 27), growth hormone releasing hormone 1-24 (GHRH 1-24), glucagon, secretin), pancreatic polypeptide-related peptides (e.g., neuropeptide Y (NPY), peptide YY (PYY), avian pancreatic polypeptide (APP), pancreatic polypeptide (PPY)), opioid peptides (e.g., proopiomelanocortin (POMC) peptides, enkephalin pentapeptides, prodynorphin peptides), calcitonin peptides (e.g., calcitonin, amylin, AGG01), and other peptides (e.g., B-type natriuretic peptide (BNP) and lactotripeptides).

Where an agent is a nucleic acid, it can be a deoxyribonucleic acid (DNA), ribonucleic acid (RNA), or can be a DNA or RNA sequence that contains one or more and up to all artificial nucleic acid analogs. Agents comprising DNA sequences can include a plurality of nucleobases including cytosine, guanine, adenine, and thymine, as well as other natural or synthetic nucleobases, or combinations thereof. The nucleobases can also include derivatives of C, G, A, or T, or synthesized nucleobases. In certain embodiments, the DNA sequences can be in one or more conformations including A-DNA, B-DNA and Z-DNA. The DNA sequences can also be in linear or branched. In certain embodiments, the DNA sequences can be single-stranded, double-stranded, or multiple-stranded.

In some embodiments, the RNA can be a messenger RNA (mRNA), transfer RNA (tRNA), ribosomal RNA (rRNA), transfer-messenger RNA (tmRNA), microRNA (miRNA), small interfering RNA (siRNA), CRISPR RNA, antisense RNA, pre-mRNA, or small nuclear RNAs (snRNA). The RNAs can also include a plurality of nucleobases including adenine, cytosine, guanine, or uracil, other natural nucleobases, or combinations thereof. In certain embodiments, the nucleobases can include derivatives of A, C, G, U, or synthesized nucleobases. The RNAs can also be in linear or branched. In certain embodiments, the RNAs can be single-stranded, double-stranded, or multi-stranded.

In some embodiments, the artificial nucleic acid analogs can include backbone analogues (e.g., hydrolysis resistant RNA-analogues, precursors to RNA world (e.g., TNA, GNA, PNA)) or base analogues (e.g., nucleobase structure analogues, fluorophores, fluorescent base analogues, natural non-canonical bases, base-pairs, metal-base pairs).

In some embodiments, the proteins can be antibodies including but not limited to antibodies of the IgG class, monoclonal antibodies, antibody fragments, or single-chain antibodies. The antibody can be naturally occurring or non-naturally occurring.

In some embodiments, CD47, SIRPα or the interaction therebetween can inhibit or deactivate one or more receptors. Thus, by inhibiting the expression or activity of SIRPα or suppressing the interaction between CD47 and SIRPα the first agent can activate the one or more receptors. In certain embodiments, the one or more receptors can also be activated by the second agent. Accordingly, by inhibiting the expression or activity of SIRPα or suppressing the interaction between CD47 and SIRPα the first agent can enhance the activity of the one or more receptors.

The first agent and/or the second agent can be administered orally or parenterally. Where the administration is parenteral, the agent(s) can be administered intravenously, intramuscularly, subcutaneously, intraperitoneally, intrapleurally, intrabrochially, vaginally, topically, via the ear, eye, or nose, sublingually, intrathecally, rectally, or into the cerebrospinal fluid. Accordingly, the invention features formulations of the present agents suitable for administration via these routes or constituting a part of a dressing or inhaler.

In various embodiments, the compositions can be formulated in the form of a pill, a capsule, a granule, a tablet, a pallet, a suspension, an injection, an infusion, a suppository, a continuous delivery system, a syrup, a tincture, an ointment, a cream, eye drops, eardrops, a flush, a lavage, a slow absorbing depot, a dressing, a lozenge, or any pharmaceutically acceptable application or as a nutritional supplement.

The first agent and/or the second agent, as disclosed herein, can be formulated with conventional carriers and excipients, which can be selected in accord with ordinary practice. Tablets can typically contain excipients, glidants, fillers, binders and the like. Aqueous formulations can be prepared in sterile form, and when intended for delivery by other than oral administration generally can be isotonic. Formulations can contain excipients (e.g., excipients set forth in the Handbook of Pharmaceutical Excipients, 5th Ed.; Rowe, Sheskey, and Owen, Eds.; American Pharmacists Association; Pharmaceutical Press: Washington, D.C., 2006). Excipients can include ascorbic acid or other antioxidants, chelating agents such as EDTA, carbohydrates such as dextrin, hydroxyalkylcellulose, hydroxyalkylmethylcellulose, stearic acid or the like.

When used for oral use, tablets, troches, lozenges, aqueous or oil suspensions, dispersible powders or granules, emulsions, hard or soft capsules, syrups or elixirs can be prepared. Compositions intended for oral use can be prepared according to any method known to the art for the manufacture of pharmaceutical compositions and such compositions may contain one or more agents including sweetening agents, flavoring agents, coloring agents and preserving agents, in order to provide a palatable preparation.

When used for injection, the pharmaceutical compositions of the first agent and/or the second agent can be in the form of a sterile injectable preparation (e.g., a sterile injectable aqueous or oleaginous suspension). The suspension can be formulated according to methods known in the art using suitable dispersing or wetting agents and suspending agents. The sterile injectable preparation can also be a sterile injectable solution or suspension in a non-toxic parenterally acceptable diluent or solvent (e.g., a solution in 1,3-butanediol or prepared as a lyophilized powder). Among the acceptable vehicles and solvents that can be employed are water, Ringer's solution and isotonic sodium chloride solution. In addition, sterile fixed oils can be conventionally employed as a solvent or suspending medium. For this purpose, any bland fixed oil can be employed (e.g., synthetic mono- or diglycerides). Fatty acids (e.g., oleic acid) can also be used in the preparation of injectables.

Formulations suitable for administration to the eye can include eye drops wherein the active ingredient is dissolved or suspended in a suitable carrier, especially an aqueous solvent for the active ingredient. Formulations suitable for topical administration in the mouth can include lozenges including the active ingredient in a flavored basis, typically sucrose and acacia or tragacanth; pastilles including the active ingredient in an inert basis such as gelatin and glycerin, or sucrose and acacia; and mouthwashes including the active ingredient in a suitable liquid carrier. Formulations for rectal administration can be presented as a suppository with a suitable base including for example cocoa butter or a salicylate. Formulations suitable for intrapulmonary or nasal administration can have a particle size in the range of 0.1 to 500 microns (including particle sizes in a range between 0.1 and 500 microns in increments microns such as 0.5, 1, 30 microns, 35 microns, etc.), which can be administered by rapid inhalation through the nasal passage or by inhalation through the mouth so as to reach the alveolar sacs. Formulations suitable for aerosol or dry powder administration can be prepared according to conventional methods and may be delivered with other therapeutic agents such as compounds heretofore used in the treatment or prophylaxis of a given condition. Formulations suitable for vaginal administration can be presented as pessaries, tampons, creams, gels, pastes, foams or spray formulations containing in addition to the active ingredient such carriers as are known in the art to be appropriate. Formulations suitable for parenteral administration can include aqueous and nonaqueous sterile injection solutions which can contain anti-oxidants, buffers, bacteriostats and solutes which render the formulation isotonic with the blood of the intended recipient; and aqueous and non-aqueous sterile suspensions which can include suspending agents and thickening agents.

The formulations can be presented in unit dose or multi-dose containers (e.g., sealed ampoules and vials) and can be stored in a freeze-dried (lyophilized) condition requiring the addition of the sterile liquid carrier (e.g., water) for injection, immediately prior to use. Extemporaneous injection solutions and suspensions can be prepared from sterile powders, granules and tablets of the kind previously described. Preferred unit dosage formulations can be those containing a daily dose or unit daily sub-dose, as herein above recited, or an appropriate fraction thereof, of the active ingredient.

If desired, the compounds of the presently disclosed subject matter can be applied in conjunction with one or more inert or inactive ingredients. The first agent and/or the second agent, as disclosed herein, can be administered by any route appropriate to the condition to be treated. Suitable routes can include oral, rectal, nasal, topical (including buccal and sublingual), vaginal and parenteral (including subcutaneous, intramuscular, intravenous, intradermal, intrathecal and epidural), and the like.

In some embodiment, the first agent and/or the second agent can also be used in combination with other active ingredients. The combinations can be selected based on the condition to be treated, cross-reactivities of ingredients and pharmaco-properties of the combination. The first agent and/or the second agent can also be combined with one or more other active ingredients in a unitary dosage form for simultaneous or sequential administration to a patient. The combination therapy can be administered as a simultaneous or sequential regimen. When administered sequentially, the combination can be administered in two or more administrations.

In general, during alternation therapy, an effective dosage of each active ingredient can be administered sequentially (i.e., serially), whereas in combination therapy, effective dosages of two or more active ingredients can be administered together. The combination therapy may provide "synergy" or a "synergistic effect" (i.e., the effect achieved when the active ingredients used together is greater than the sum of the effects that results from using the compounds separately). In certain embodiments, a synergistic effect can be attained when the active ingredients are: (1) co-formulated and administered or delivered simultaneously in a combined formulation; (2) delivered by alternation or in parallel as separate formulations; or (3) by some other regimen. In alternation therapy, the synergistic effect can also be attained when the compounds are administered or delivered sequentially (e.g., in separate tablets, pills, or capsules, or by different injections in separate syringes).

In some embodiments, the invention described above can be employed in combination with other treatments of the patient. Other treatments can include chemo therapies, surgeries, radiation therapies, hormone therapies, stem cell or bone marrow transplantations, immunotherapies, and targeted therapies.

EXAMPLES

Macrophage phagocytosis of cancer cells is regarded as a promising, powerful means for cancer eradication. Previous studies suggest that cancer cell surface CD47 interactions with SIRPα on macrophages prevent macrophage phagocytosis of self-cells and/or cancer targets, and that depletion of either proteins, or the CD47/SIRPα-mediated signaling system, promotes macrophage phagocytosis. However, this theory faces challenges at least in part because gene-knockout animals fail to demonstrate enhanced macrophage phagocytosis of tissue/cancer cells.

The invention will be further illustrated with the following non-limiting examples. In the examples, we discovered compositions and treatments that activate macrophage phagocytic potential. We also discovered that the mice subjected to such treatments successfully and completely eradicated metastatic melanoma in vivo.

Example 1. General Materials and Methods

Mice: All experimental mice were housed in an institutional pathogen-free animal facility with free access to water and food. Wild-type (WT) C57BL/6J mice and CD47 knock out (CD47$^{-/-}$) mice (B6.129-Cd47tm1Fpl/J) were purchased from The Jackson Laboratory. The strain of SIRPα knockout (SIRPα$^{-/-}$) was established through collaborations with Dr. Chen Dong at University of Texas MD Anderson Cancer Center. A neomycin resistant cassette was inserted into the SIRPα gene and replaced the exon 2, which encodes the transmembrane domain of the protein, and its flanking region (FIG. 1A). The embryonic stem (ES) clones containing the mutated structure were selected and microinjected into mouse blastocysts. Chimeric mice were generated and were confirmed to contain the mutant allele. After breeding with WT C57BL/6J mice for more than six generations, heterozygotes containing the mutant allele were selected by PCR genotyping using two pairs of gene-specific primers (For-1, 5'-ctgaaggtgactcagcctgagaaa (SEQ ID NO:7) and Rev-1, 5'-actgatacggatggaaaagtccat (SEQ ID NO:8); For-2, 5'-ttgccggtgggacccattaggtgg (SEQ ID NO:9) and Rev-2, 5'-agattgtatttctgtgtcaggctc (SEQ ID NO:10)). Another pair of primers (NeoF, 5'-tgtgctcgacgttgtcactg (SEQ ID NO:11) and NeoR, 5'-cgataccgtaaagcacgaggaagc (SEQ ID NO:12)) was used to examine the presence of neomycin cassette. Further breeding between heterozygotes produced homozygous offspring in a C57BL/6J background. WB analyses of bone marrow leukocytes, peripheral granulocytes and monocytes, peritoneal and spleen macrophages using antibodies against the SIRPα extracellular domain (mAb P84, BD biosciences) and the cytoplasmic tail confirmed absence of SIRPα expression in mutant mice.

Adoptive transfer and in vivo clearance: CD47-expressing (CD47$^+$) RBC freshly collected from WT or SIRPα$^{-/-}$ mice, and CD47-null (CD47$^-$) RBC collected from CD47$^{-/-}$ mice were labeled with carboxyfluorescein succinimidyl ester (CFSE). After washing, about 1×10$^9$ RBC suspended in 200 μl sterile PBS were transfused into recipient mice by intravenous (i.v.) injection. Blood samples (5 μl) were then collected 30 min after the blood transfusion and the CFSE-labeled RBC in the circulation was assessed by FACS analyses. Blood samples (5 μl each) were then collected at later time points to assess the clearance of CFSE-labeled RBC as compared to that found at 30 min. For each sample, at least 50,000 RBC were examined by FACS. Similar experiments were performed to test in vivo clearance of adoptively transferred splenocytes in recipient mice. For these experiments, splenocytes (2×10$^7$) harvested from CD47$^{-/-}$ mice were labeled by CFSE and transferred into recipient mice. Clearance of CFSE-labeled cells in the circulation and the spleen were analyzed by FACS analyses of blood samples and splenocytes.

Ex vivo macrophage phagocytosis: Mouse spleens were harvested and minced in cold HBSS followed by passing through nylon meshes. The spleen cells in suspensions were collected by centrifugation followed by washing. After lysis of RBC, splenocytes were plated in cell culture dishes in DMEM with 10% FBS and cultured for 2 h followed by removal of non-adherent cells. The adherent cells, ~70% being macrophages as determined by anti-F4/80 staining, were tested for phagocytosis. For phagocytosis of RBC or other tissue cells, targeted cells were labeled with CFSE prior to addition into the macrophage-containing wells. Macrophages and target cells, at a ratio of 1:5-10 for RBC or 1:1-2 for other cells, were co-incubated for 30 min at 37° C. followed by gently washing. Macrophage phagocytosis of target cells was then analyzed by fluorescence microscopy and/or by FACS. To better recognize macrophages, macrophages in wells were labeled with an anti-F4/80 or an anti-CD11b antibody. Alternatively, the freshly isolated splenocytes in suspension were incubated with CFSE-labeled RBC and other phagocytic targets for 30 min at 37° C. Macrophage phagocytosis was then determined by FACS after labeling macrophages with anti-F4/80. To test phagocytosis of apoptotic cells, B16 cells were irradiated by UV for 150 seconds at 50 J/m$^2$ strength. Apoptosis was analyzed at 2, 4, 6, 8 and 18 h post UV irradiation by labeling of the cells with anti-phosphatidylserine (PS) antibody (data not shown) or FITC-conjugated annexin V (data not shown). Cells that were confirmed to be apoptotic were trypsinized, labeled with CFSE, and then co-incubated with macrophages for 30 min at 37° C. After gentle washing, phagocytosis was analyzed by fluorescence microscopy and/or FACS. To test phagocytosis of bacteria and the fungal product zymosan, AlexaFluor-conjugated E.coli strain Staphylococcus aureus (2 μl suspension, ~2 μg) or zymosan bioparticles (1 μl suspension, ~2 μg) (both from Invitrogen) were incubated with macrophages for 30 min followed by washing and analyses. Similar procedures were performed to test phagocytosis of macrophages from various sources. To obtain peritoneal macrophages, peritonea of mice were lavaged by sterile PBS followed by centrifugation to collect cells. Cells suspended in DMEM with 10% FBS were then plated in cell culture dishes and incubated for 2 h at 37° C. followed by removal of non-adherent cells. To produce bone marrow-derived macrophages, freshly isolated bone marrow cells were culture in macrophage colony-stimulating factor (MCSF, ~10 ng/ml)-containing MEM with 10% FBS for five-six days and macrophage differentiation was confirmed by anti-F4/80 staining. To activate macrophage phagocytosis, freshly isolated or culture macrophages were treated with inflammatory cytokines or factors including IL-17 (10 ng/ml), IL-6 (10 ng/ml), TNF-α (20 ng/ml), IL-1β (10 ng/ml), IFN-γ (100 units/ml), and LPS (50 ng/ml) for 48 h (37° C.) prior to testing for phagocytosis. All recombinant murine cytokines used in the study were purchased from PeproTech, and LPS was from Sigma Chemical Co.

Cytokine levels: Levels of cytokines in serum or macrophage culture medium were assayed by sandwich ELISA (Bian et al. J Immunol. 2012, 188 (2): 844-853). In brief, capturing anti-cytokine antibodies were coated in ELISA plates overnight at 4° C. After blocking, the wells were incubated with serum or medium samples at different dilutions for 2 hours at 25° C. After washing, cytokines that bonded to wells were detected by biotin-conjugated detecting antibodies and HRP-conjugated streptavidin. Purified recombinant murine cytokines (PeproTech) at various concentrations were used as the assay standard. To assess IL-6 induction from macrophages exposure to E. coli or zymosan, E. coli (10 μg/ml) or zymosan (0.5 mg/ml) were added into macrophage culture for 2 hours followed by collecting the cell culture medium and assaying for IL-6 by ELISA.

Hemoglobin assay: To assay blood hemoglobin, 10 μl of whole blood were obtained from the tail vein followed by lysis in 1 ml distilled water. After centrifugation (13,000 rpm, 30 min), the hemoglobin-containing supernatants were collected and measured for the optical density at the wavelength of 540 nm.

Animal inflammation models: To induce peritonitis, mice (6-8 wk, 20-22 g) were intraperitoneally injected with 0.5 mg zymosan A (Sigma) in 0.5 ml sterile PBS followed by euthanasia at 2, 4, 6 and 8 hours. PMN that infiltrated the peritoneum were collected and stained using a PE-Cy7-conjugated anti-Ly-6G antibody (Biolegend; (Bian et al. J Immunol. 2012, 188 (2): 844-853); Bian et al. J Immunol. 2013, 190 (1): 411-417). To induce peritonitis repetitively, zymosan was given every other day for a total of 3 times. To induce colitis, mice were given 2% DSS via drinking water. The colitic condition was then assessed by observing diarrhea, measuring body weight loss, increases of inflammatory cytokines, the shortage of the large intestine and intestinal tissue analyses (after euthanasia). To induce macrophage phagocytosis in vivo, mice were also administered recombinant IL-17 (20 µg, Peprotech) or LPS (0.25 mg/kg, Sigma) every other day for a week.

Mouse models of B16 melanoma: B16-F10 melanoma cells (American Type Culture Collection) were cultured in DMEM with 8% FBS. B16 melanoma pulmonary metastases were established by intravenous (i.v.) injection of B16 cells ($5\times10^5$, >95% viability) suspended in 100 µl PBS through the tail vein. The mice were allowed to live to reach humane endpoints or sacrificed on day 15 post B16 inoculation for analyses of melanoma formation in the lungs and other organs. To test macrophage eradication of B16 in vivo, recombinant murine IL-17 (20 µg) was given a day after the B16 implantation and then again two additional administrations three and six days later (total 3 administrations). For SIRPα$^{-/-}$ mice survived first B16 injection, B16 cells ($5\times10^5$) were injected (i.v.) once again three months without further IL-17 administration. The mice were observed for their life spans or euthanized after 15 days for analysis of melanoma growth in the lungs. For serum treatment, WT mice with B16 inoculation were given serum samples (150 µl, every three days, 3×) derived from control mice or B16-eradicated SIRPα$^{-/-}$ mice. In other experiments, $2\times10^7$ splenocytes from control mice or B16-eradicated SIRPα$^{-/-}$ mice were transferred into WT mice. After 10 days, B16 cells were inoculated into the recipient mice and melanoma development was examined.

Analyses of anti-B16 sera: Serum samples were collected from mice with and without B16 inoculation. To test reactivity with the B16 cell surface, the serum samples were incubated with cultured B16 cells at a dilution of 1:100 in PBS with 5% FBS followed by detection with an Alexa488-conjugated goat anti-mouse IgG and immunofluorescence microscopy. In addition, Western blotting was performed. For these experiments, B16 melanoma cells ($1\times10^7$ cells) were lysed in a buffer containing 25 mM HEPES, pH 7.5, 150 mM NaCl, 2 mM MgCl$_2$, and protease inhibitors using a Dounce homogenizer, followed by centrifugation at 1000×g for 5 min to remove cell debris. Supernatants were collected and centrifuged with a SW55 Ti Swinging Bucket Rotor at 55,000 rpm (368,000×g) for 30 min (4° C.). The pellets containing cell membranes were dissolved in a buffer containing 1% Triton X-100 followed by using in WB for analyses of serum reactivity.

Example 2. Acute Anemia in Mice Deficient of CD47-SIRP☐-Mediated Inhibition Under Inflammatory Conditions As shown in FIG. 1A, a strain of SIRPα KO (SIRPα$^{-/-}$) mice was established by targeted inactivation of the SIRPα gene in embryonic cells. PCR genotyping and immunoblot (Western blot (WB)) confirmed disruption of the SIRPα gene and depletion of SIRPα protein expression. Similar to CD47$^{-/-}$ mice, SIRPα$^{-/-}$ mice appeared healthy under the standard specific pathogen-free (SPF) housing conditions, having displayed no tissue/organ damage suggestive of enhanced macrophage phagocytosis toward self.

Figure 1B:
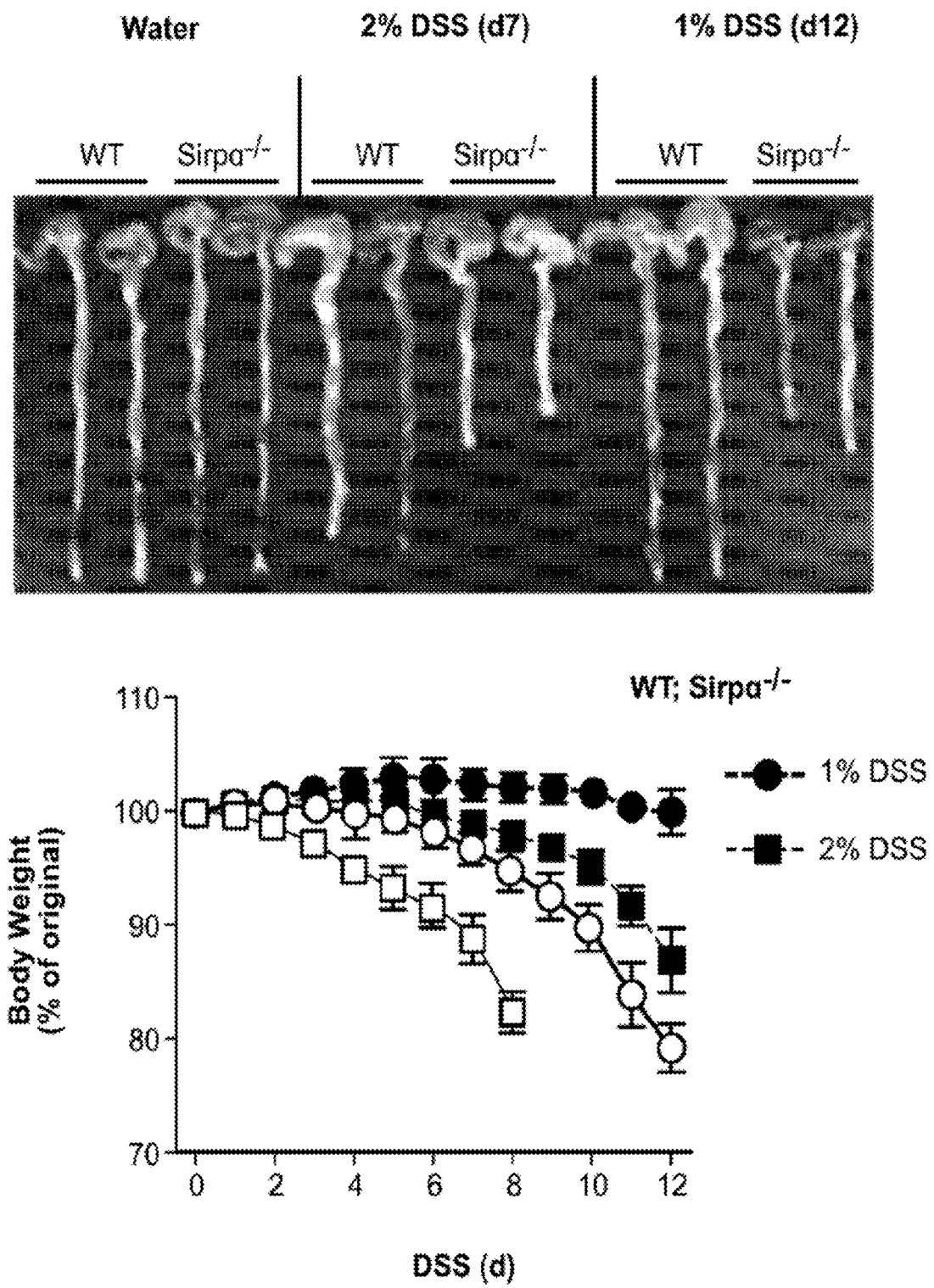
Figure 1C:
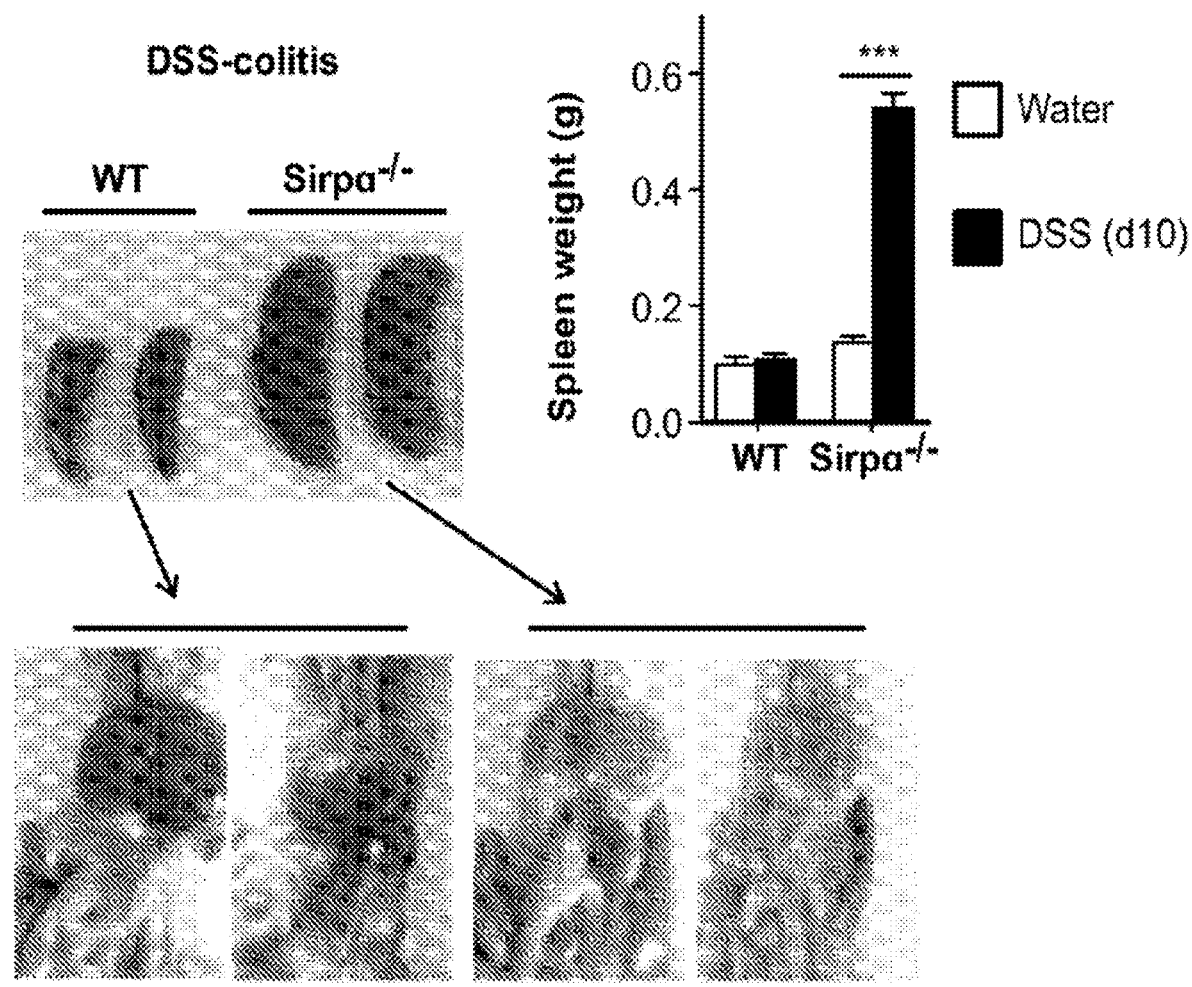
Figure 1D:
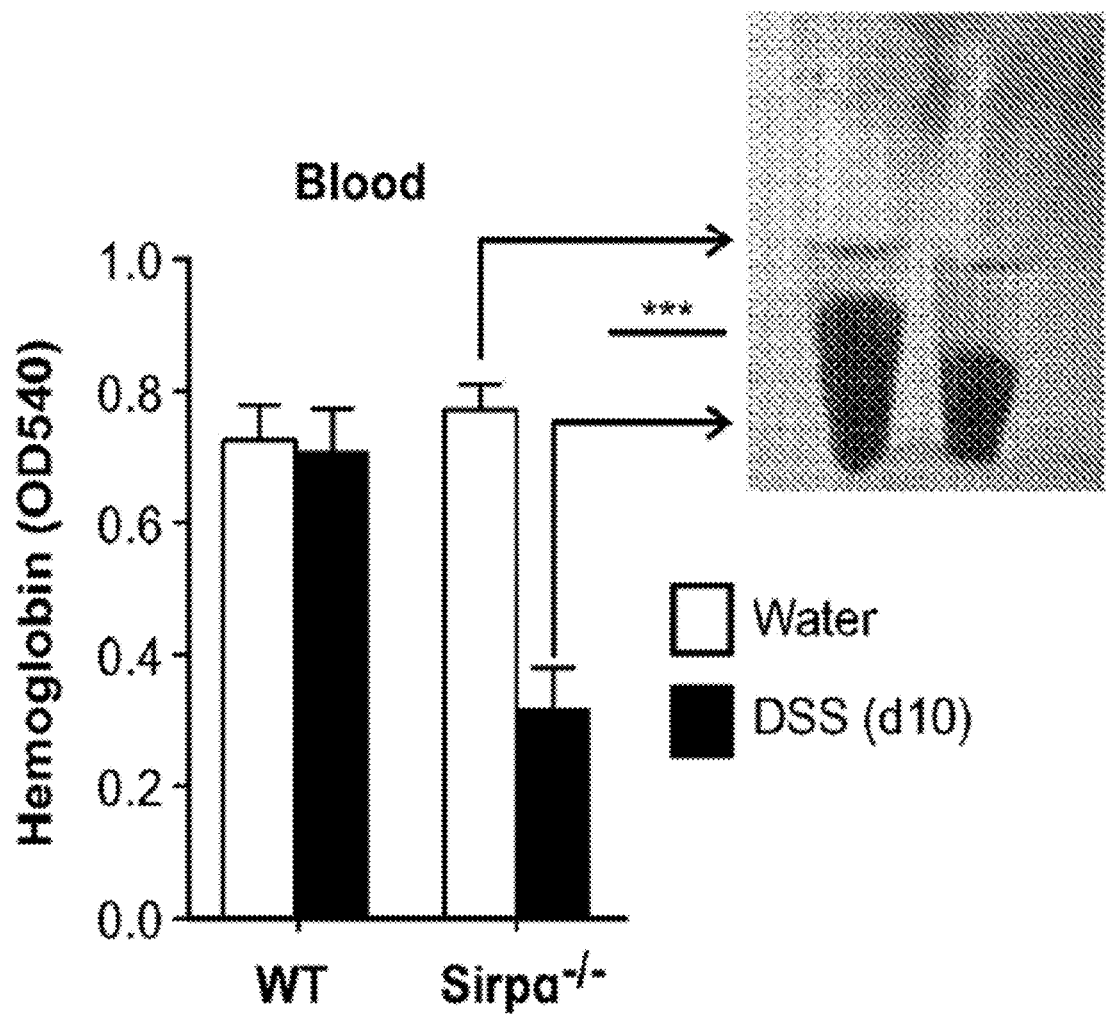
Figure 1E:
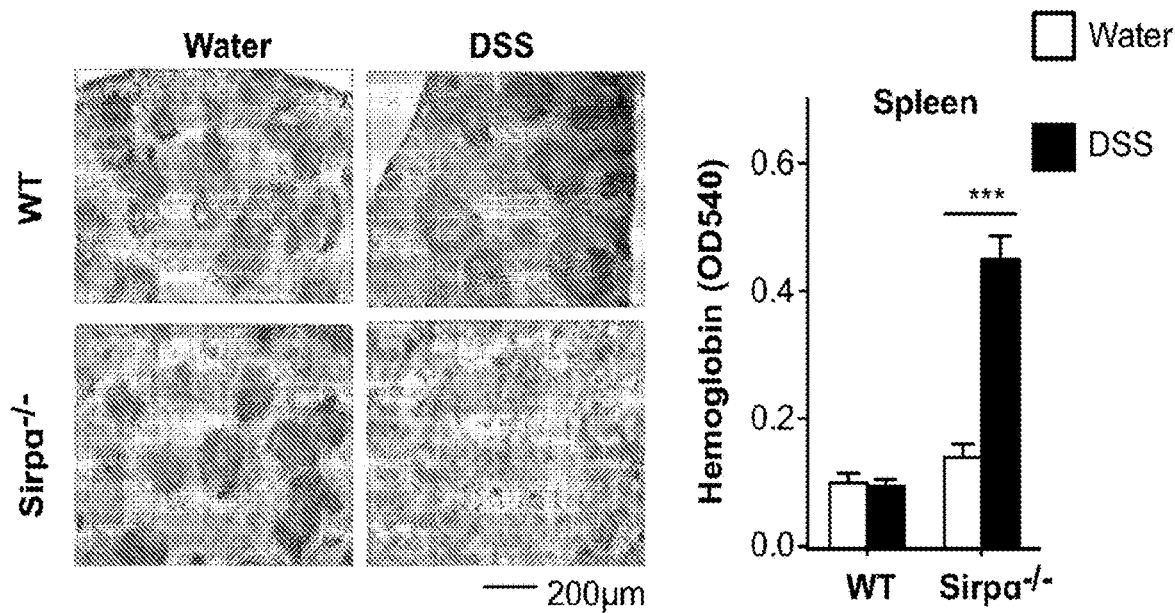

However, when inducing colitis with low-dose dextran sodium sulfate (DSS, 1-2%), SIRPα$^{-/-}$ mice displayed not only severe colitis but also acute anemia; the latter was associated with enhanced macrophage erythrophagocytosis in the spleen. As shown in FIG. 1B, compared with WT littermates, SIRPα$^{-/-}$ mice developed more severe colitis, demonstrating faster body weight loss, worse diarrhea/clinical scores, and enhanced PMN infiltration into intestines under DSS treatment. Given that SIRPα-mediated inhibitory signaling negatively regulates leukocyte inflammatory response, it was not surprising that SIRPα deficiency exacerbates DSS-induced colitis. Similar results have been observed in our previous study using mice with a truncated SIRPα cytoplasmic domain (Zen et al., *Nat. Commun.* 4:2436, 2013). Referring to FIGS. 1C and 1D, strikingly, colitic SIRPα$^{-/-}$ mice, but not WT mice, also developed significant splenomegaly and acute anemia. Pale-colored abdominal cavities were seen in colitic SIRPα$^{-/-}$ mice, which were confirmed as anemia by peripheral hemoglobin reduction (40-50). Dissection of the animals enlarged spleens revealed an extensive expansion of red pulp, to the point of disrupting the white pulp structure. Referring to FIG. 1E, spleen hemoglobin assays confirmed splenomegaly associated with increased RBC trapping, suggestive of aggressive erythrophagocytosis by red pulp macrophages. Together, these results suggest that active colitis induces macrophage-mediated RBC destruction in SIRPα$^{-/-}$ mice.

Figure 1F:
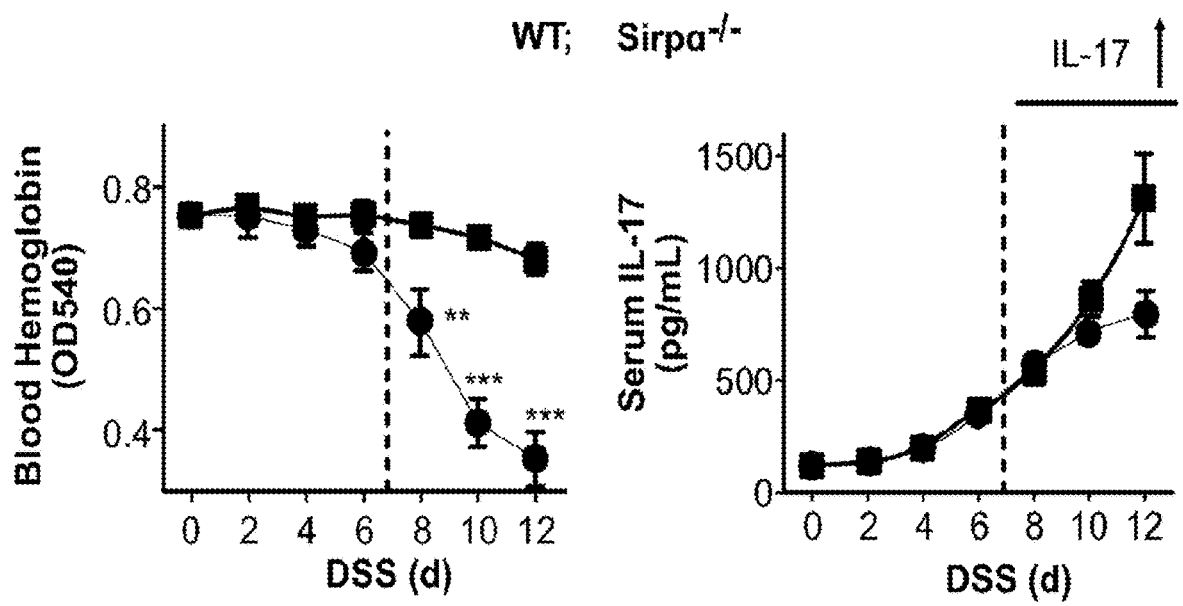
Figure 1G:
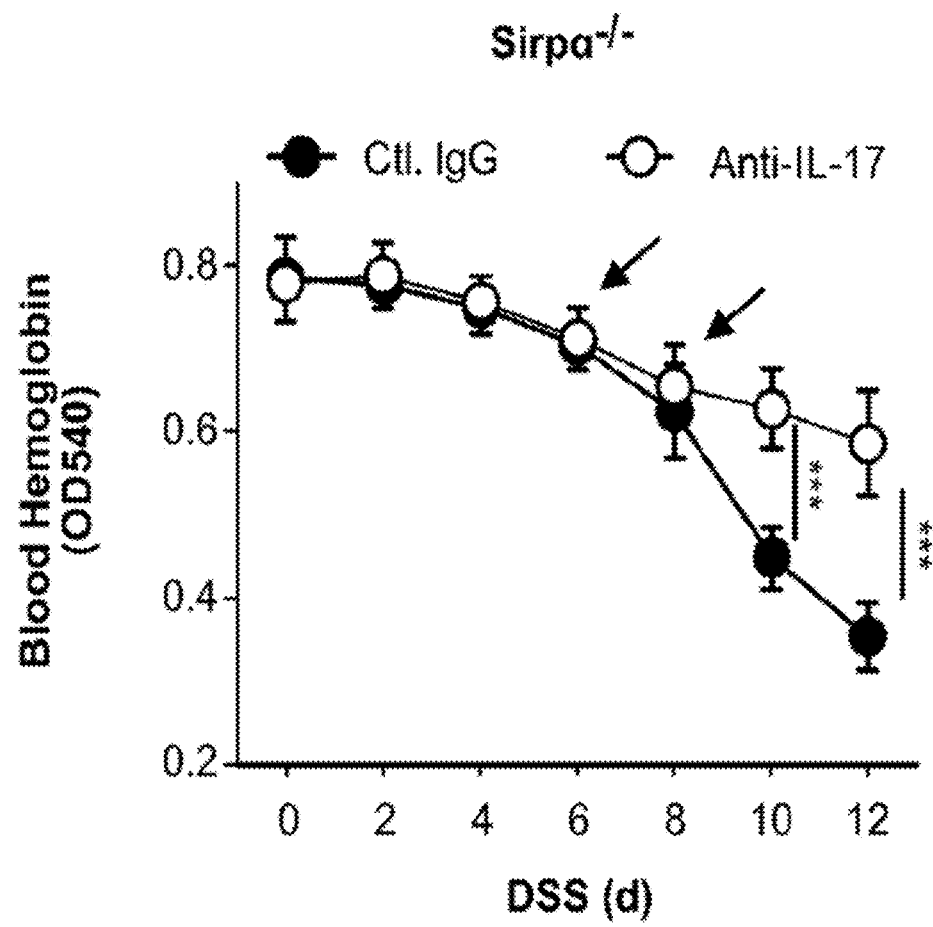
Figure 1H:
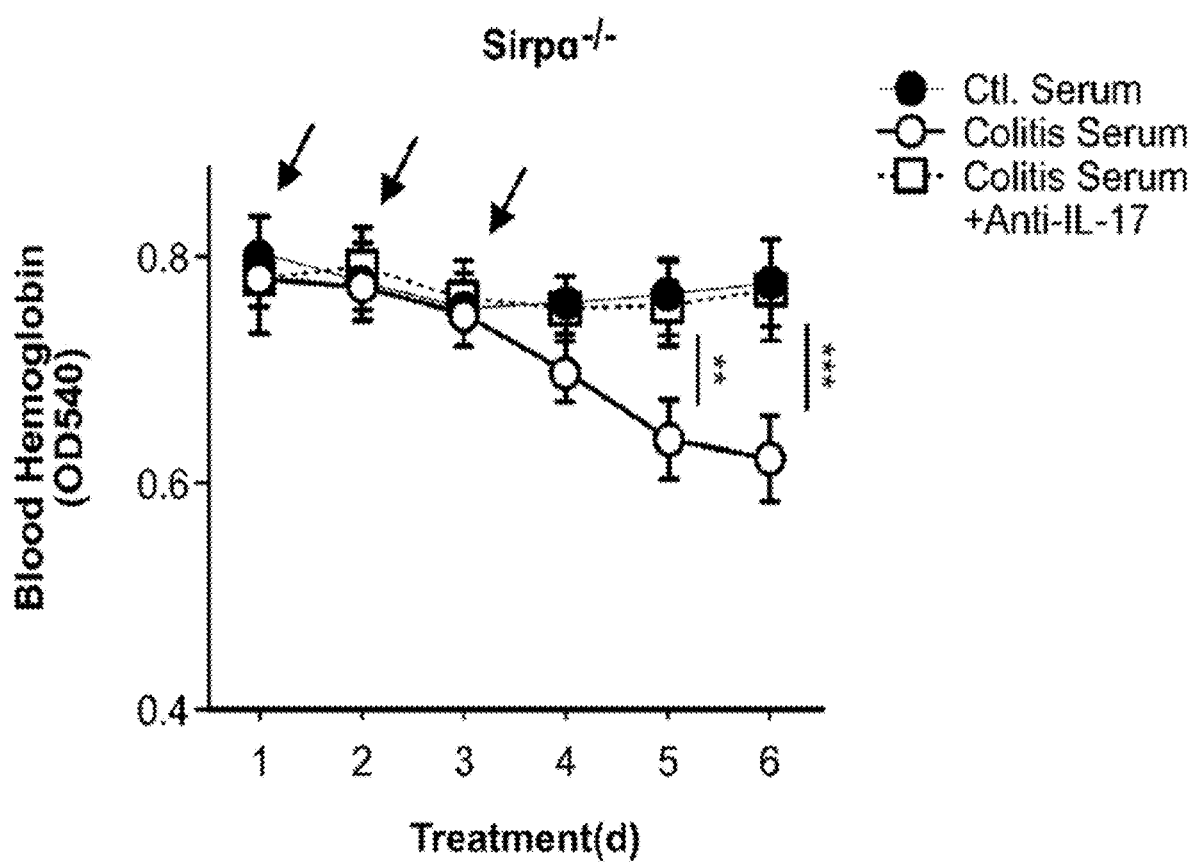
Figure 1I:
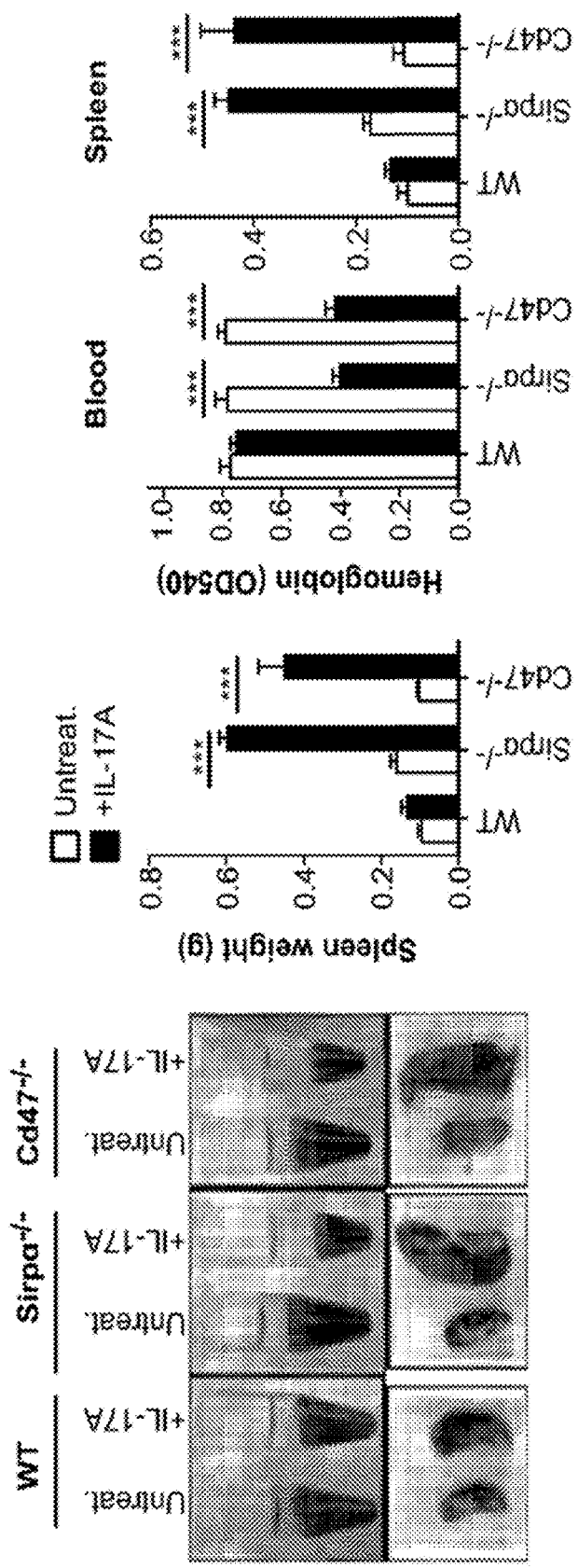
Figure 1J:
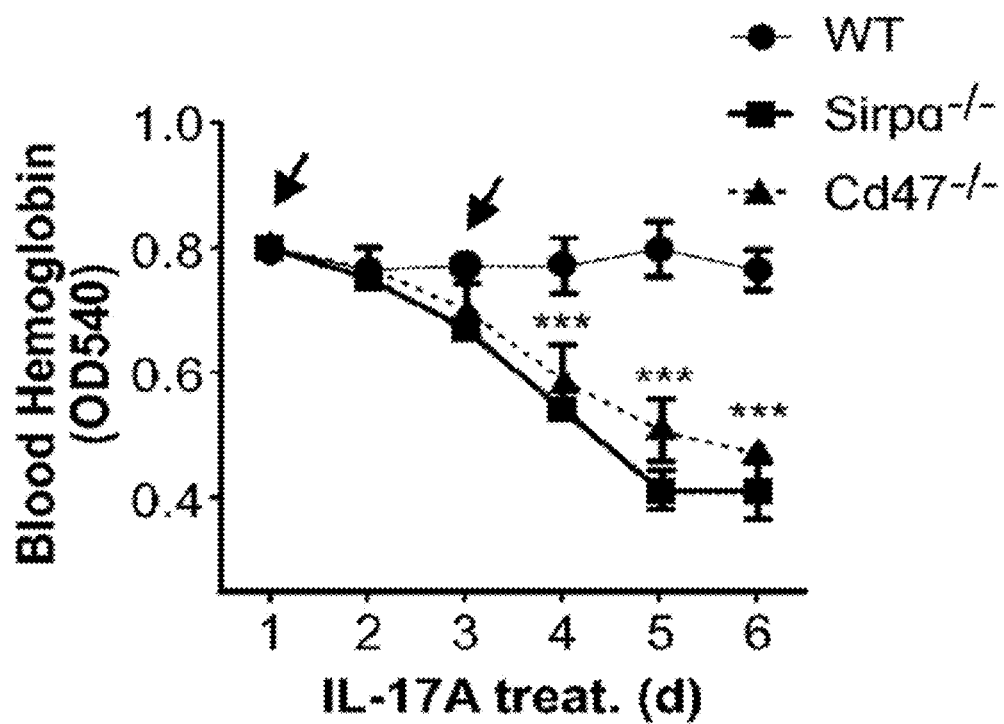

Further analyses revealed that the anemia developed in colitic SIRPα$^{-/-}$ mice was associated with IL-17. As shown in FIG. 1F, the anemia progressed slowly at the initial phase during colitis but was abruptly aggravated after days 7-8 when IL-17 started to arise in the serum. As demonstrated by us previously, IL-17 is highly induced at the postacute/chronic phase of DSS-induced colitis (Bian et al., *J. Immunol.* 188 (2):844-853, 2012; Bian et al., *J. Immunol.* 190 (1):411-417, 2013). To test whether IL-17 played a role, we performed three experiments. First, SIRPα$^{-/-}$ mice under DSS-induced colitis were given an anti-IL-17 neutralization antibody. As shown in FIG. 1G, giving anti-IL-17 antibody on day 6 and 8 when IL-17 arises during DSS-induced colitis largely ameliorated anemia and splenomegaly in SIRPα$^{-/-}$ mice. Second, healthy SIRPα$^{-/-}$ mice were administrated with colitis serum samples that contained high levels of IL-17. As shown in FIG. 1H, injections of colitis serum into SIRPα$^{-/-}$ mice directly induced acute anemia. The effect was confirmed to be specific as control serum from healthy mice or colitis serum mixed with anti-IL-17 antibody failed to cause anemia. Third, a recombinant IL-17 was administered into healthy SIRPα$^{-/-}$ mice. Referring to FIGS. 1I and 1J, injections of IL-17 alone ($2\times10$ µg/kg, i.v.) directly induced acute anemia and splenomegaly in SIRPα$^{-/-}$ mice. Notably, IL-17 injection also induced acute anemia and splenomegaly in CD47$^{-/-}$ mice. As reported previously, CD47$^{-/-}$ mice are resistant to low-dose DSS-induced colitis and are defective for IL-17 induction in vivo (Bian et al., *J. Immunol.* 190 (1):411-417, 2013; Fortin et al., *J. Exp. Med.* 206 (9):1995-2011, 2009). This explains why low-dose DSS treatment does not induce anemia in CD47$^{-/-}$ mice, as anemia is secondary to the colitic condition and colitis-induced IL-17 (data not shown).

Figure 1K:
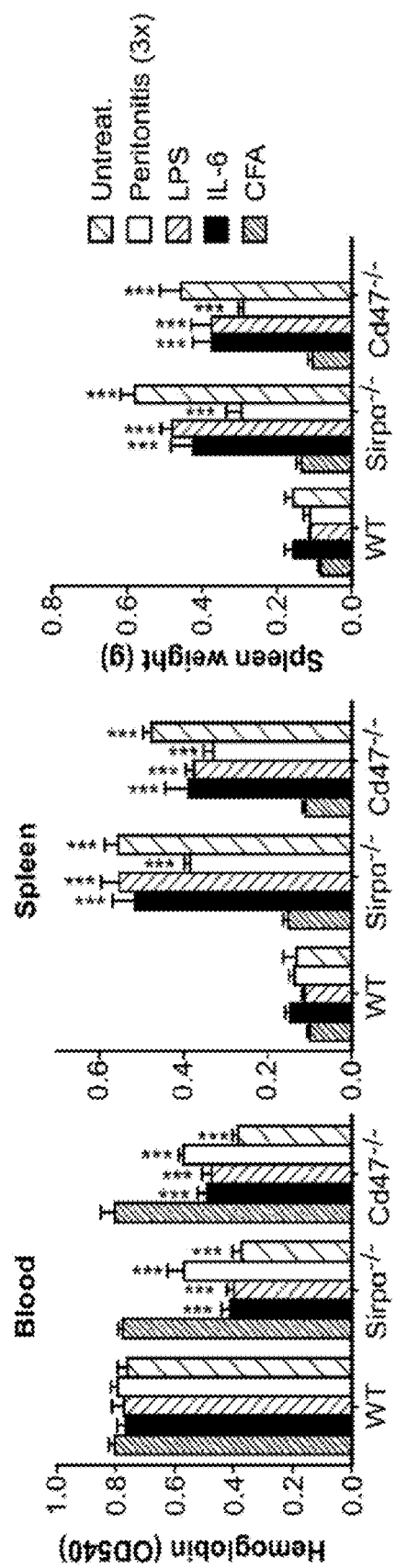

In addition to colitis, other inflammatory conditions and cytokines, such as zymosan-induced peritonitis, LPS, and Freund's complete adjuvant (CFA)-induced inflammation, also induced anemia and splenomegaly in mice lacking SIRPα or CD47. As shown in FIG. 1K, repetitively inducing peritonitis by zymosan (3 times every other day) led to severe anemia and splenomegaly in SIRPα$^{-/-}$ and CD47$^{-/-}$ mice, albeit this condition, per se, is short termed and self-resolving. Administration of IL-6 ($2\times10$ µg/kg, i.v.), the signature cytokine associated with zymosan-induced peritonitis, also induced the same result. Injection of low-dose LPS (0.25 mg/kg, i.p.), or CFA (s.c.), in SIRPα$^{-/-}$ and CD47$^{-/-}$ mice induced anemia and splenomegaly as well.

Example 3. In Vivo Assessment of Macrophage Phagocytosis by Adoptive Transfer

Figure 2A:
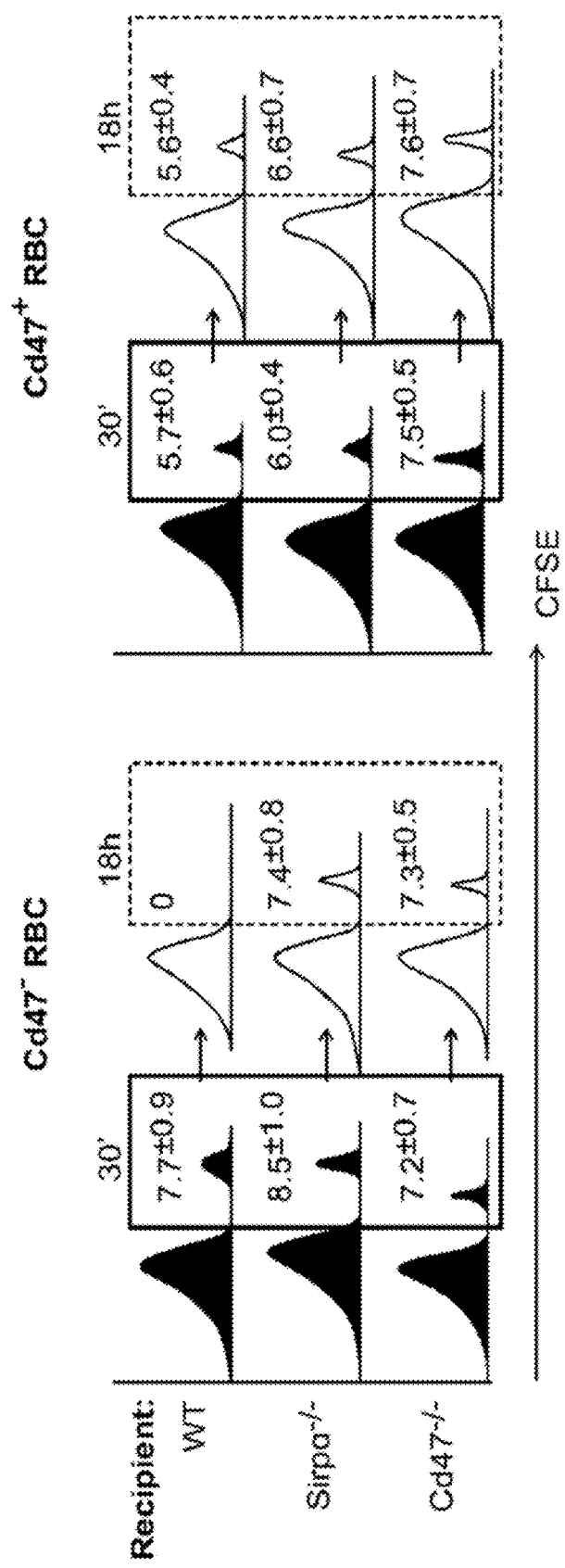
FIGS. 2A-2E includes data related to macrophage phagocytosis in vivo assessed by adoptive transfer experiments.
Figure 2B:
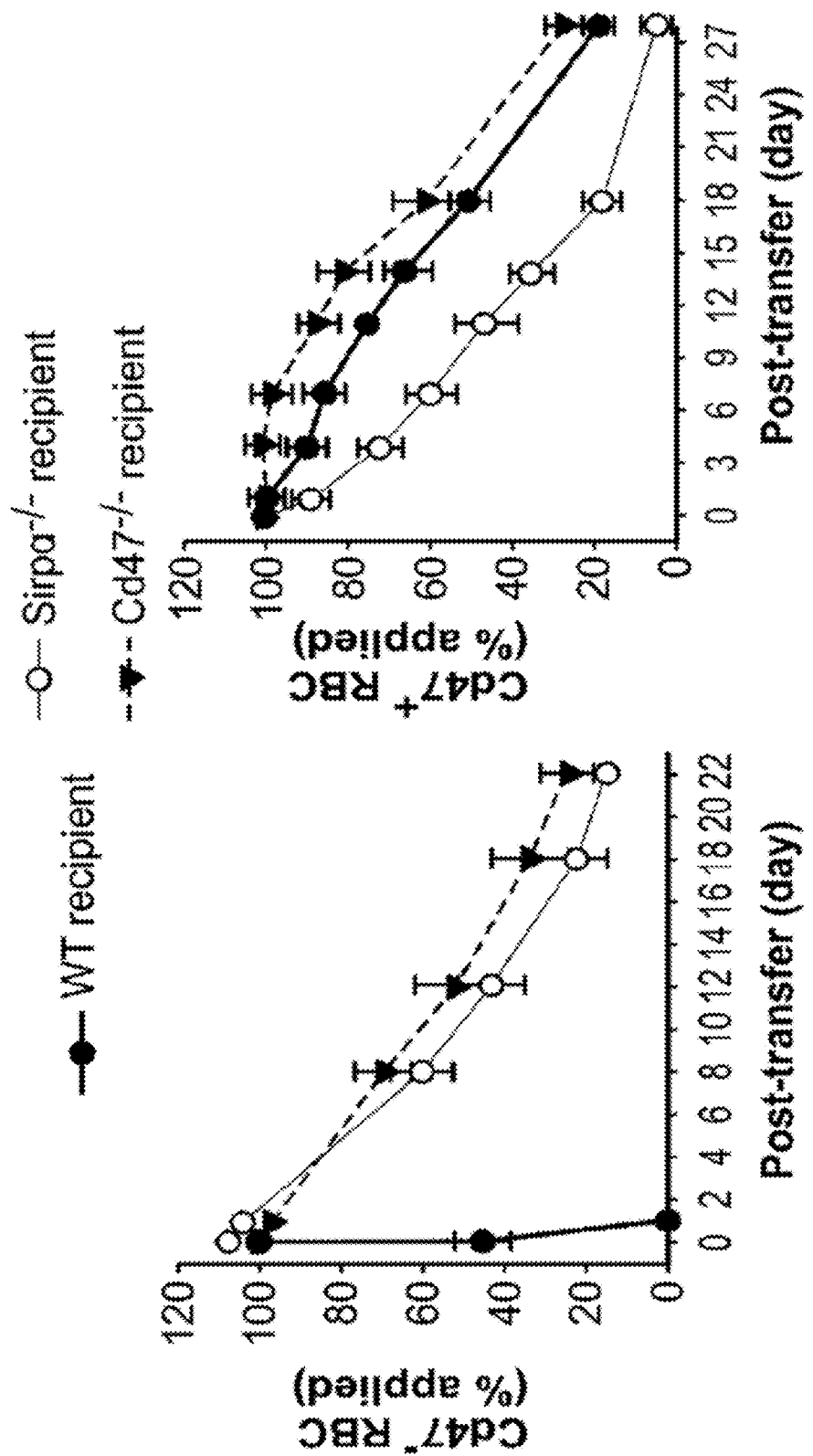
Figure 2C:
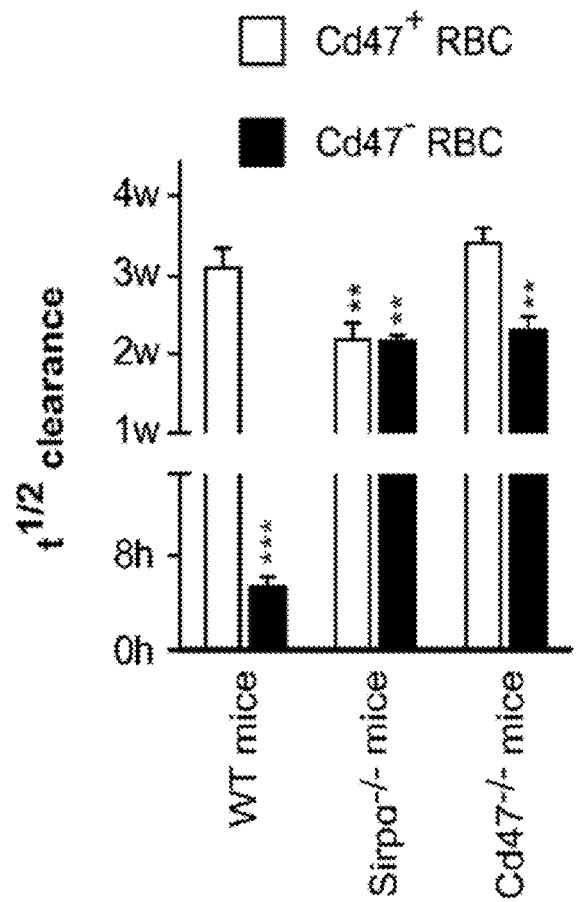

RBC adoptive transfer experiments were performed to further assess macrophage phagocytosis in vivo. CD47$^+$ or CD47⁻ RBCs isolated from WT or CD47⁻ᐟ⁻ mice, respectively, were labeled with carboxyfluorescein succinimidyl ester (CFSE), followed by transfer into different recipient mice and assessment of their clearance. As shown in FIGS. 2A-C, WT recipients swiftly cleared CD47-RBCs in a few hours ($t^{1/2}$<5 h), but retained CD47⁺ RBC for over a month ($t^{1/2}$~3 wk), a time length matching the normal life span of RBCs in the circulation. This result is consistent with a previous report (Oldenborg et al., Science 288 (5473):2051-2054, 2000), suggesting the absence of CD47-SIRPα-mediated inhibition is associated with erythrophagocytosis in the spleen. However, this manner of rapid clearance did not occur in SIRPα⁻ᐟ⁻ or CD47⁻ᐟ⁻ mice, which retained both CD47⁺ RBCs and CD47⁻ RBCs for extended time periods. Adoptive transfer of splenocytes produced the same results; the only rapid clearance found was in WT recipients to which CD47⁻ splenocytes were transferred. Thus, different from WT mice, SIRPα⁻ᐟ⁻ and CD47⁻ᐟ⁻ mice do not eliminate RBCs because of merely missing the CD47-SIRPα-mediated inhibition.

Figure 2D:
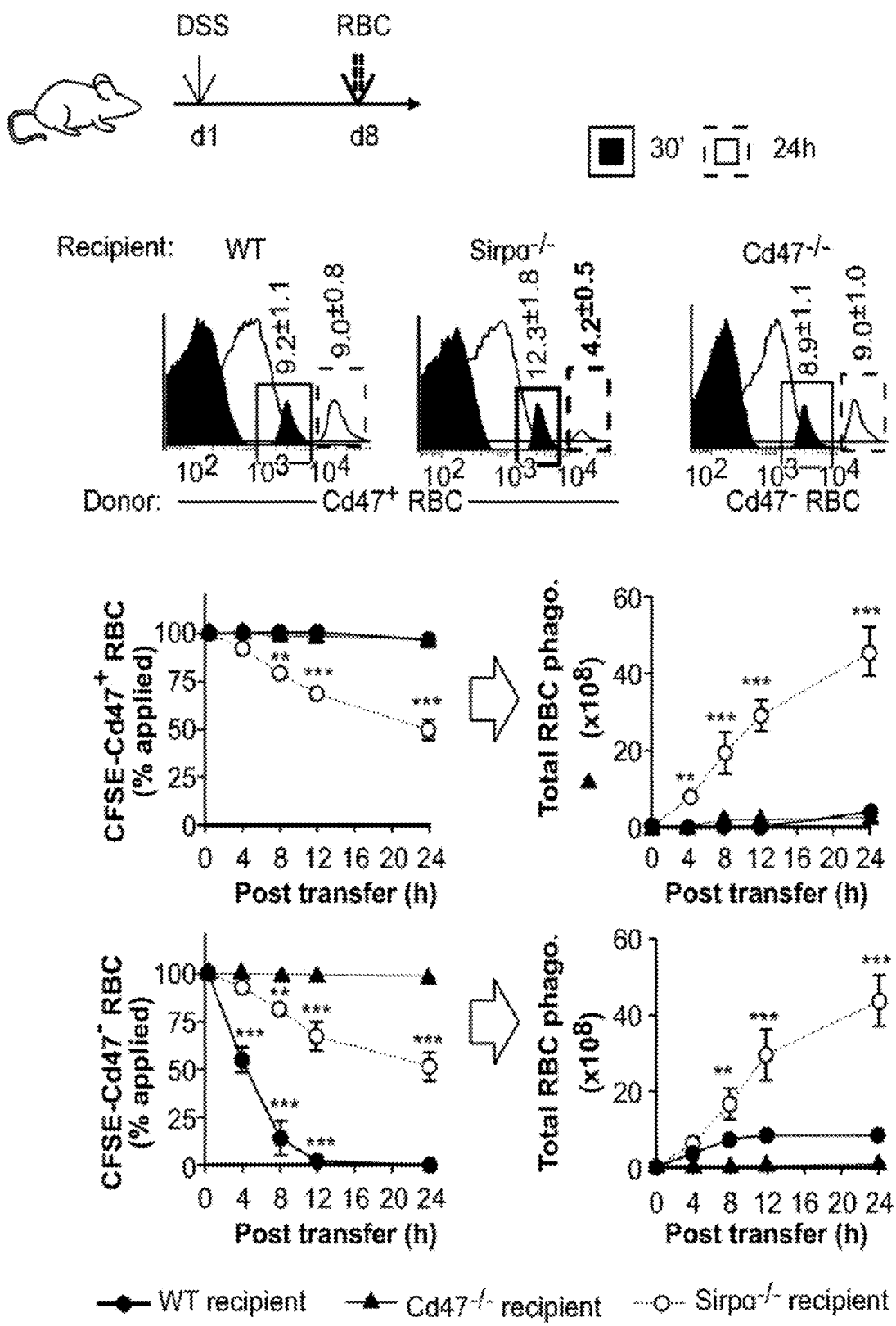
Figure 2E:
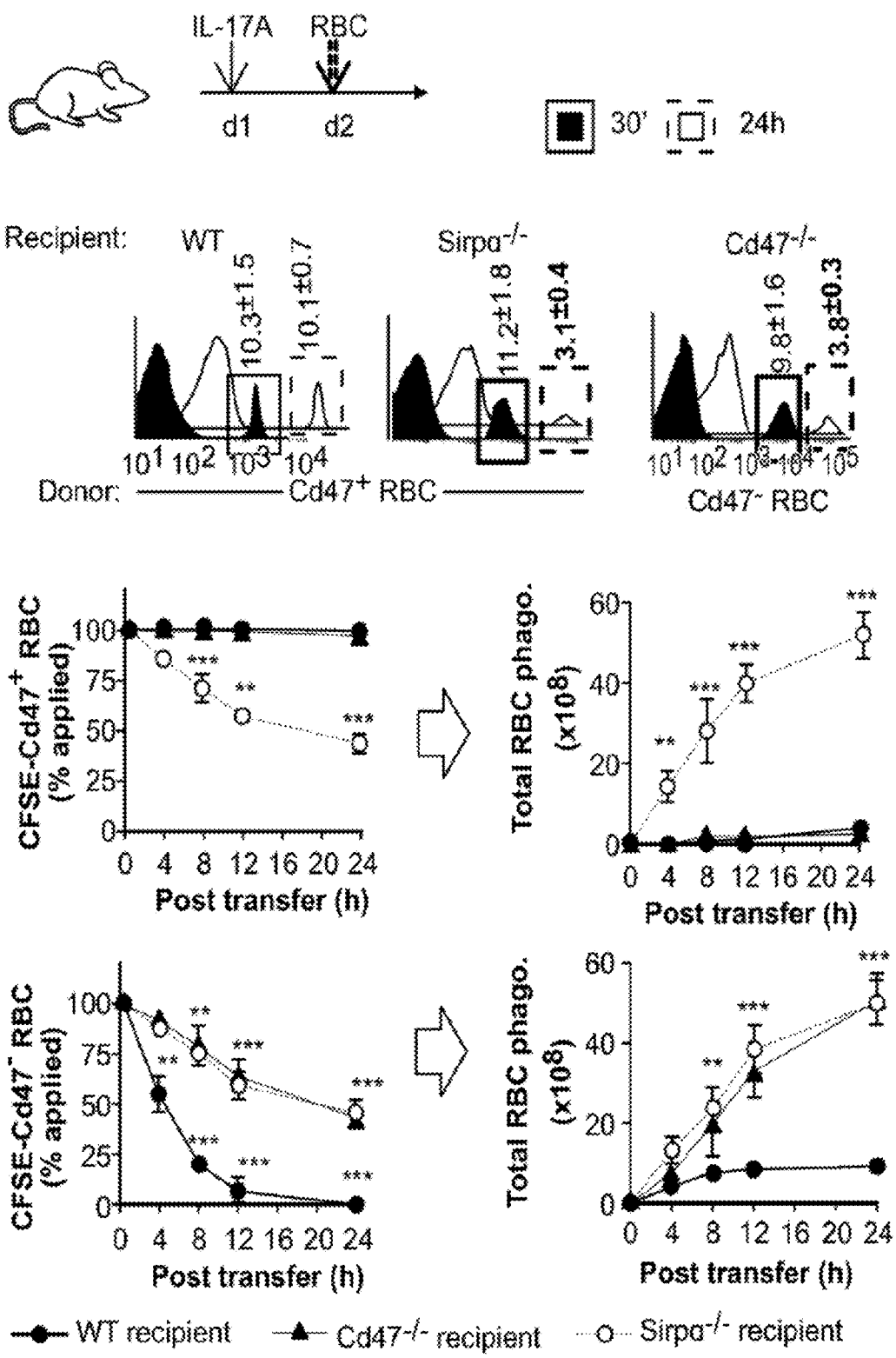

However, treating SIRPα⁻ᐟ⁻ and CD47⁻ᐟ⁻ mice with IL-17, or inducing inflammatory conditions in these mice, instantly induced accelerated RBC clearance. As shown in FIGS. 2D and 2E, SIRPα⁻ᐟ⁻ mice with 1% DSS for 8 d (when IL-17 started to arise) or who were directly injected with IL-17 displayed rapid clearance of transferred CD47⁺ and CD47⁻ RBCs (~50%, 24 h). That SIRPα⁻ᐟ⁻ mice cleared both CD47⁺ and CD47⁻ RBCs was predictable, as macrophages in these mice experience no inhibition by the CD47-SIRPα mechanism. Following this line, the RBC clearance in SIRPα⁻ᐟ⁻ mice under DSS or IL-17 treatment was indeed much more extensive than the clearance of CFSE-labeled RBCs had shown, as SIRPα⁻ᐟ⁻ macrophages in these mice would phagocytose not only the transferred RBCs but also endogenous RBCs concomitantly. Based on the CFSE-RBC clearance rate, the estimated total RBCs phagocytosed in DSS/IL-17-treated SIRPα⁻ᐟ⁻ mice should be more than 5×10⁹ in 24 h (nearly 50% of peripheral RBCs without considering increased erythrogenesis; FIGS. 2D and 2E). Comparably, WT mice cleared only the transferred CD47⁻ RBCs (~1×10⁹). Accelerated RBC clearance was also observed in CD47⁻ᐟ⁻ mice under IL-17 treatment, and only toward CD47⁻ RBCs. As expected, no enhanced clearance was observed in CD47⁻ᐟ⁻ mice treated by DSS, as DSS induced no colitis or IL-17. Interestingly, we observed that macrophage phagocytosis can reach a plateau. As shown in FIG. 2E, mutant mice treated with one dose of IL-17 for 1 d rapidly cleared the transferred RBCs, whereas the same mice treated with IL-17 for multiple times and a longer period (d1 and d3) displayed only weak clearance of transferred RBCs (<5%, 24 h). As the latter recipient mice had already developed acute anemia and splenomegaly by the time RBC transfer was performed, the result suggests a capacity saturation of macrophages as per observations also stated by others (Yamao et al., J. Biol. Chem. e:39833-39839, 2002).

Example 4. Ex Vivo Studies of Macrophage Phagocytosis

Figure 3A:
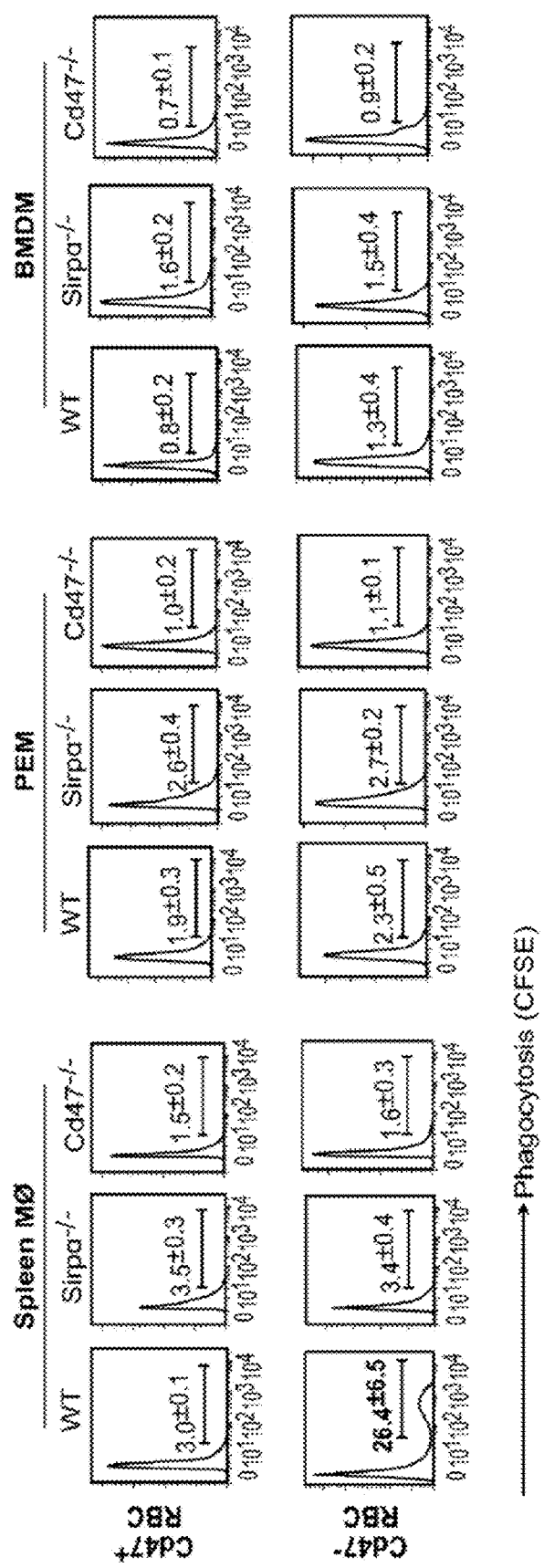
FIGS. 3A-3H include data related to our experiments assaying macrophage phagocytosis ex vivo.
Figure 3B:
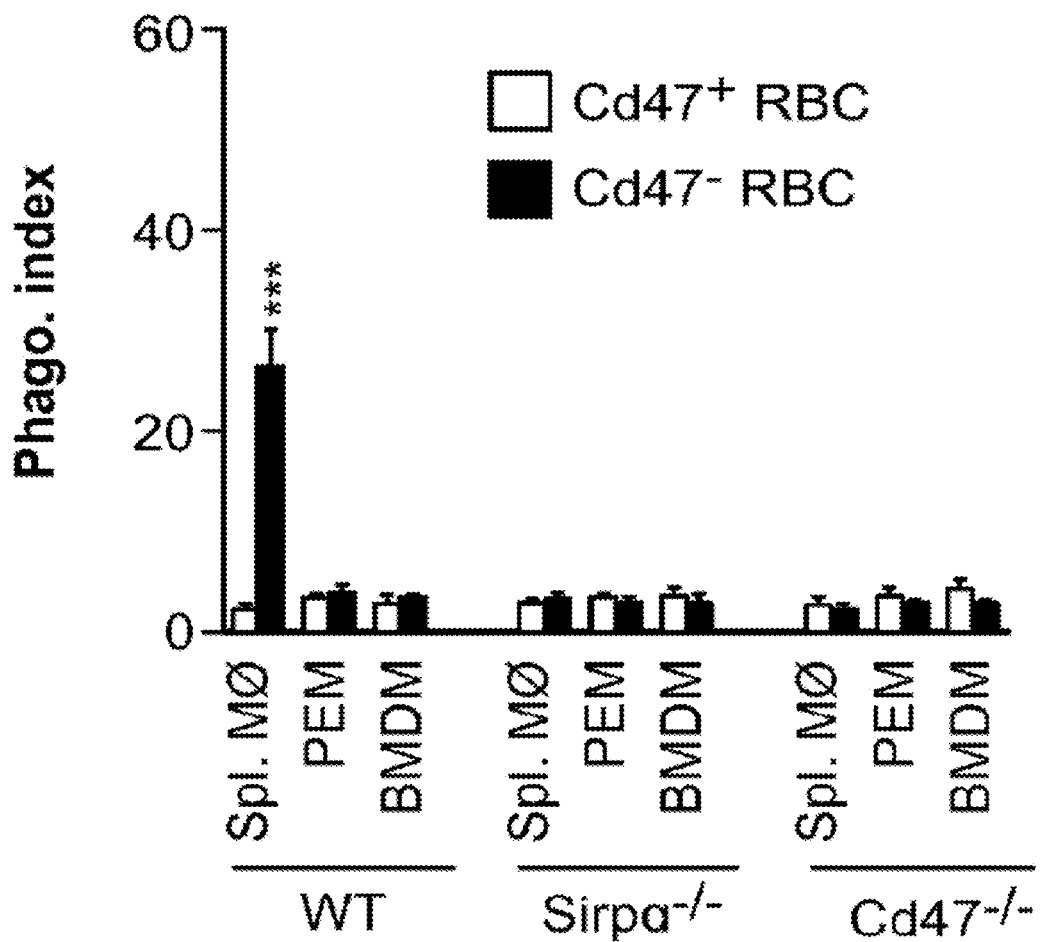
Figure 3C:
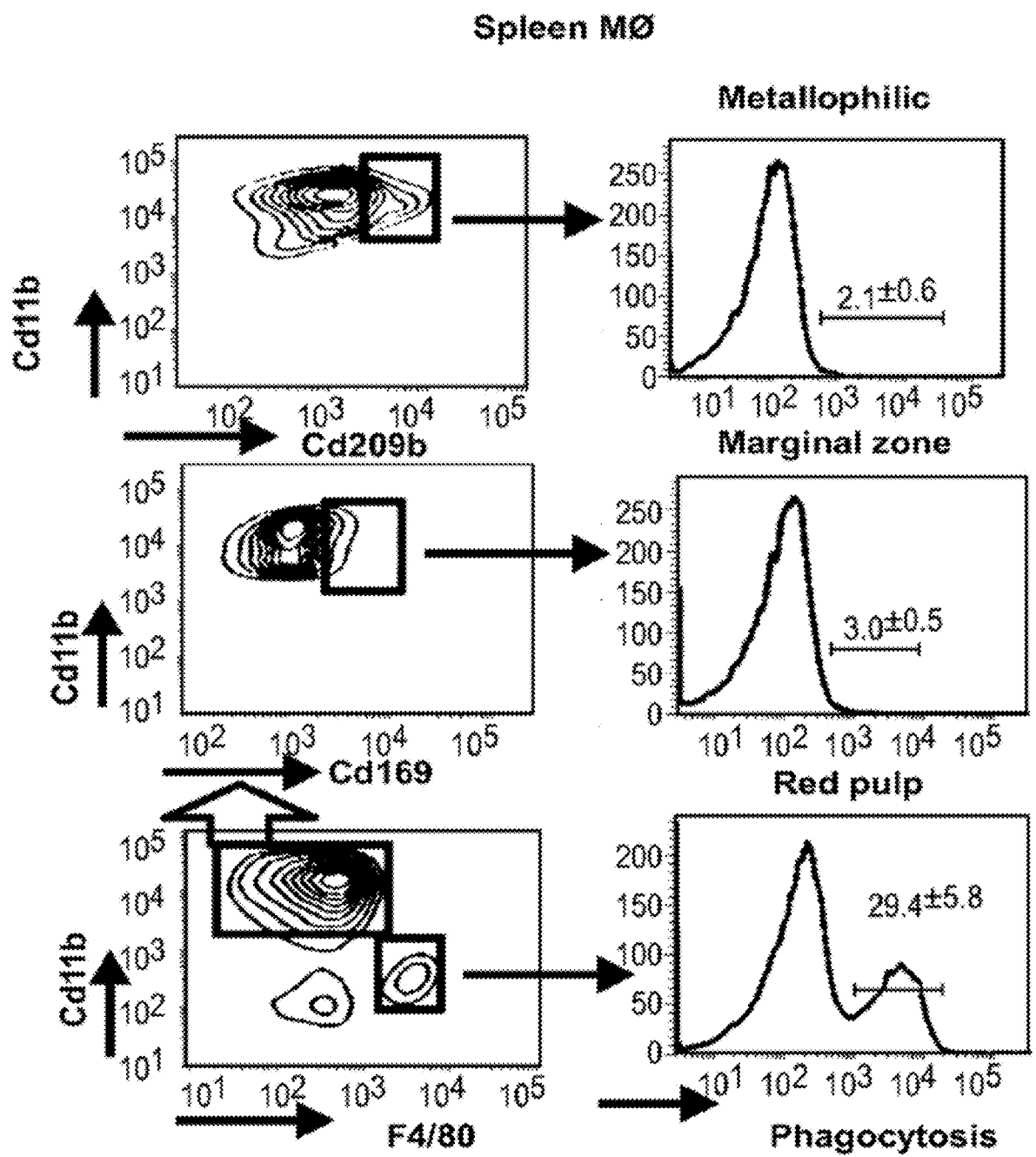

To understand the functional differences between macrophages in SIRPα⁻ᐟ⁻ or CD47⁻ᐟ⁻ mice and macrophages in WT mice, and to understand how macrophages in SIRPα⁻ᐟ⁻ or CD47⁻ᐟ⁻ mice changed their phagocytic characteristics and became erythrophagocytic under inflammatory conditions, we examined macrophage phagocytosis ex vivo. Three different tissue macrophages including splenic macrophages, peritoneal macrophages (PEMs), and bone marrow-derived macrophages (BMDMs) were tested. As shown in FIGS. 3A and 3B, consistent with in vivo studies, splenic macrophages freshly isolated from WT mice directly phagocytosed CD47⁻ RBCs, whereas those from SIRPα⁻ᐟ⁻ or CD47⁻ᐟ⁻ mice displayed no phagocytosis. To our surprise, none of the PEMs or BMDMs from any mice displayed phagocytosis toward RBCs, irrespective of CD47 expression. The fact that PEMs and BMDMs from WT mice failed to phagocytose even CD47⁻ RBCs was surprising, as splenic macrophages derived from the same mice displayed direct phagocytosis. Accordingly, the macrophages affected by the compositions described herein or used in the methods of treatment described herein can be splenic macrophages (e.g., red pulp macrophages such as F4/80⁺ red pulp macrophages). Referring to FIG. 3C, further FACS analysis of WT splenic macrophages after CD47⁻ RBC phagocytosis revealed that the phagocytic macrophages were F4/80⁺ red pulp macrophages, whereas other macrophages, such as F4/80⁻ Cd169⁺ metallophilic macrophages and F4/80⁻ CD209b⁺ marginal zone macrophages (Oldenborg et al., Science 288 (5473):2051-2054, 2000; Davies et al., Nat. Immunol. 14 (10):986-995, 2013; Gordon et al., Immunol. Rev. 262 (1):36-55, 2014), displayed no phagocytosis. Testing macrophage phagocytosis toward splenocytes obtained the same results. In summary, among various macrophages tested in these experiments, only red pulp macrophages freshly isolated from WT mice were phagocytic toward self-cells, whereas other splenic macrophages, PEMs and BMDMs, and red pulp macrophages from mutant mice were all incapable of phagocytosis irrespective of the CD47 expression on target cells. Meanwhile, testing the same macrophages for phagocytosis toward other targets that express the classical eat-me signals revealed that all macrophages, irrespective of their origins and phagocytic behavior toward self-cells, were potent phagocytes toward Escherichia coli, zymosan, apoptotic cells, antibody, or complement-bound targets.

Example 5. Macrophage Phagocytic Plasticity

Figure 3D:
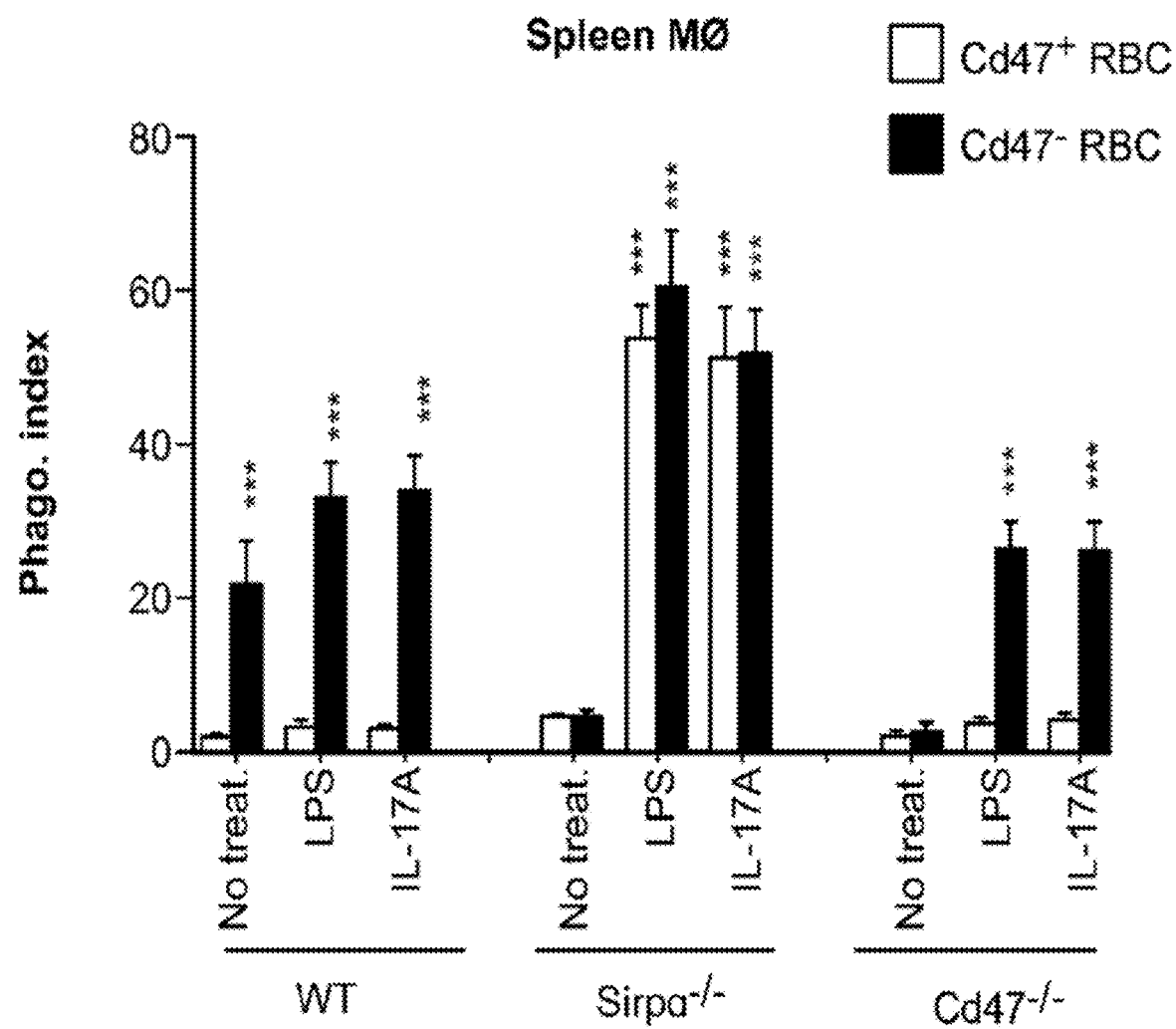
Figure 3E:
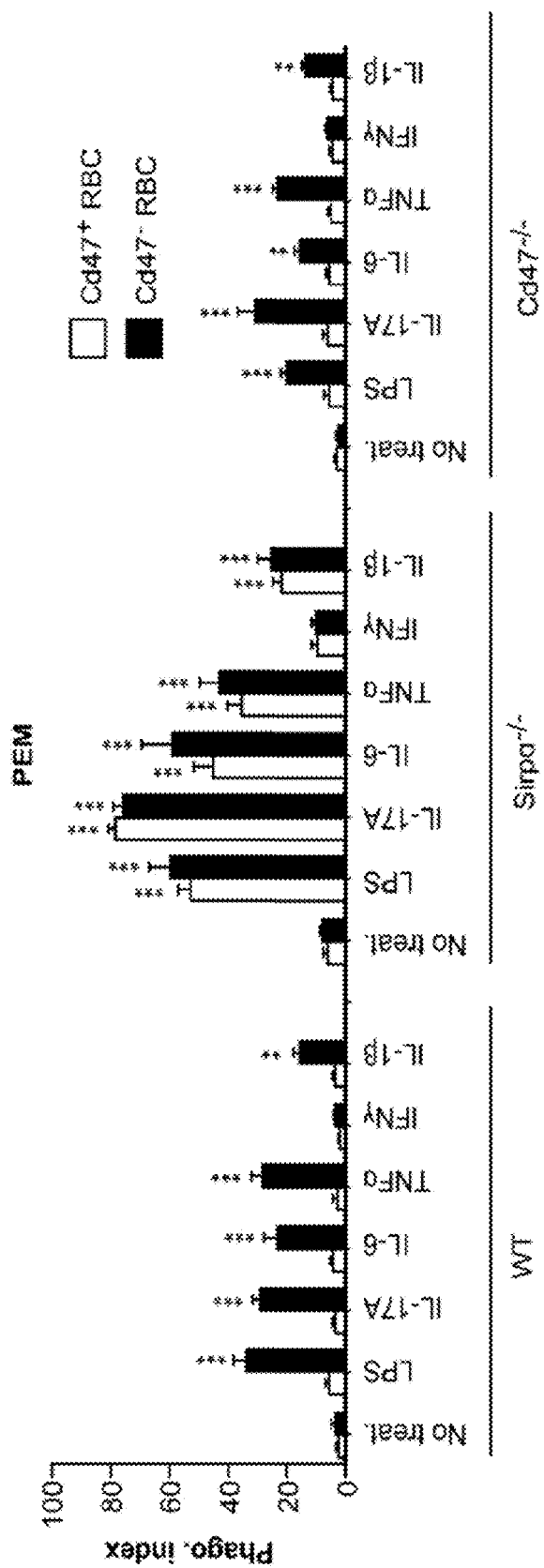
Figure 3F:
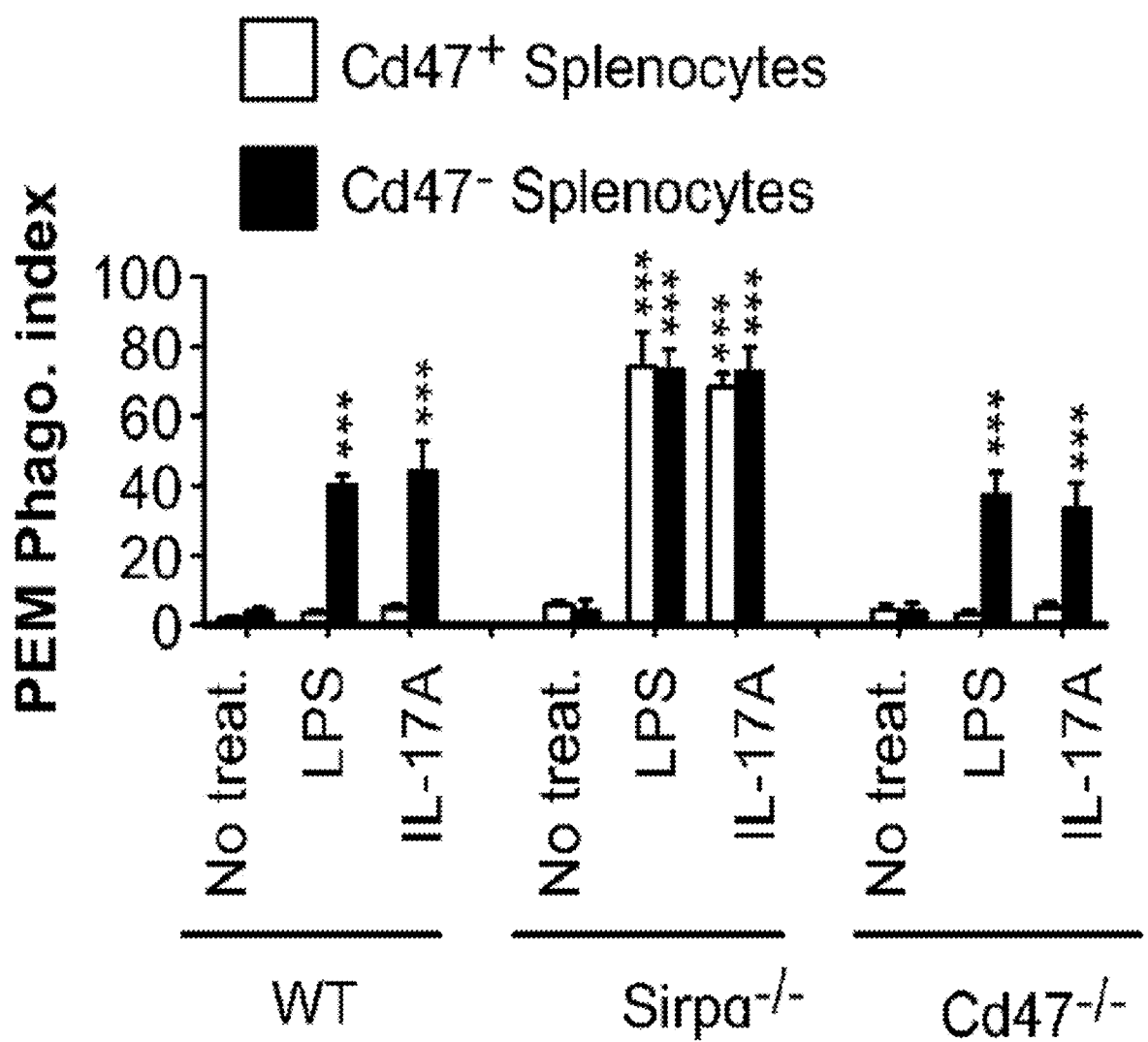
Figure 3G:
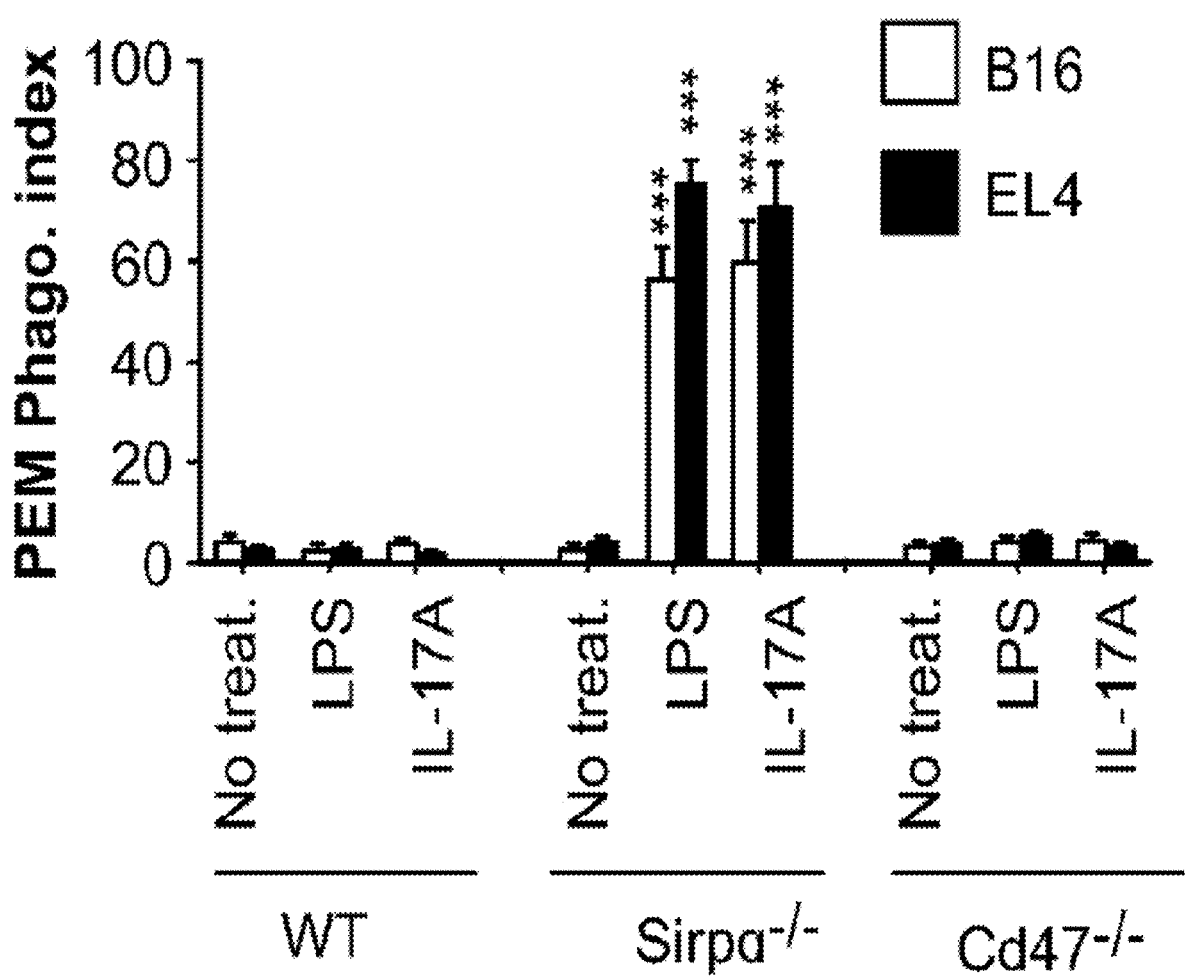
Figure 3H:
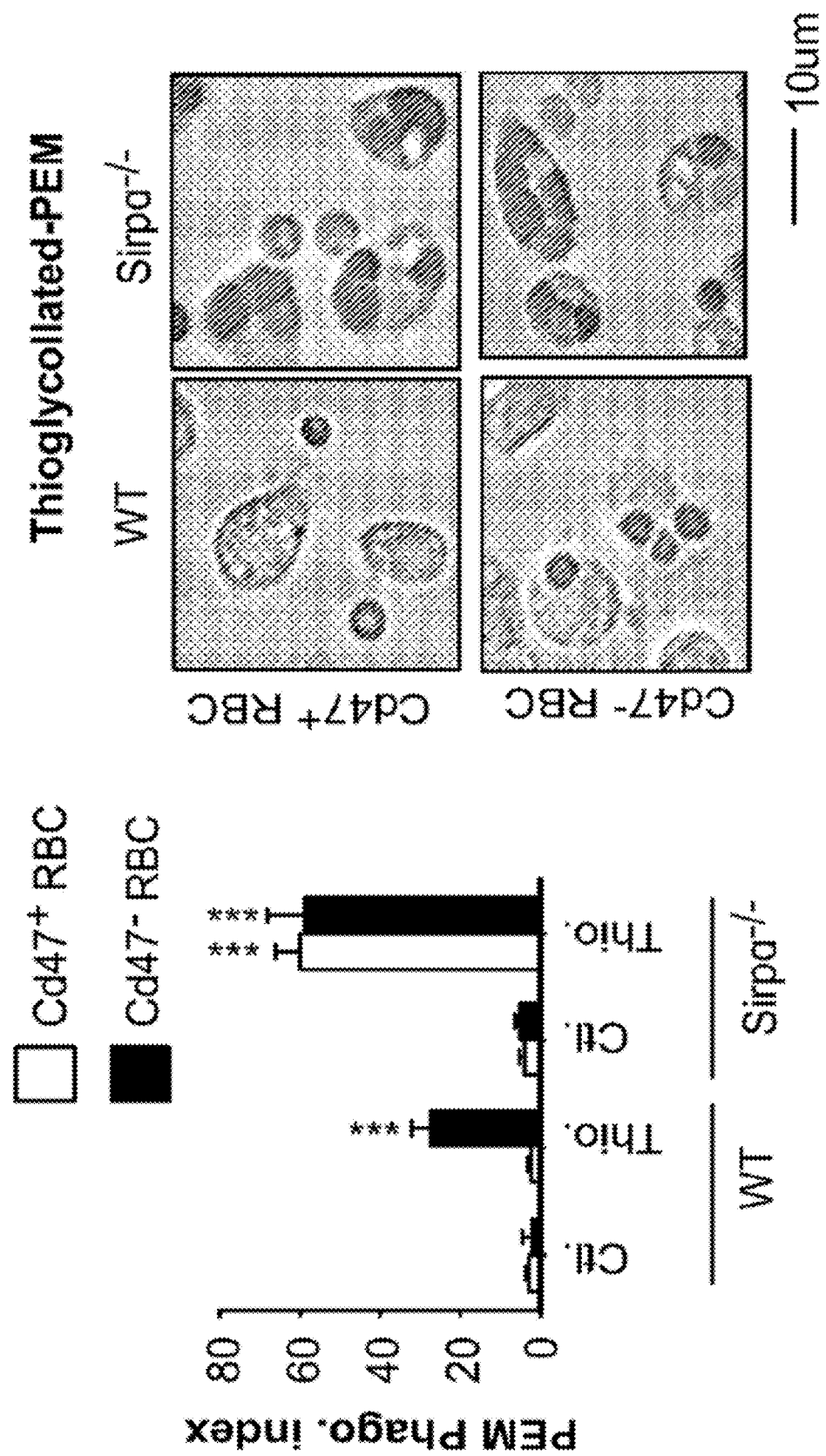
Figure 4A:
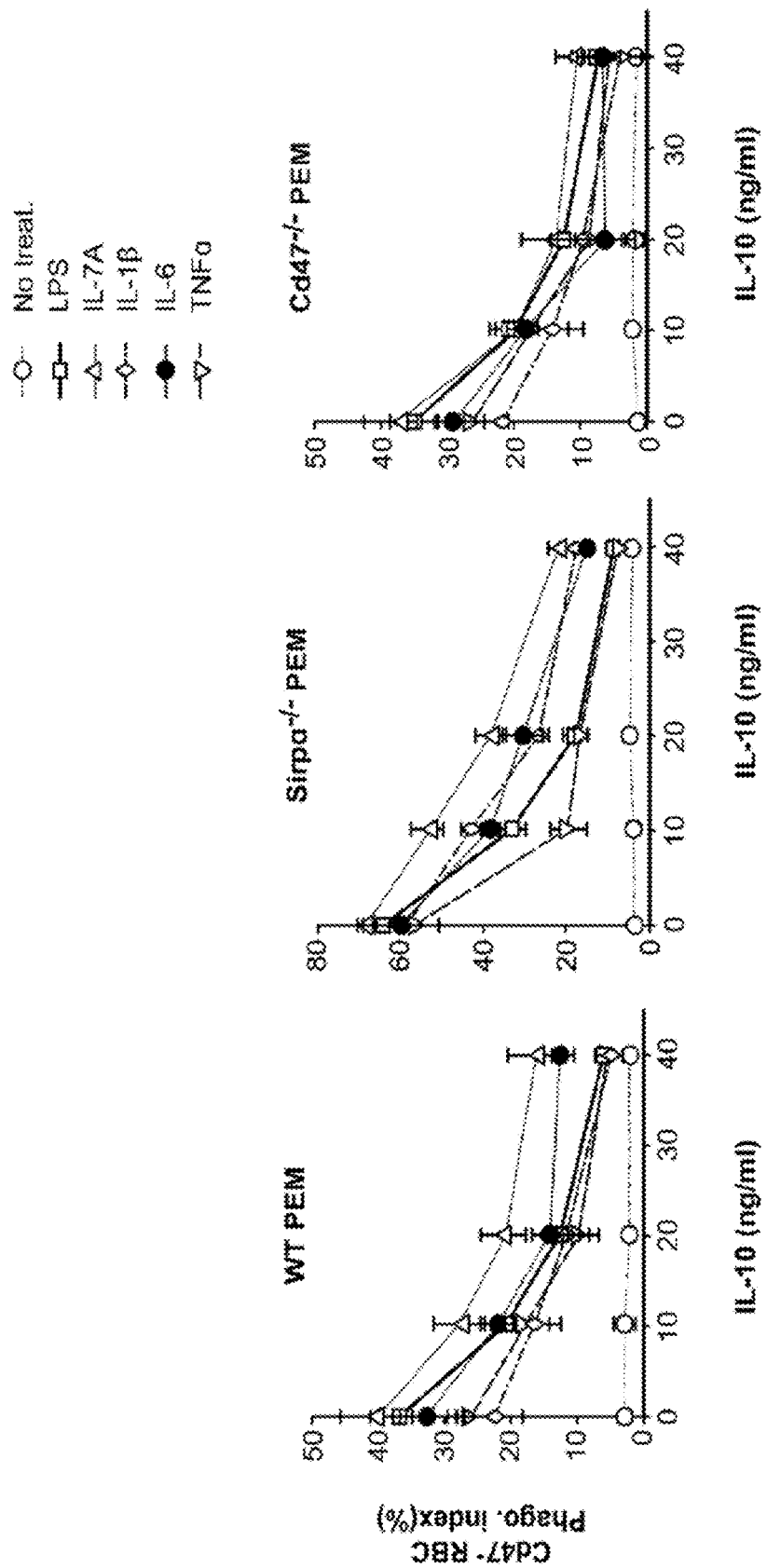
FIGS. 4A-4E include data related to our experiments on macrophage phagocytic plasticity.
Figure 4B:
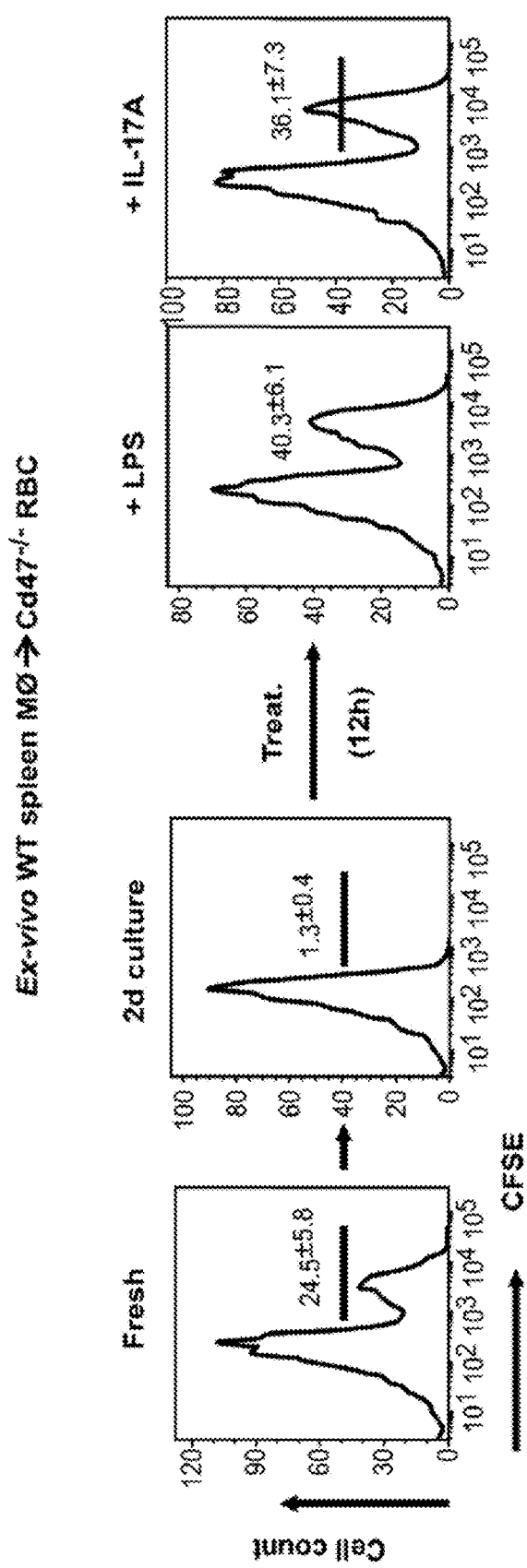
Figure 4C:
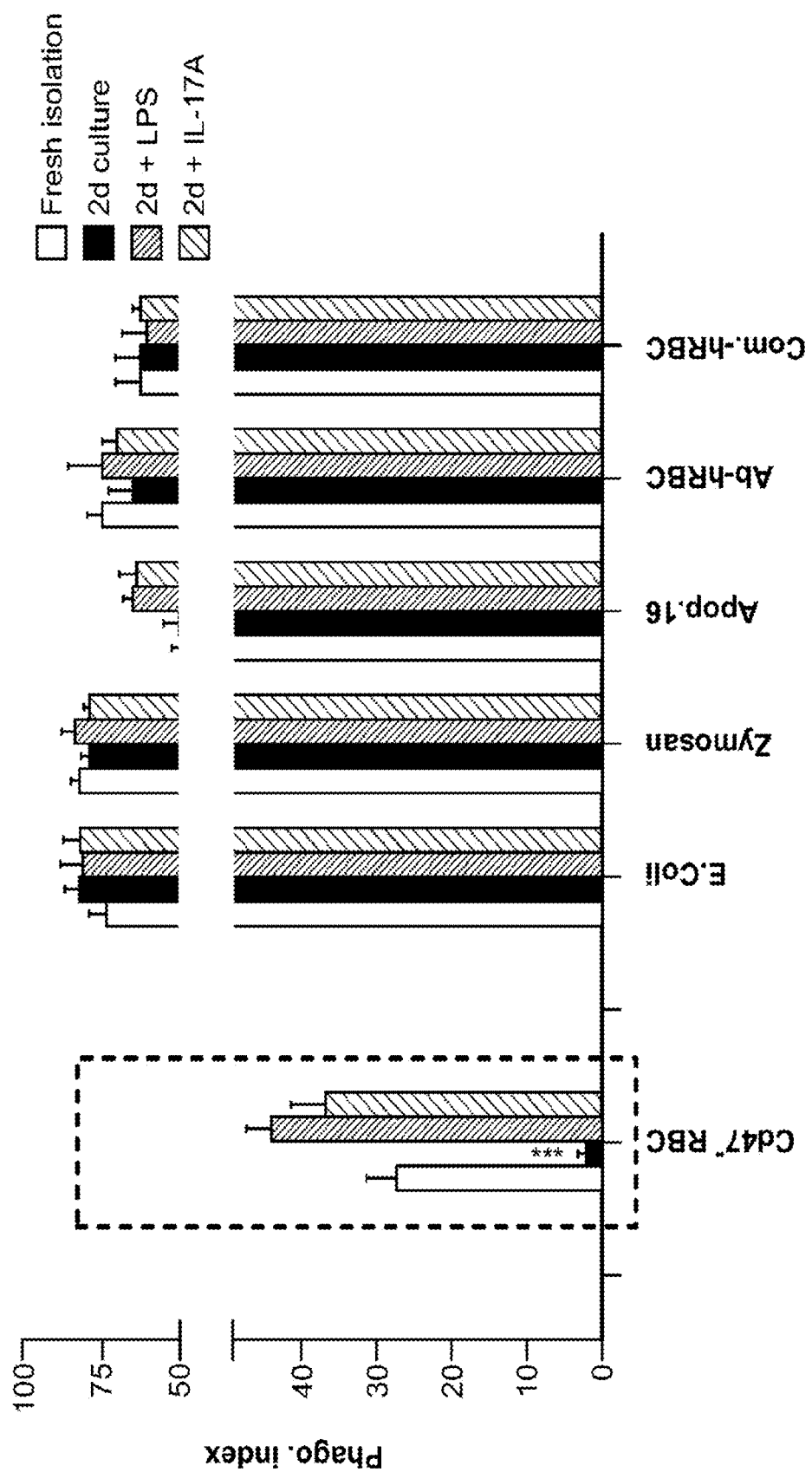

Despite that most macrophages, with the exception of WT red pulp macrophages, displayed no ability to directly phagocytize self-cells, treating these macrophages with LPS or IL-17 dramatically changed their phagocytic behavior. As shown in FIG. 3D, treating splenic macrophages from SIRPα⁻ᐟ⁻ or CD47⁻ᐟ⁻ mice with LPS or IL-17 rapidly induced their phagocytosis toward RBCs. The same treatments also converted all PEMs and BMDMs, including those previously incapable of phagocytosis from WT and mutant mice, to potent phagocytestoward self (FIG. 3E). Strikingly, in all cases, whether phagocytosis occurred was governed by the presence of CD47-SIRPα-mediated inhibition. As shown, the treated SIRPα⁺ macrophages, either from WT mice or CD47⁻ᐟ⁻ mice, phagocytosed only CD47⁻ RBCs, whereas SIRPα⁻ macrophages from SIRPα⁻ᐟ⁻ mice phagocytosed both CD47⁺ RBCs and CD47⁻ RBCs indiscriminately. Through further testing with additional cytokines, we found that IL-6, TNFα, and IL-1β, but not IFNγ, have the ability to induce macrophage phagocytosis toward self, providing a lack of the CD47-SIRPα-mediated inhibition (FIG. 3E). By testing different cell types as the phagocytic targets, we found that macrophages activated by LPS or cytokines were also capable of phagocytizing murine splenocytes, B16 melanoma cells, and EL4 lymphoblasts in a CD47-SIRPα-controllable manner (FIGS. 3F and 3G) and human RBCs and human HT29 colonic epithelial cells on which the expressed CD47 was incompatible for murine SIRPα. Moreover, and referring to FIG. 3H, we found that thioglycollate, a reagent commonly used to elicit macrophages in the peritoneum, activates PEM phagocytosis toward RBCs, explaining the seemingly discrepant results reported by others (Yamao et al., *J. Biol. Chem.* 277 (42): 39833-39839, 2002). Converse to phagocytic activation, IL-10 strongly inhibits macrophage phagocytosis. As shown in FIG. 4A, IL-10 dose-dependently inhibited LPS-, IL-17-, IL-6-, TNFα-, and IL-1β-induced activation of PEM phagocytosis toward RBCs. Interestingly, WT red pulp macrophages also displayed remarkable phagocytic plasticity ex vivo. As shown in FIG. 4B, these macrophages, which directly phagocytized CD47⁻ RBCs immediately following isolation, completely lost this capacity after 2 days of culturing, but maintained phagocytosis toward *E. coli*, zymosan, apoptotic cells, and antibody- or complement-bound targets (FIG. 4C). To test whether these macrophages could be revived to target RBCs, we treated them with LPS and IL-17, which dramatically rekindled the "culture-retarded" WT spleen macrophages for potent phagocytosis toward CD47⁻ RBCs. Again, this rejuvenated phagocytosis was subject to the control of the CD47-SIRPα mechanism, as it completely avoided CD47⁺ RBCs.

Figure 4D:
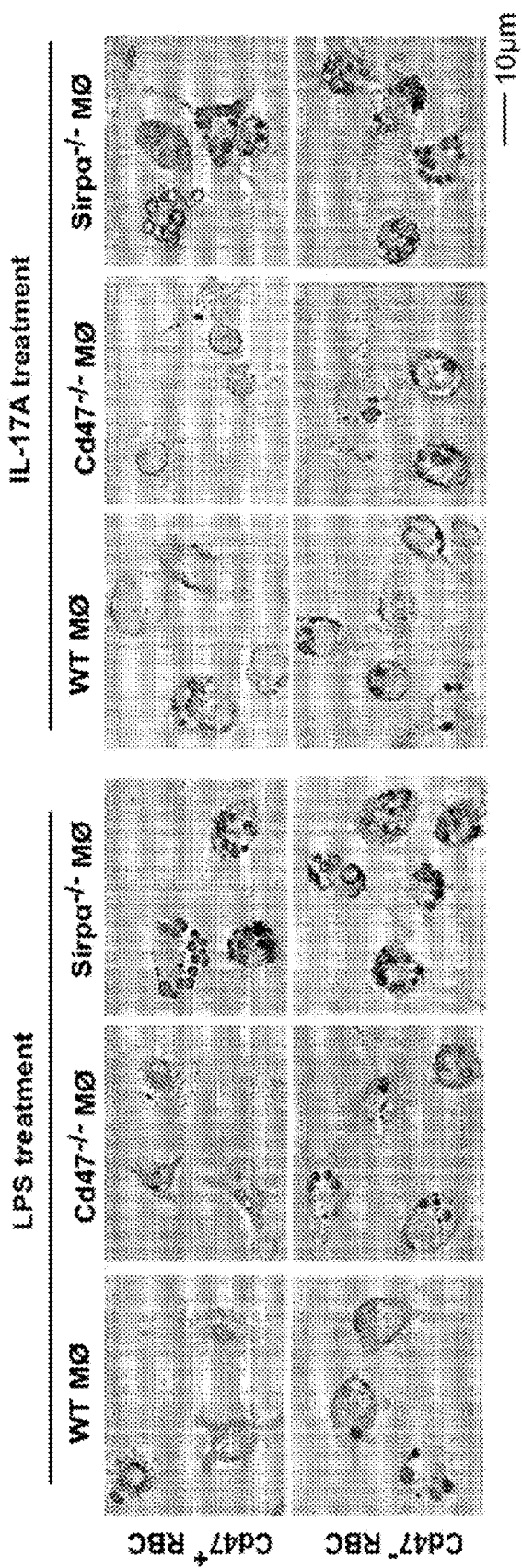
Figure 4E:
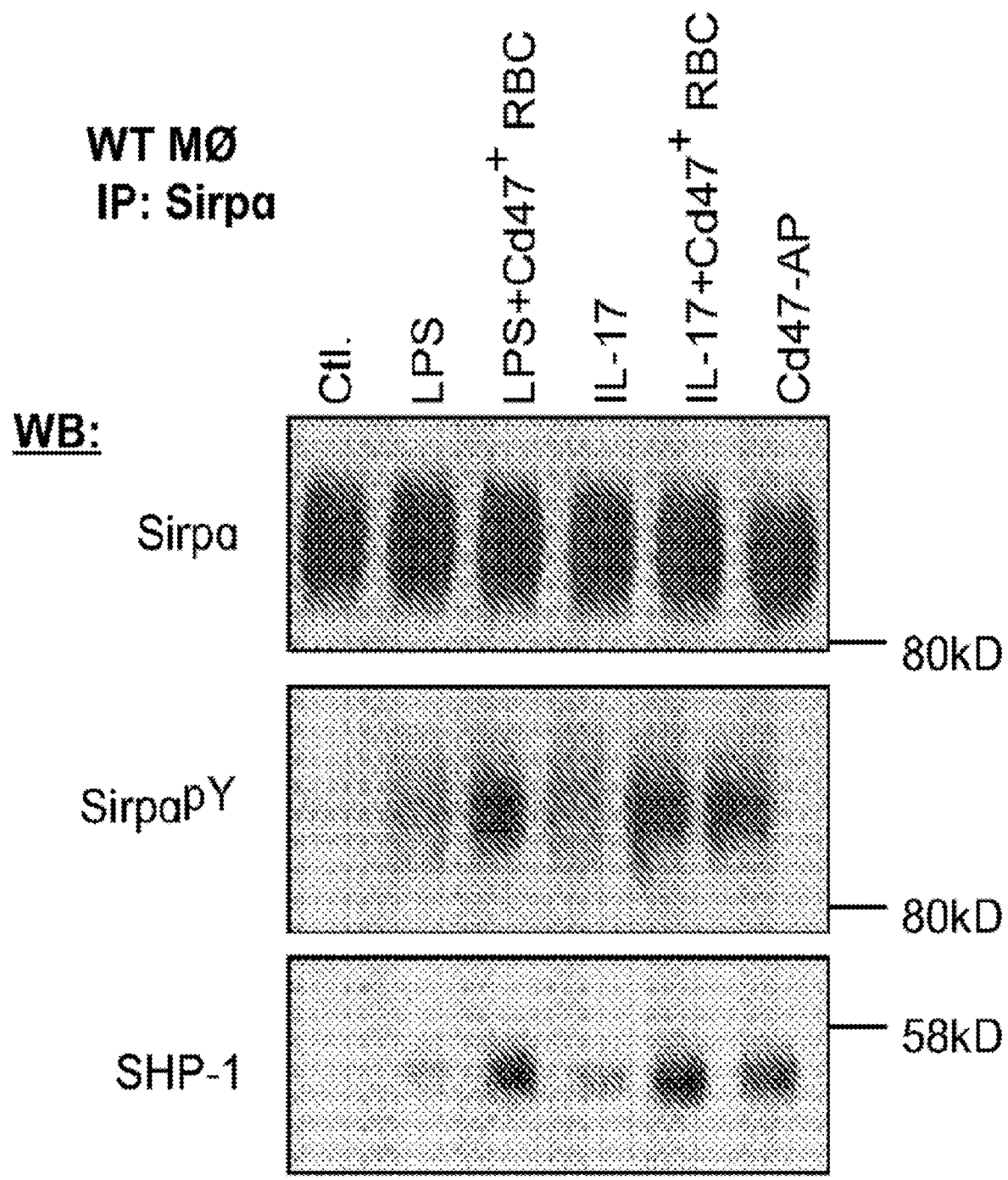

Moreover, the expression of SIRPα alone appears to convey inhibition in phagocytosis. As shown in FIG. 4D, as well as other figures, LPS/cytokine-treated SIRPα⁻ macrophages consistently displayed much more potent phagocytosis toward self-cells than the same-treated WT macrophages. Real-time recording showed that the treated SIRPα⁻ PEMs displayed an extraordinary capability to grab and uptake RBCs, resulting in rapid phagocytosis of multiple RBCs in a short time period, during which the same-treated WT PEMs phagocytized only one to two RBCs (data not shown). Analysis of SIRPα in WT macrophages after LPS or IL-17 treatment revealed a level of SIRPα ITIM phosphorylation and SHP-1 association even in the absence of extracellular CD47 ligation; however, cell surface ligation by CD47⁺ RBCs led to further increased SIRPα ITIM phosphorylation and SHP-1 association (FIG. 4E). SIRPα expression alone conveys partial inhibition, whereas stronger inhibitory signaling triggered by CD47 ligation is needed for effectively blocking macrophage phagocytosis toward self.

Example 6. Signaling Mechanisms Regulating Macrophage Phagocytosis Toward Self

Figure 5A:
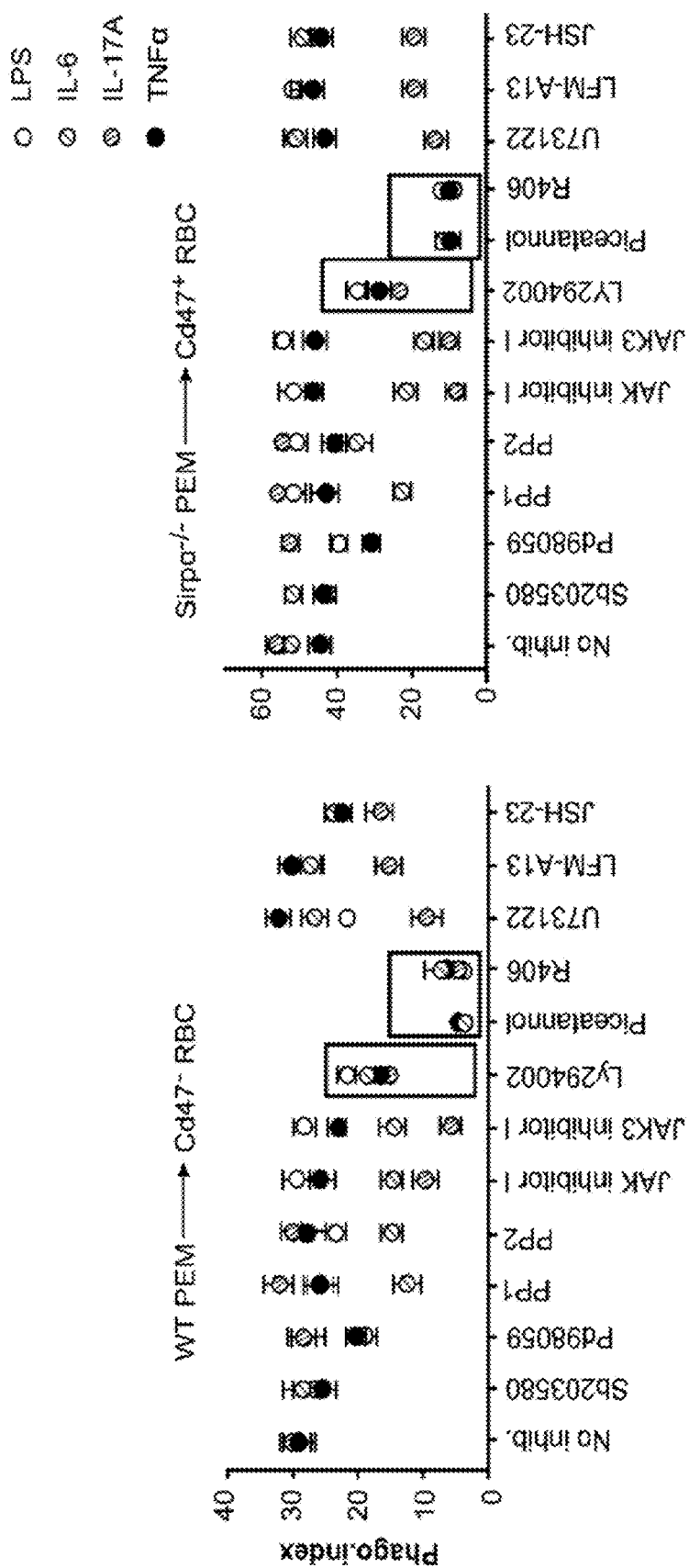
FIGS. 5A-5H include data related to our experiments on the role of Syk in phagocytic activation.
Figure 5B:
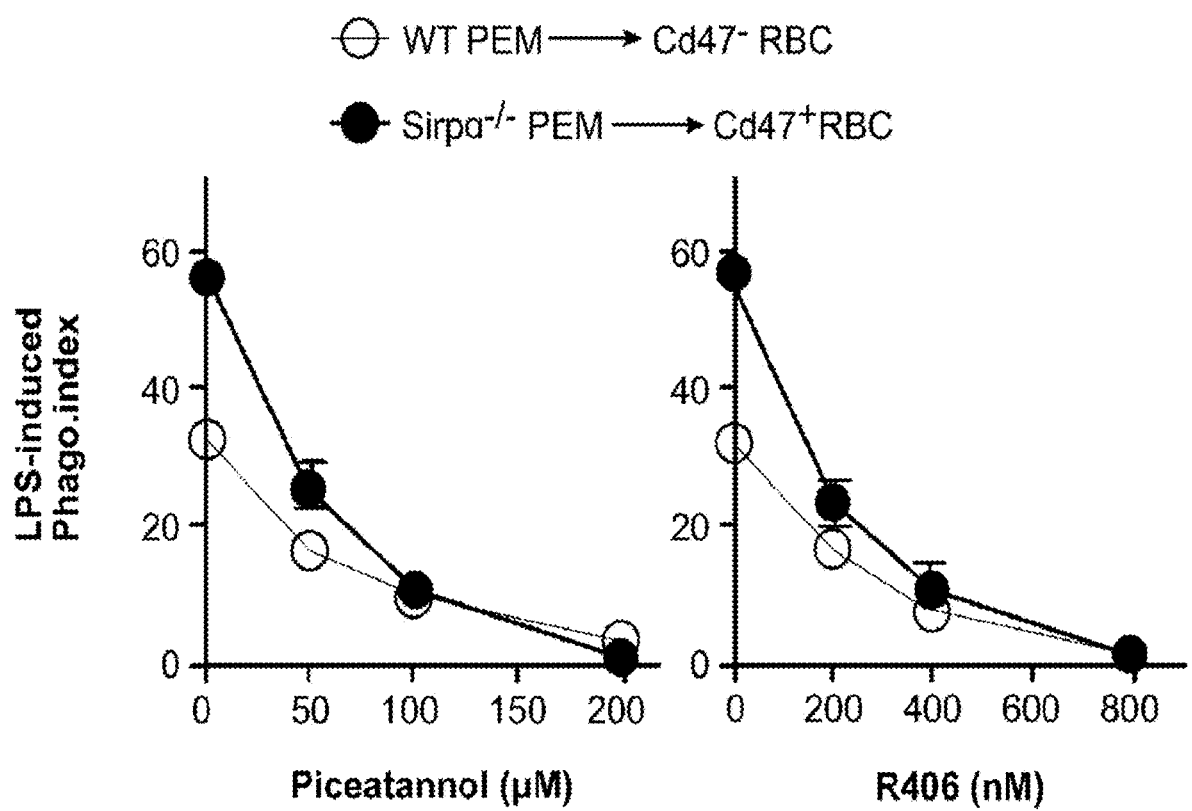
Figure 5C:
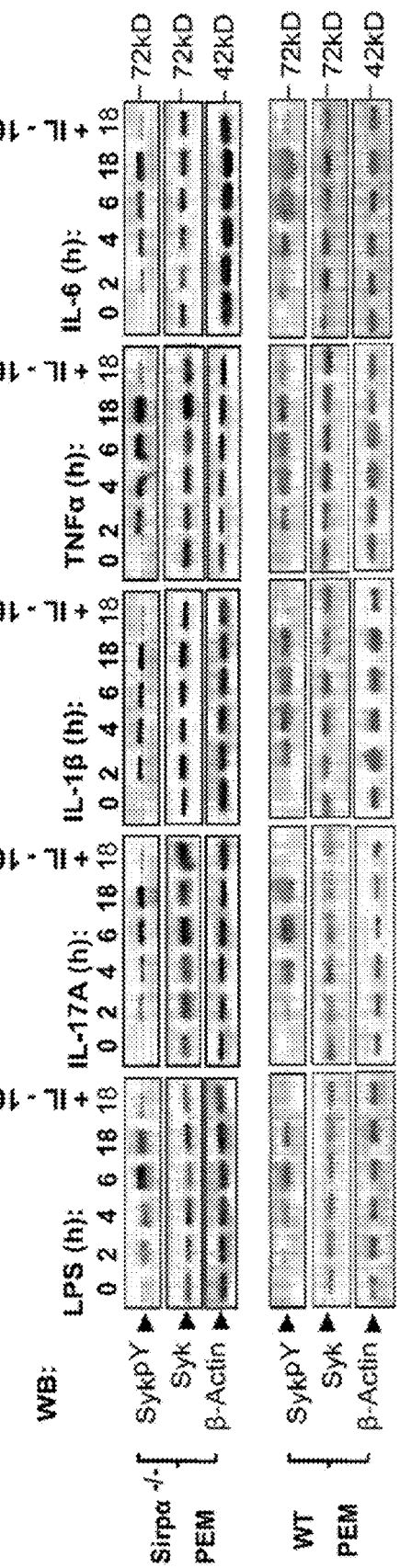

Multiple pharmacological inhibitors were tested for their effects on LPS and cytokine-induced activation of macrophage phagocytosis toward self. As shown in FIG. 5A, treating macrophages with inhibitors against MAP kinases, p38 (SB203580) and MEK (PD98059); Src family tyrosine kinases, PP1 and PP2; JAK 1 (JAK inhibitor I); JAK3 (JAK3 inhibitor I); PLC (U73122); Btk (LFM-13); or NF-κB (JSH-23) diminished phagocytic activation induced by certain, but not all stimuli. For example, inhibition of JAKs blocked IL-6 and IL-17, but not LPS and TNFα, for activation of PEM phagocytosis. These results were comprehensible; different stimuli trigger distinctive downstream molecules, especially at the proximal signaling region. In comparison, inhibition of PI3K by LY294002 and inhibition of Syk by Piceatannol or R406 inhibited phagocytic activation by all stimuli. As shown, LY294002 (20 μM) partially inhibited PEM phagocytic activation, whereas Syk inhibitors piceatannol (100 μM) and R406 (400 nM) nearly completely eliminated PEM activation induced by all stimuli. FIG. 5B shows piceatannol and R406 dose-dependently inhibited LPS-induced activation of PEM phagocytosis toward RBC. As shown in FIG. 5C, testing Syk kinase activity by the phosphorylation at Y519/520 (Syk$^{PY}$) in PEMs found increases in Syk$^{PY}$ (thus Syk activity) after LPS/cytokine stimulation, supporting a key role of Syk in macrophage phagocytic activation. Conversely, IL-10, the phagocytic suppressive cytokine, counter-repressed Syk phosphorylation induced by activation factors. Although Syk was suggested to activate myosin-II (Tsai et al., *J. Cell. Biol.* 180 (5):989-1003, 2008), this appeared to not be the case in macrophage phagocytic activation; however, myosin-II was required for the later phagocytosis process in a way similar as in Fc-mediated phagocytosis (Tsai et al., *J. Cell. Biol.* 180 (5):989-1003, 2008; Vicente-Manzanares et al., *Nat. Rev. Mol. Cell. Biol.* 10 (11): 778-790, 2009). Depletion of calcium and magnesium or the presence of EDTA hindered macrophage phagocytic activation, possibly through affecting macrophage adhesion or the activation of the specific phagocytic receptor.

Figures 5D, 5E:
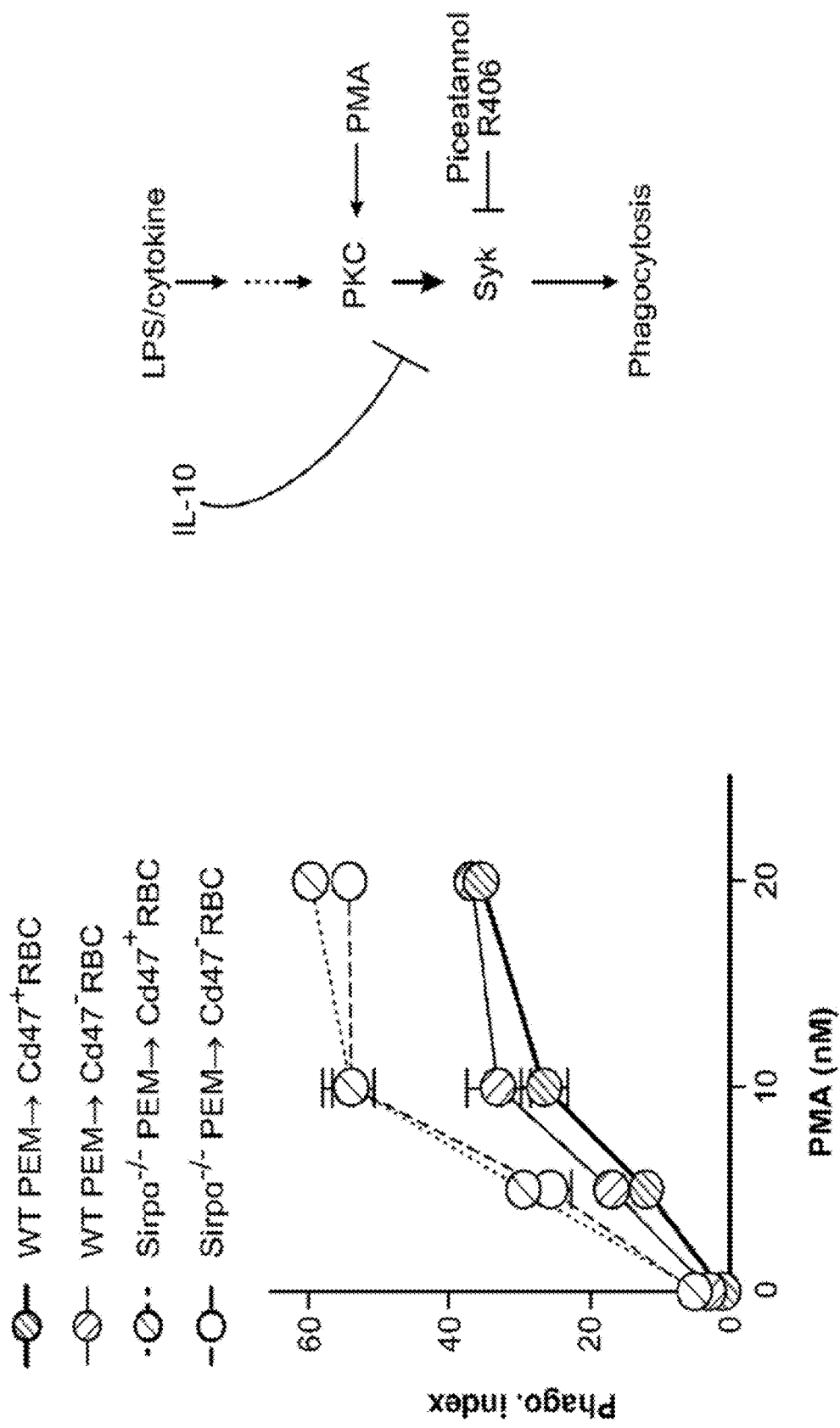
Figure 5F:
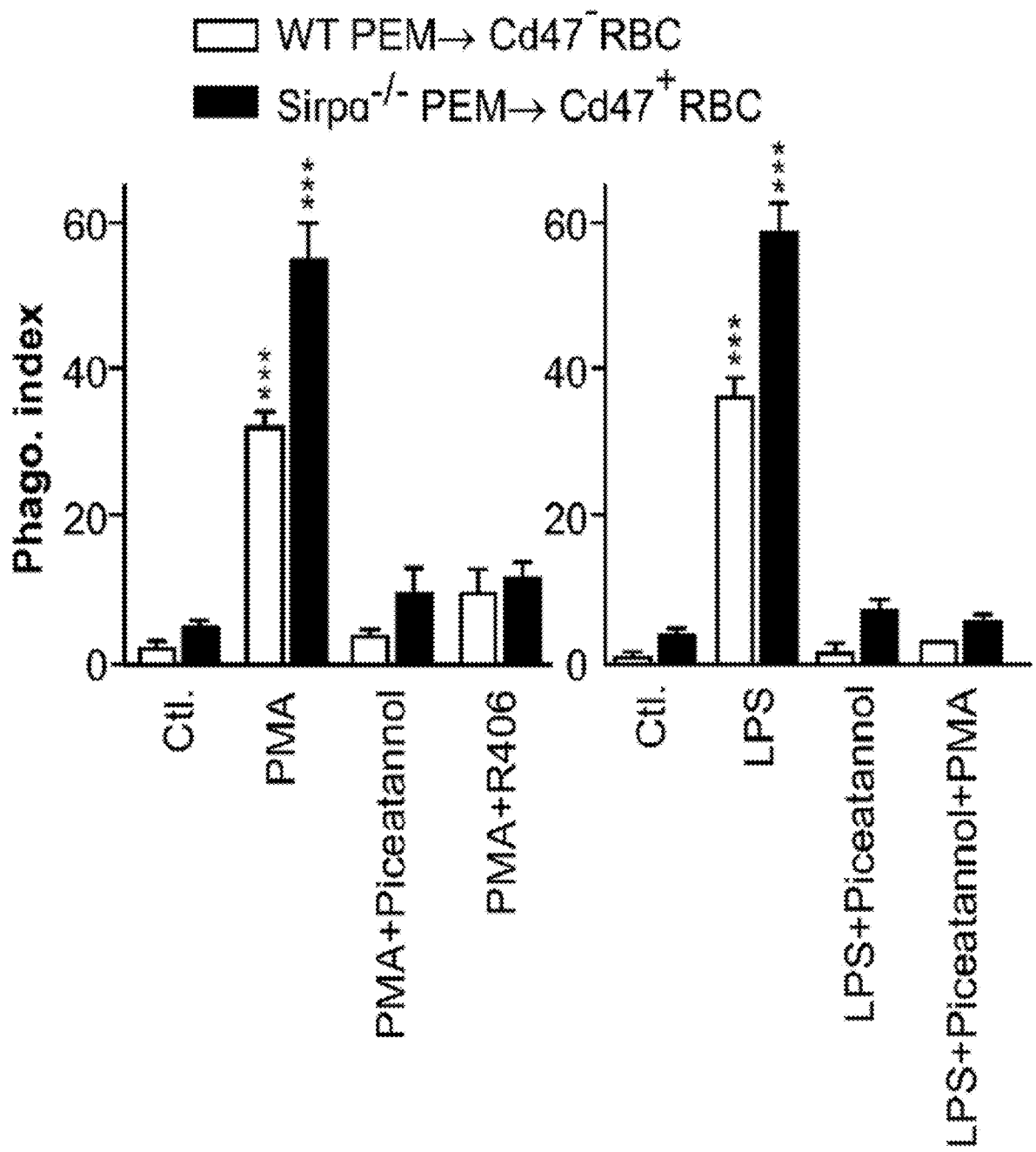
Figure 5G:
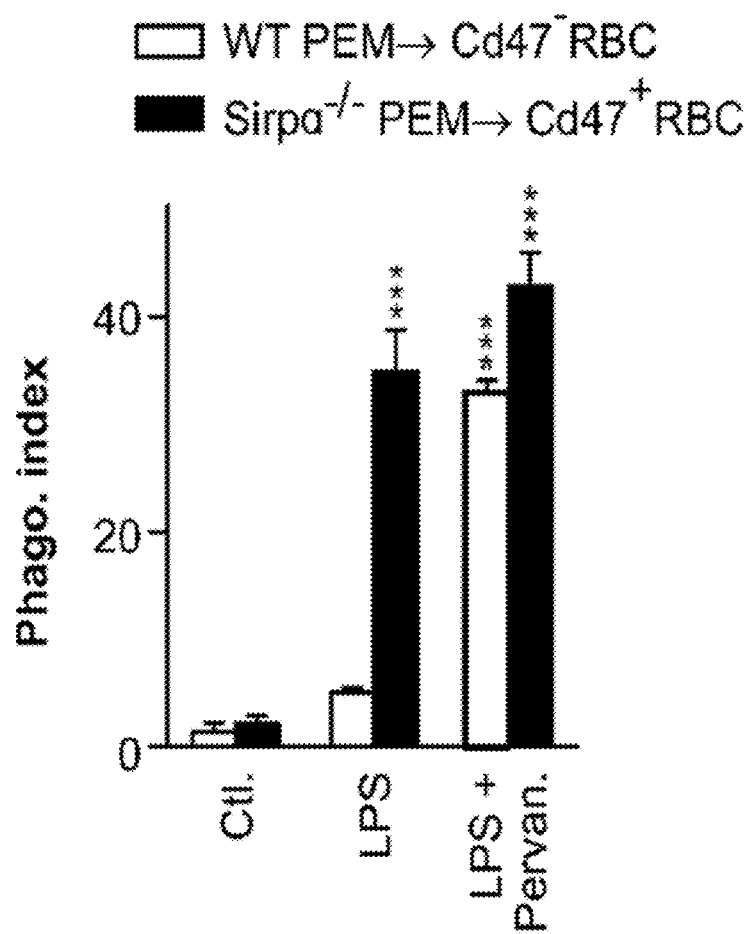
Figure 5H:
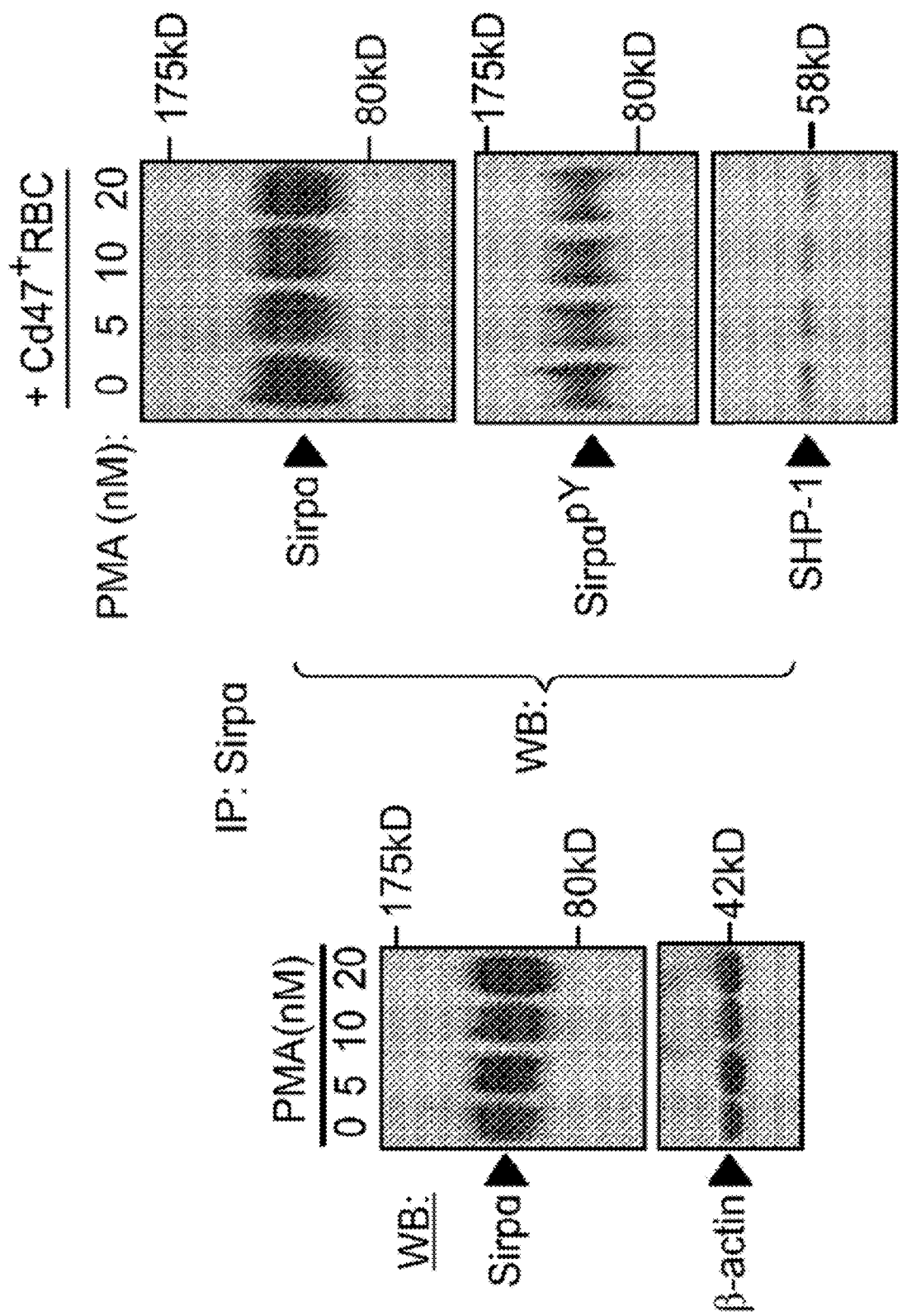

Moreover, we found that PMA, the PKC activator, dramatically activates macrophages for phagocytosis toward self. As shown in FIG. 5D, even at low nanomolar concentrations, PMA treatment instantly initiated PEM to phagocytose RBCs. In addition, PKC appears to be upstream of Syk in the phagocytic activation pathway (FIG. 5E). Inhibition of Syk by Piceatannol and R406 eliminated the PMA-induced PEM phagocytosis, whereas PMA treatment failed to rescue Syk inhibition-repressed PEM phagocytic activation by LPS (FIG. 5F). That PKC induces Syk activation in macrophages was consistent with previous reports (40-42). Interestingly, PMA-induced phagocytosis disregards the CD47-SIRPα-mediated inhibition. As shown, PMA-treated WT PEMs aggressively phagocytosed both CD47⁻ and CD47⁺ RBCs, a target indiscrimination similar to macrophages treated by pervanadate to abolish SHP signaling (FIG. 5G). Because PMA treatment neither reduced SIRPα expression nor affected SIRPα ITIM phosphorylation and SHP-1 association (FIG. 5H), this effect of PMA suggests an interference of the signaling pathway downstream of the SIRPα-ITIM-SHP axis.

Figure 6B:
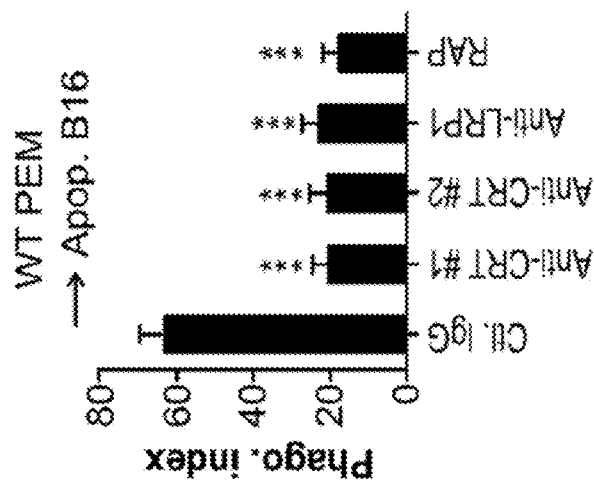
FIGS. 6A-6D include data related to our investigation of possible phagocytic receptors on macrophages for phagocytosing healthy self-cells.
Figure 6A:
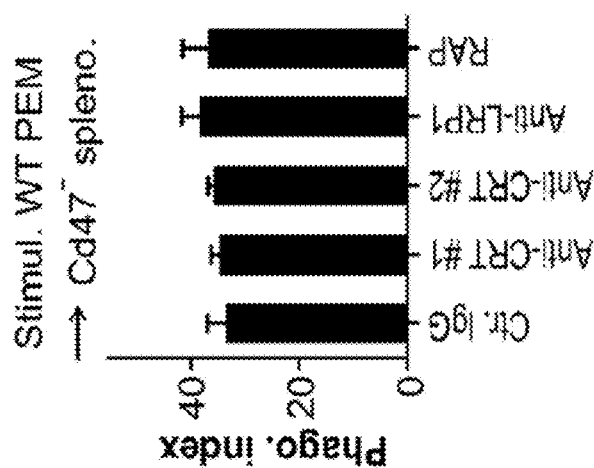
Figure 6A:
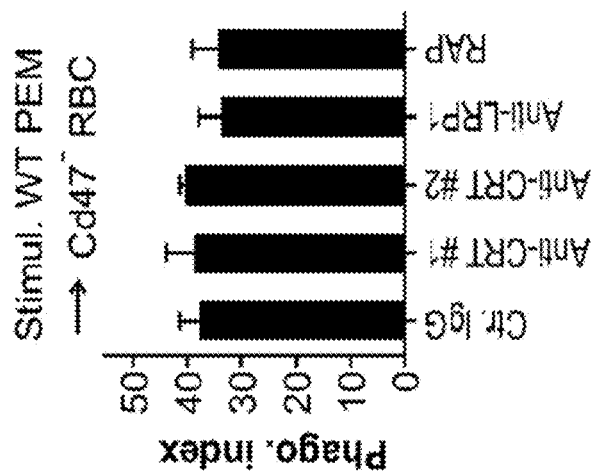
Figure 6C:
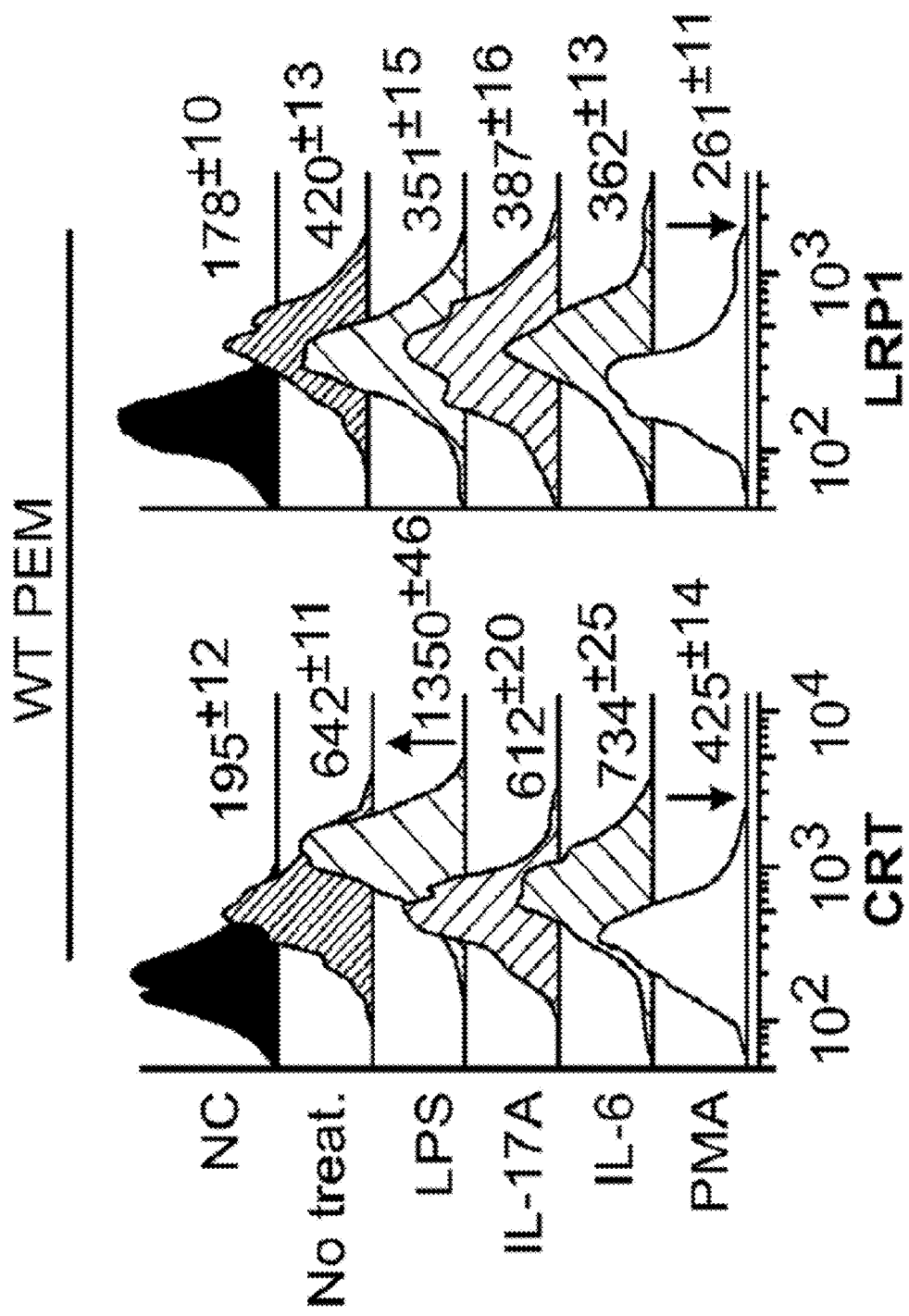

Example 7. Investigating a Possible Phagocytic Receptor on Macrophages for Uptaking Healthy Self-Cells Given that calreticulin (CRT) interaction with LDL receptor-related protein (LRP1) has been suggested to mediate phagocytosis of apoptotic cells and viable cells (Gardai et al., *Cell* 123 (2):321-334, 2005; Chao et al., *Sci. Transl. Med.* 2 (63):63ra94, 2010; Nilsson et al., *Biochem. Biophys. Res. Commun.* 417 (4):1304-1309, 2012), we examined these proteins. As shown in FIG. 6A, neither the inhibitory antibodies against CRT or LRP1 (Feng et al., Proc. Natl. Acad. Sci. USA 112 (7):2145-2150, 2015) nor LRP1 receptor associated protein (RAP), which inhibits CRT-LRP1 binding (Gardai et al., Cell 123 (2):321-334, 2005; Medh et al., J. Biol. Chem. 270 (2):536-540, 1995; Williams et al., J. Biol. Chem. 267 (13):9035-9040, 1992), showed inhibition on LPS/cytokine-activated PEM phagocytosis toward RBCs and splenocytes. However, these same reagents significantly inhibited phagocytosis toward apoptotic cells (FIG. 6B). Although a previous study (Feng et al., Proc. Natl. Acad. Sci. USA 112 (7):2145-2150, 2015) had suggested that increase of CRT on the macrophage surface is associated with phagocytosis toward tumor cells, assessment of CRT and LRP1 levels on PEMs found no convincing correlation of these protein expressions with PEM phagocytic activation. As shown in FIG. 6C, except for that LPS treatment induced an increase in CRT (consistent with Feng et al., Proc. Natl. Acad. Sci. USA 112 (7):2145-2150, 2015), none of the other phagocytic activation factors induced elevation of CRT or LRP1 on PEMs. Conversely, CRT and LRP1 expression on PEMs were even reduced (~50%) after PMA treatment, which potently activates phagocytosis/macrophages toward self. Protein coimmunoprecipitation also failed to detect alteration of CRT-LRP1 association, or LRP1 tyrosine phosphorylation, in PEMs after phagocytic activation, thus ruling out LRP1 to be a direct target downstream of Syk. Collectively, these results suggest that CRT and LRP1 are unlikely to be the receptor-ligand pair that is activated by phagocytic stimuli and mediates phagocytosis toward healthy self-cells.

Figure 6D:
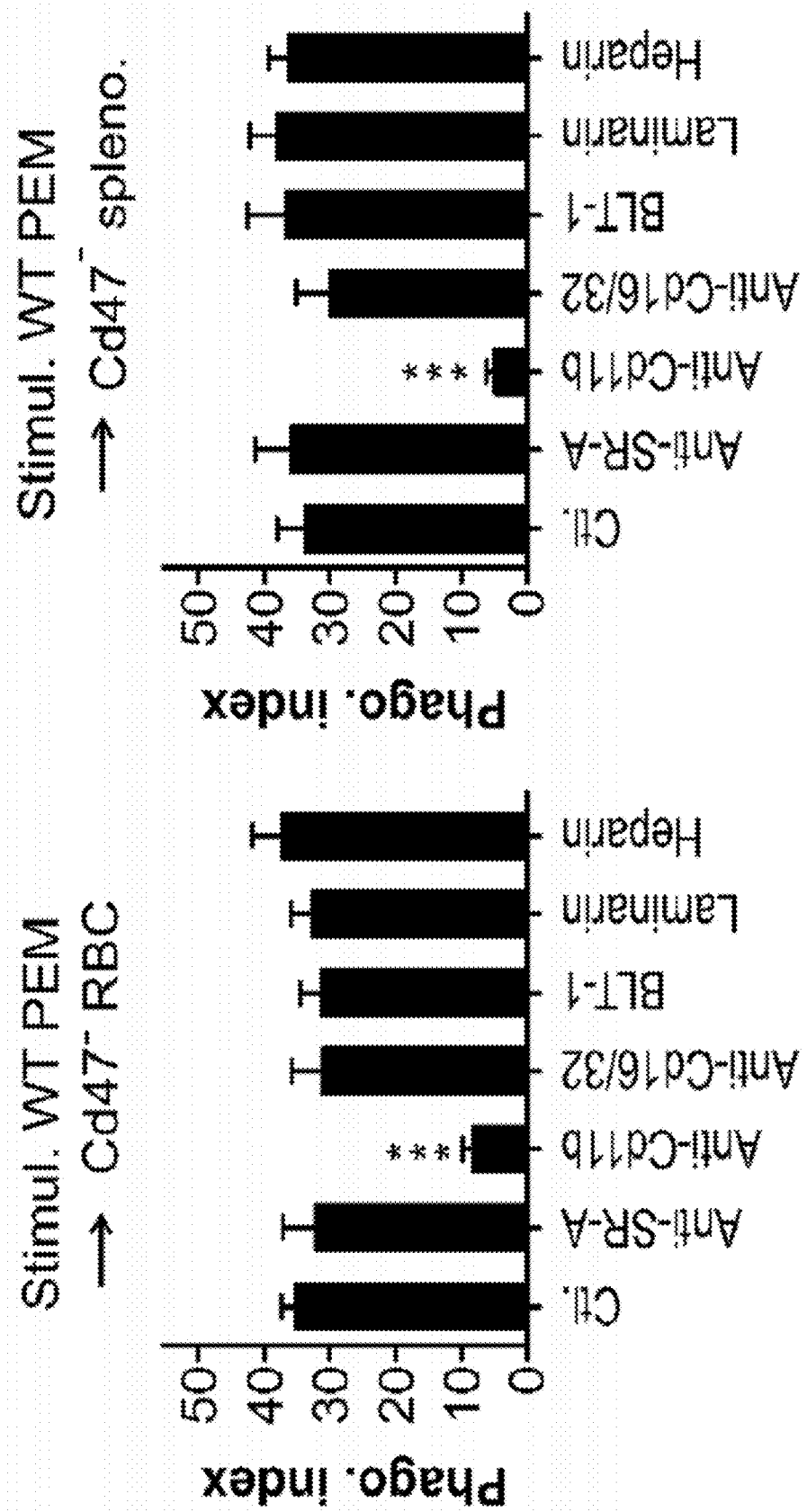

We also tested other known phagocytic receptors for their roles in activated macrophage phagocytosis toward self. As shown in FIG. 6D, antibody inhibition of scavenger receptor A (anti-SR-A) 847 or Fc receptors (anti-CD16/CD32) (Mosser et al., Current Protocols in Immunology, 2011), or inhibitors against scavenger receptor B (BLT1) (Nieland et al., Proc. Natl. Acad. Sci. USA 99 (24):15422-15427, 2002), dectin (laminarin) (Herre et al., Blood 104 (13):4038-4045, 2004), and complement (heparin) (Lappegård et al., Ann. Thorac. Surg. 77 (3): 932-941, 2004) mediated phagocytosis, failed to affect LPS-induced PEM phagocytosis toward RBCs. Interestingly, antibody against integrin Cd11b (Cd11b/Cd18) impeded phagocytosis. It is possible that anti-CD11b antibody affected macrophage adhesion and membrane spreading, through which inhibited phagocytosis toward RBCs. The role of CD11b in phagocytosis of RBCs has also been reported for dendritic cells (Yi et al., Immunity 43 (4):764-775, 2015).

Example 8. Different Spleen Environments in WT Mice and Mutant Mice

Figure 7A:
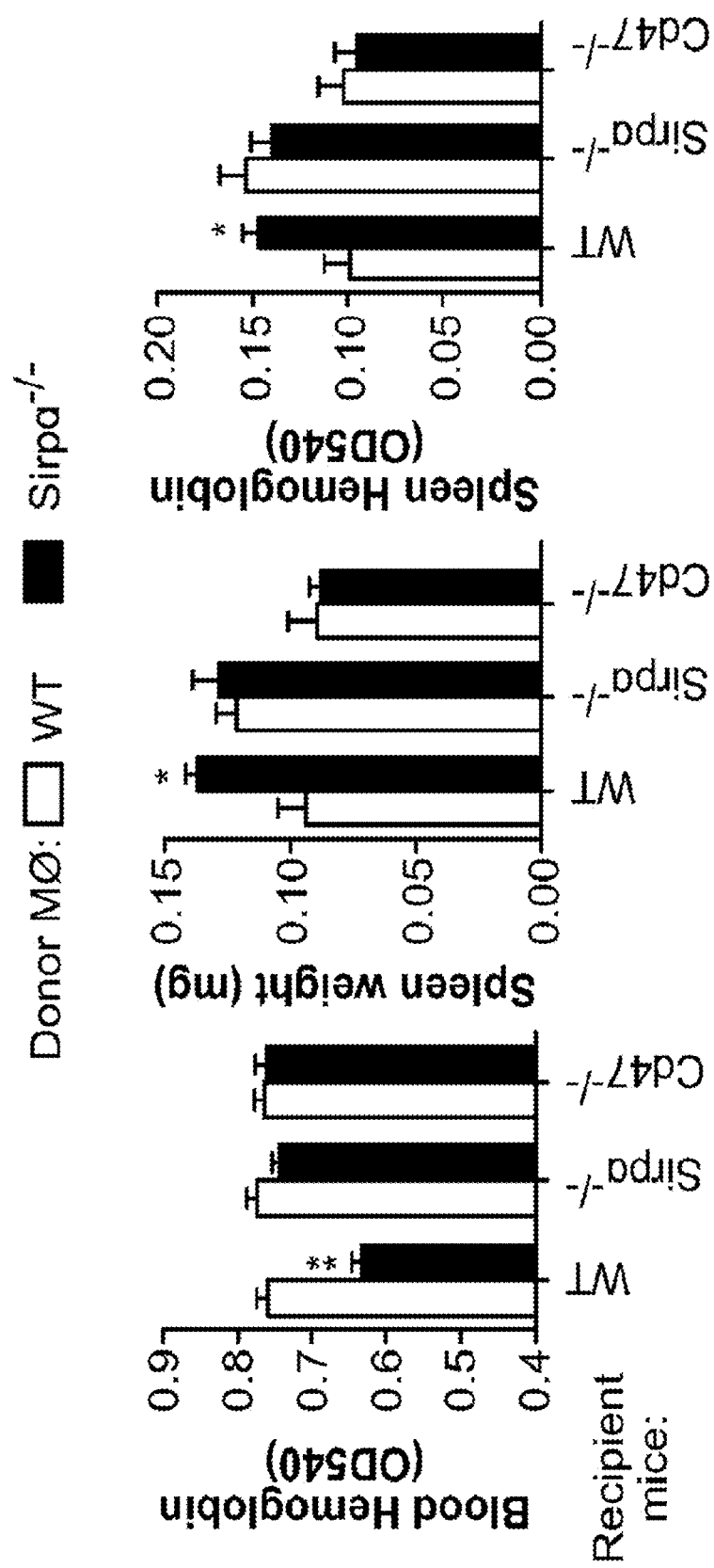
FIGS. 7A-7H include data related to our finding that SIRPα$^{-/-}$ or Cd47$^{-/-}$ mice, but not WT mice, are deficient of macrophage stimulation in the spleen.
Figure 7B:
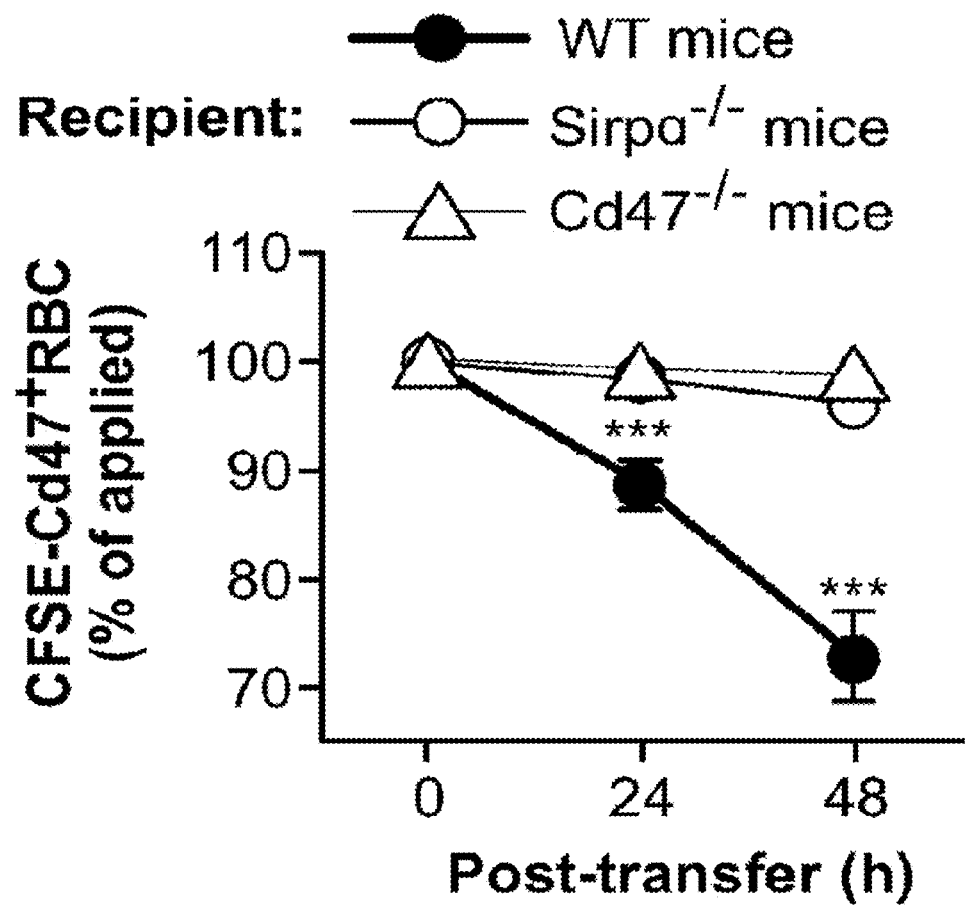
Figure 7C:
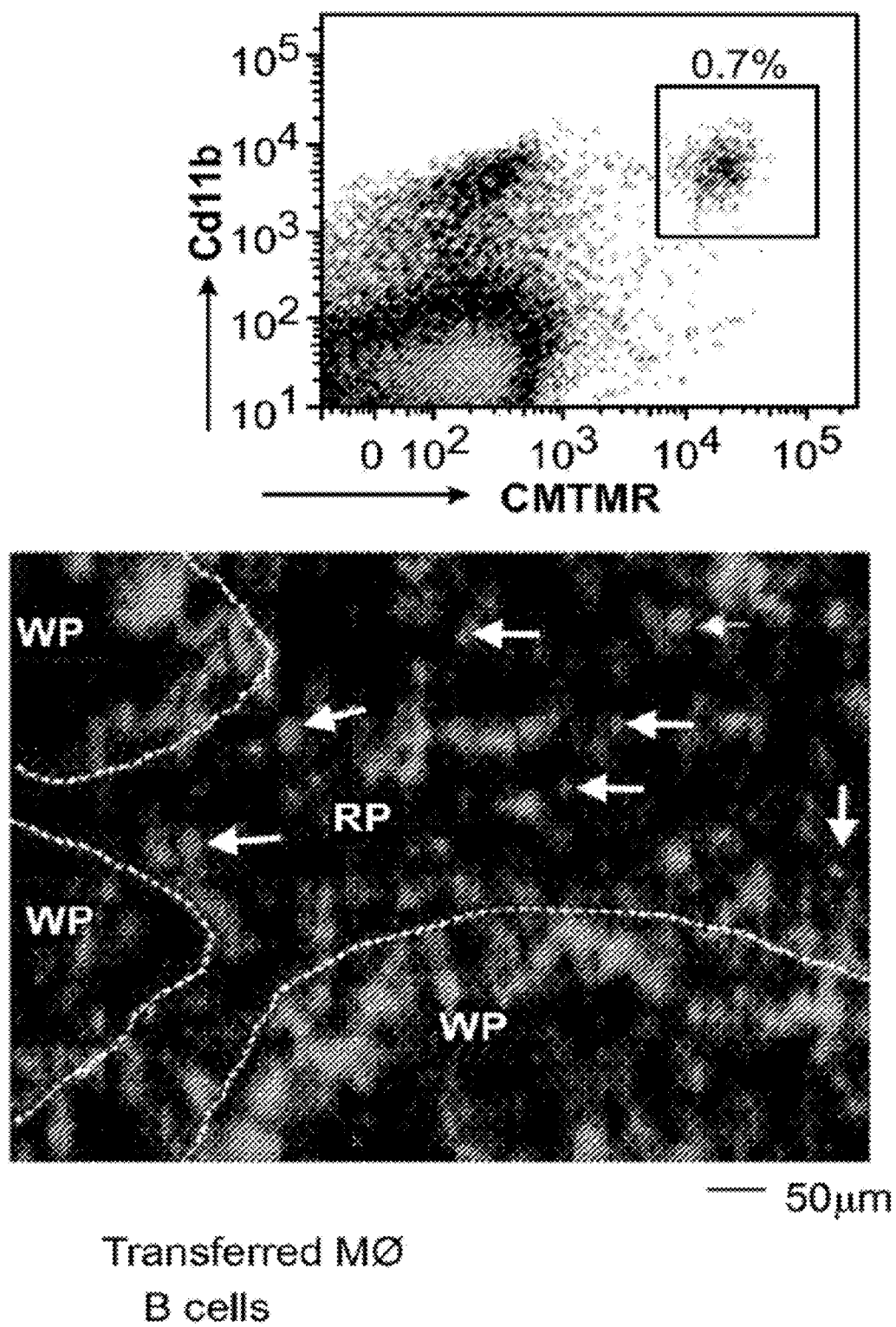

From our data, it is possible that all macrophages are capable of phagocytizing cells (e.g., healthy self-cells); however, initiating that capacity may depend on the presence of activating stimuli. The fact that red pulp macrophages in WT mice, but not SIRPα$^{-/-}$ or CD47$^{-/-}$ mice, directly phagocytize CD47$^-$ RBCs without requiring further activation suggests that the WT spleen provides constant stimulation supporting macrophage phagocytosis toward self, whereas the spleens in mutant mice do not. Our observations that red pulp macrophages isolated from WT mice quickly diminished in phagocytic capacity, which was then rekindled by extrinsic stimuli, support this notion. In addition, adoptive transfer of nonphagocytic SIRPα$^-$ BMDMs into WT mice instantly induced RBC loss (10-30%, 48 hours) and splenomegaly (FIG. 7A). Co-transfer with CSFE-labeled CD47$^+$ RBCs confirmed that SIRPα$^-$ macrophages mediated erythrophagocytosis in WT mice (FIG. 7B). Tissue analyses indicated that the adoptively transferred SIRPα$^-$ macrophages were distributed in red pulp of the WT spleen (FIG. 7C).

Figure 7D:
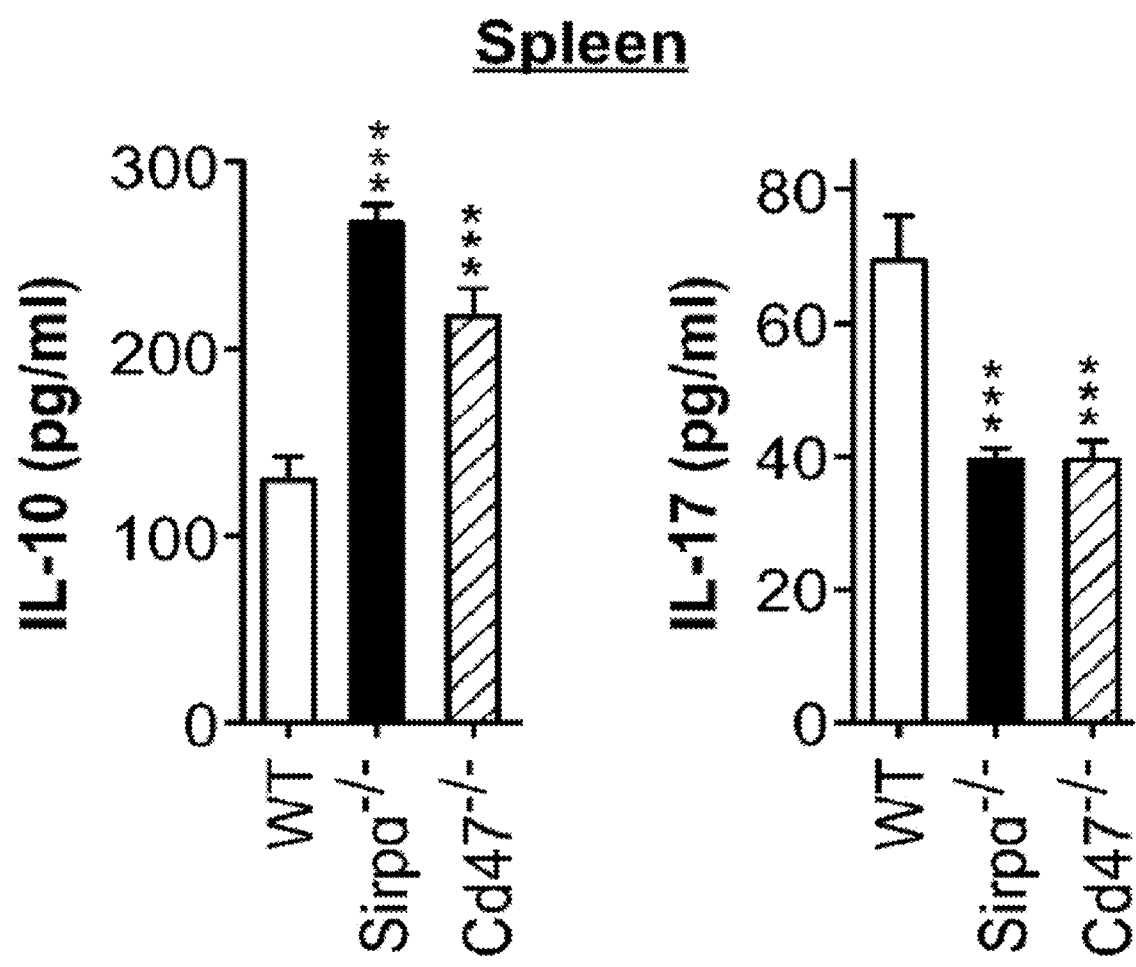
Figure 7E:
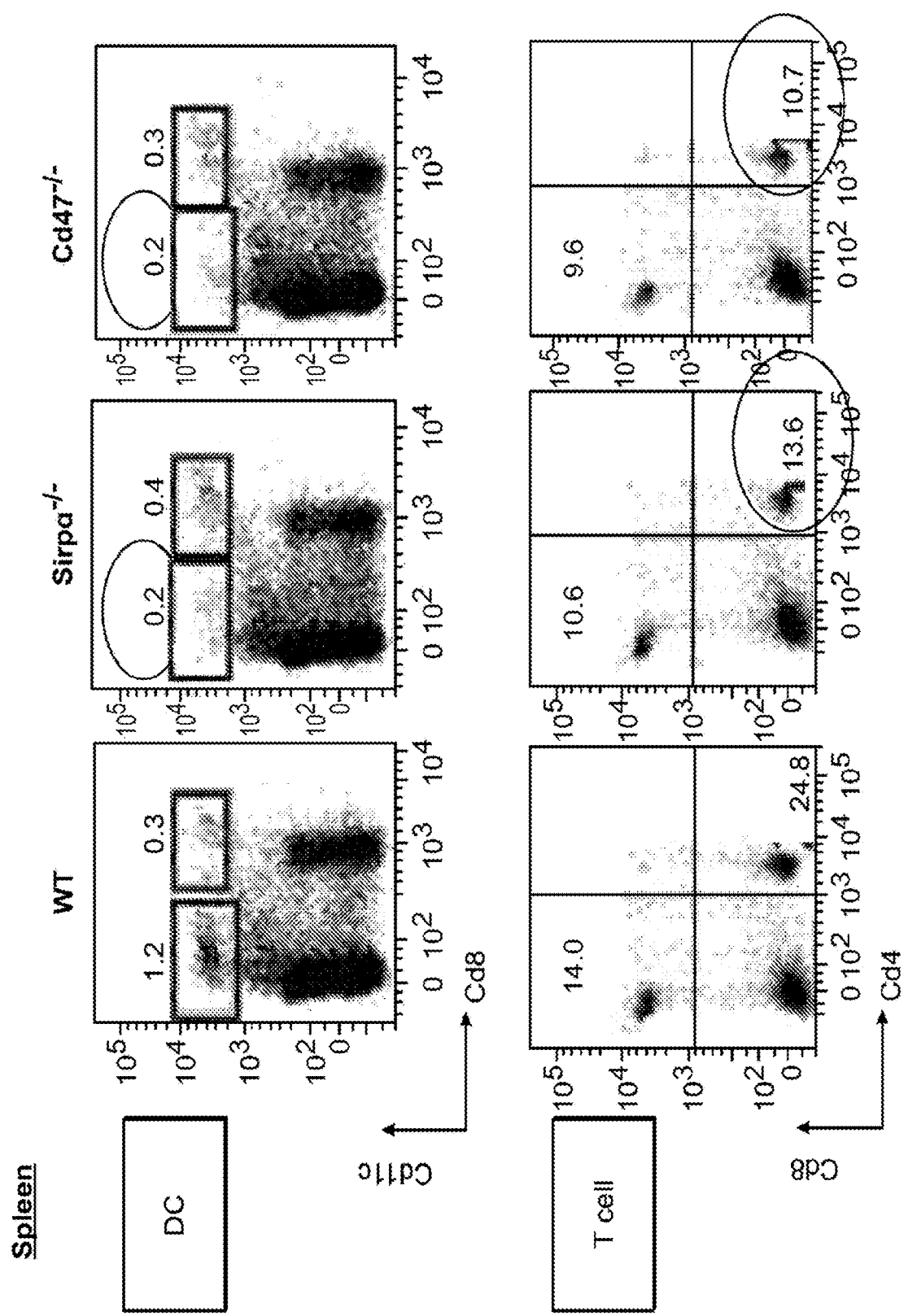
Figure 7F:
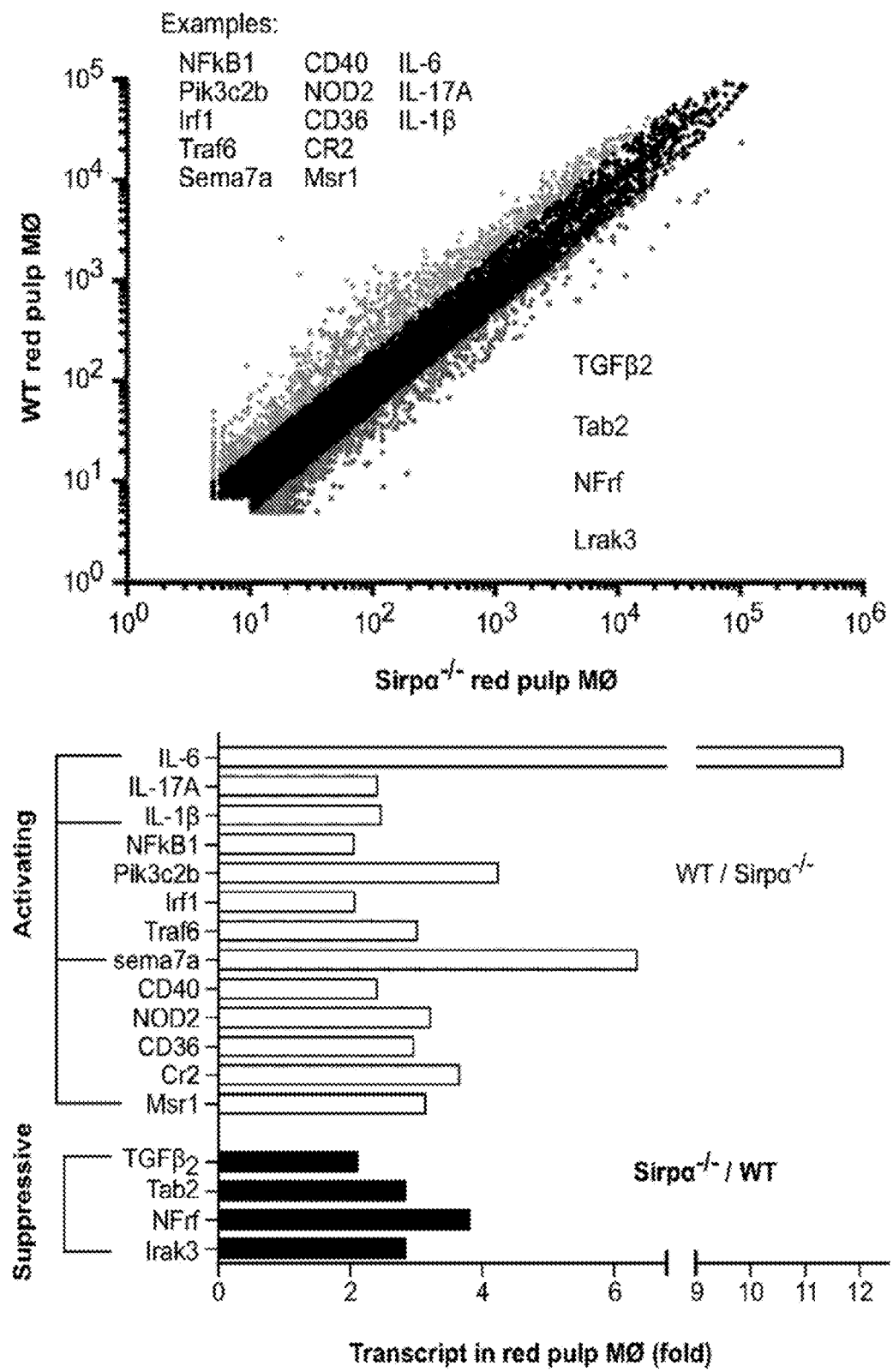
Figure 7G:
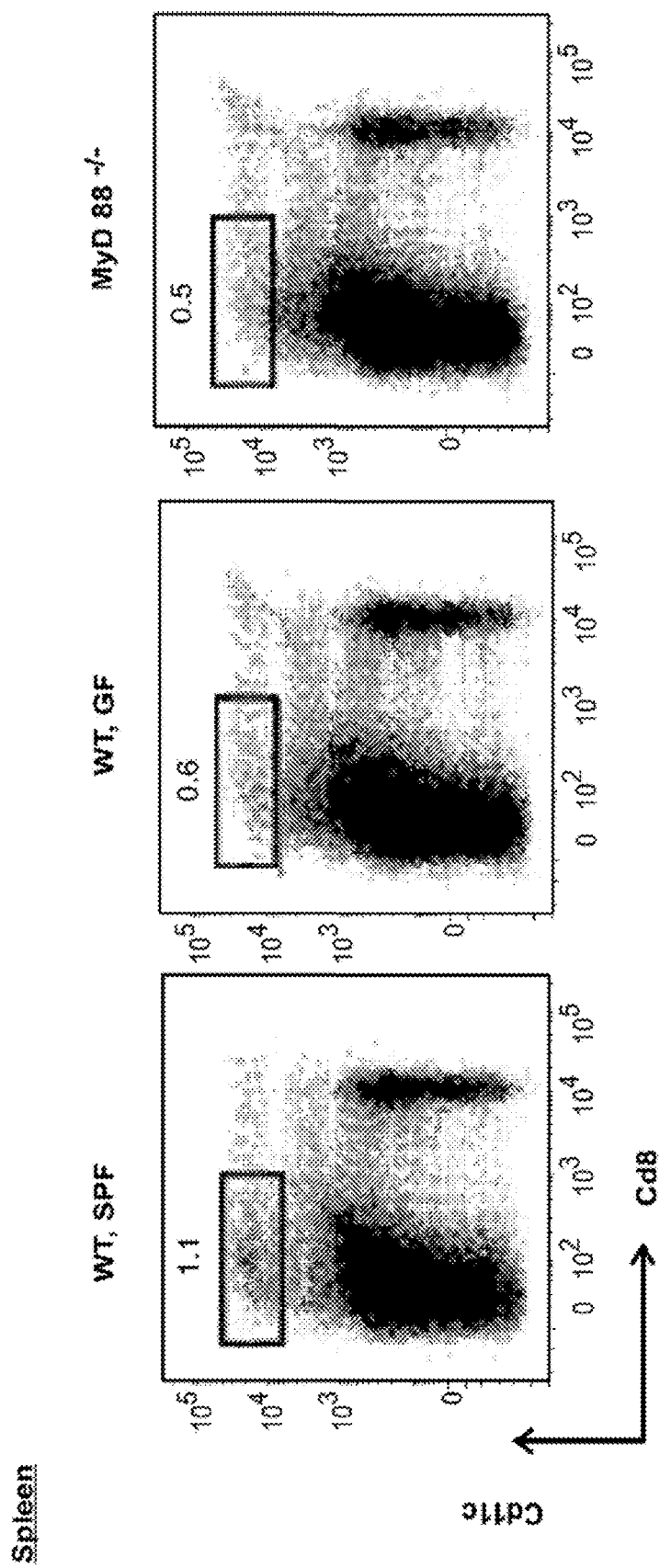
Figure 7H:
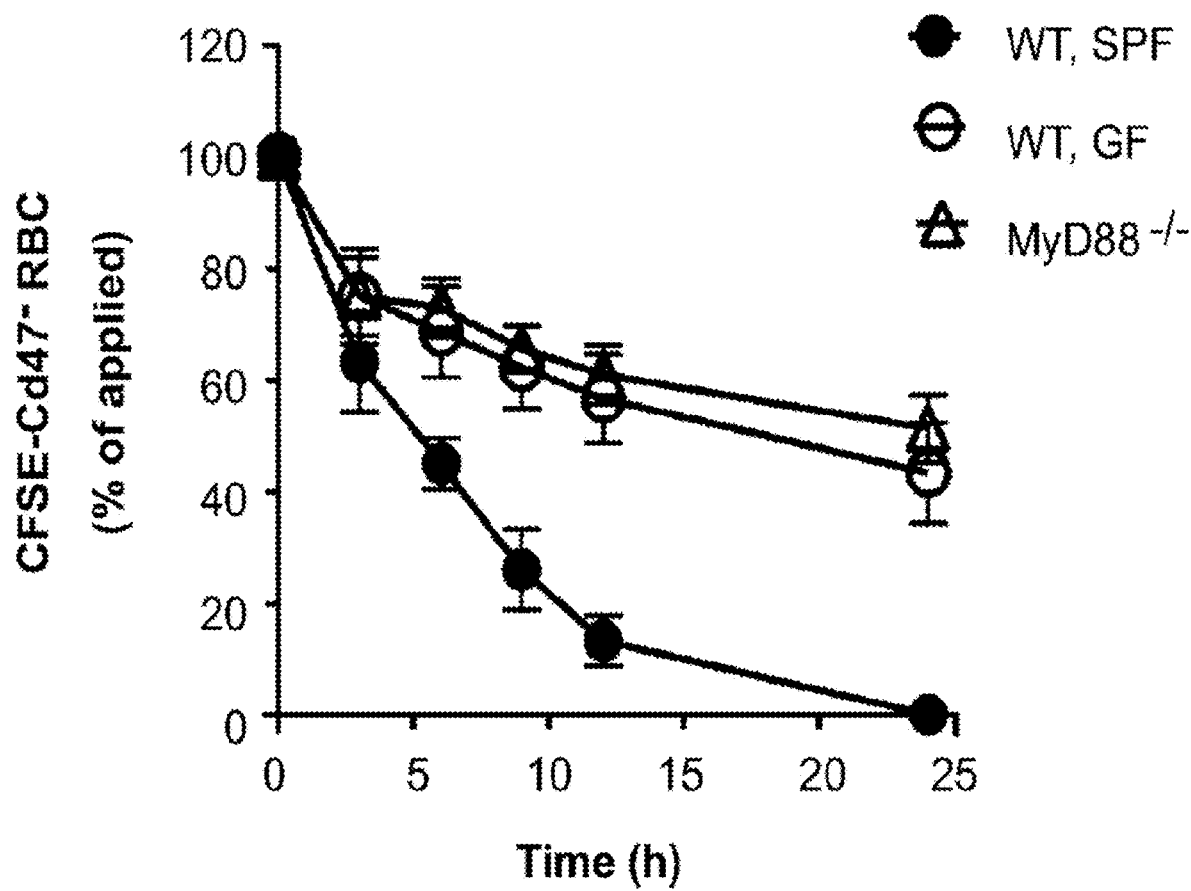

Upon further analysis of spleen cells, we found that those from SIRPα$^{-/-}$ and CD47$^{-/-}$ mice produce relatively higher levels of IL-10, but lower levels of IL-17 and IL-6, compared with spleen cells from WT mice (FIG. 7D). Mutant mouse spleens were also associated with a deficit of CD11c$^+$ dendritic cells (DCs), especially the major migratory and antigen-presenting CD8$^-$ DCs and CD4$^+$ Th lymphocytes (FIG. 7E and previous reports (Saito et al., Blood 116 (18):3517-3525, 2010; Van et al., EMBO J 25 (23):5560-5568, 2006)). Other leukocytes, including natural killer (NK) cells, NKT cells, CD8 T cells, B cells, and the total CD11b$^+$ myeloid cells demonstrated no reduction. Interestingly, red pulp macrophages are even increased in SIRPα$^{-/-}$ and CD47$^{-/-}$ mice (data not shown). Therefore, it is possible that the deficiency of CD11c$^+$CD8$^-$ DCs and CD4$^+$ Th cells and the increase of IL-10 collectively causes inactivity of erythrophagocytosis in the spleens of SIRPα$^{-/-}$ and CD47$^{-/-}$ mice. Transcription profiles revealed that red pulp macrophages in SIRPα$^{-/-}$ mice, compared with those in WT mice, express reduced levels of functional-stimulating molecules, such as IL-6, IL-17, IL-1β, NF-κB, and Cd40, but higher levels of suppressive molecules such as TGFβ (FIG. 7F). In another experiment, we examined mice that were housed under a germ-free (GF) condition and mice deficient of MyD88 (MyD88$^{-/-}$), both being associated with a reduction of CD11c$^+$CD8$^-$ DCs and CDd4$^+$ Th cells in the spleen as well (FIG. 7G) (Walton et al., Immunol. Lett. 102 (1):16-24, 2006; Silver et al., Eur. J. Immunol. 37 (10):2734-2743, 2007; Hammer et al., Annu. Rev. Immunol. 31 (1):743-791, 2013; Sadanaga et al., Arthritis Rheum 56 (5):1618-1628, 2007). These mice manifested attenuated clearance of CD47$^-$ RBCs in RBC adoptive transfer experiments (FIG. 7H).

Discussion: The present study reveals that multilayered mechanisms govern macrophage phagocytic behavior toward healthy self-cells. In addition to the previously identified CD47-SIRPα-mediated mechanism that prevents phagocytosis, there are additional mechanisms that determine the propensity of macrophages to either phagocytose, or be restrained from phagocytosing, the surrounding self-cells. Indeed, CD47-SIRPα-mediated inhibition is relevant and indispensable only when the phagocytosis toward "self" is initiated in a tissue environment. Remarkably, multiple inflammatory conditions and proinflammatory cytokines/factors (e.g., LPS, IL-1β, IL-6, IL-17, and TNFα) activate macrophages for phagocytosis toward healthy self-cells. Conversely, IL-10 suppresses this phagocytosis.

Different behavior of macrophages in WT mice vs. in SIRPα$^{-/-}$ or CD47$^{-/-}$ mice has long been observed. As shown in our studies and as shown previously (Oldenborg et al., Science 288 (5473):2051-2054, 2000), WT mice rapidly eliminate CD47$^-$ RBC through erythrophagocytosis, whereas SIRPα$^{-/-}$ or CD47$^{-/-}$ mice cannot. We found that the lack of phagocytic stimulation is attributed to the latent macrophage behavior in mutant mice, as inflammatory stimulations that activate the PKC-Syk pathway instantly elicit phagocytosis. In particular, these mutant mice, although generally manifesting no macrophage-mediated destruction, have developed acute anemia under inflammatory conditions due to splenic macrophages directly phagocytizing self-RBCs. Ex vivo treatments of macrophages isolated from these mice with LPS or cytokines, or transfer of the nonphagocytic SIRPα$^{-/-}$ macrophages into WT mice, have instantly induced erythrophagocytosis. However, in these experiments, we failed to observe macrophages displaying tolerance or the "split tolerance" suggested previously by others (Wang et al., Proc. Natl. Acad. Sci. USA 104 (34):13744-13749, 2007). Instead, phagocytically activated macrophages derived from mice without CD47 or SIRPα expression displayed the same, direct phagocytosis toward RBCs, splenocytes, and other cells as macrophages from WT mice, providing an absence of CD47-SIRPα inhibition. Another similarity of macrophages from SIRPα$^{-/-}$, or CD47$^{-/-}$, mice and WT mice is that they all need phagocytic activation to acquire an ability to directly phagocytose healthy self-cells. As shown by our data, not only macrophages from mutant mice but also PEM and BMDM from WT mice displayed phagocytic inactivity toward even CD47-null RBCs in the absence of stimulation. WT red pulp macrophages, although displaying direct phagocytosis toward CD47-null RBC in vivo, were unable to maintain this aggressiveness shortly after isolation. It is as if the "not attack-self" is a default mode for all macrophages, whereas "attack-self" represents an exceptional, hyper-phagocytic status for which special activating mechanisms are needed. This idea that macrophages are generally set to not attack self-cells is consistent with the fact that, in most non-lymphoid tissues, suppressive cytokines IL-10 and TGFβ tend to dominate (e.g., in peritoneum) and repress phagocytosis toward self. The spleen red pulp appears to be an exceptional tissue, constantly providing stimuli sustaining the phagocytic capacity toward self. Lack of such a stimulating environment in the spleen becomes a "compensation" mechanism that maintains SIRPα$^{-/-}$ or CD47$^{-/-}$ mice to be healthy despite the absence of CD47-SIRPα-mediated inhibition.

Although the CD47-SIRPα mechanism may be dispensable under normal conditions, it becomes extremely important under inflammatory conditions and infection, during which host macrophages would gain phagocytosis toward healthy self-cells (as suggested by this study). The finding that SIRPα-/- and CD47$^{-/-}$ mice rapidly develop anemia under inflammatory challenges suggests that lack of these proteins may significantly reduce the threshold for anemia under inflammatory conditions. Inflammation-associated anemia (also called "anemia of inflammation" or "anemia of chronic disease") is among the most frequent complications observed in hospitalized patients. Reported previously by us and others (Zhu et al., *J. Allergy Clin. Immunol.* 132 (2): 426-436, 2013; Kong et al., *J. Exp. Med.* 204 (11): 2719-2731, 2007), SIRPα expression in macrophages is decreased following LPS stimulation, suggesting a dynamic nature for the CD47-SIRPα-mediated inhibition especially on infection or activation of TLR. The expression of CD47 on cells can also be changed under different conditions. Also, as reported by us, alteration of clustering structures of SIRPα on macrophages or CD47 on tissue cells affects phagocytosis (Lv et al., *J. Immunol.* 195 (2):661-671, 2015; Ha et al., *PLoS One* 8 (10):e77615, 2013). Moreover, data presented in this study show that CD47-SIRPα-mediated inhibition controls not only the phagocytic target selection, but also the phagocytic robustness once the target has been chosen. As shown in this study, SIRPα$^-$ macrophages, compared with SIRPα$^+$ macrophages, are much more potent in phagocytosis toward self-cells once they have been activated by LPS or cytokines. Although both mutant strains are deficient of CD47-SIRPα inhibition, more severe anemia ensued in SIRPα$^{-/-}$ animals than in CD47$^{-/-}$ mice after their splenic macrophages were stimulated. Even without stimulation, the macrophages in SIRPα$^{-/-}$ mice clear RBCs faster than those in WT or CD47$^{-/-}$ mice. All these results suggest a SIRPα-ITIM-mediated inhibition on general cell processes of macrophage phagocytosis and are in concurrence with reports showing that the CD47-SIRPα pathway also tempers Fc- and complement-mediated phagocytosis (Okazawa et al., *J. Immunol.* 174 (4):2004-2011, 2005; Oldenborg et al., *Blood* 99 (10): 3500-3504, 2002; Oldenborg et al., *J. Exp. Med.* 193 (7):855-862, 2001), as well as phagocytosis toward apoptotic cells (Lv et al., *J. Immunol.* 195 (2):661-671, 2015). The detailed mechanism by which macrophages directly phagocytize healthy self-cells is unknown, despite that the mechanism that inhibits this phagocytosis via the CD47-SIRPα-SHP axis has been studied. Different from traditional phagocytosis aiming at alien pathogens, immune complexes, debris, and dying self-cells, on which certain eat-me or non-self signals ensure phagocytosis, phagocytosis toward healthy self-cells is uncustomary. To date, the molecules serving as the phagocytic ligands on healthy self-cells, together with the phagocytic receptor on macrophages, remain undefined. From the present study, it can be predicted that the specific phagocytic receptor on macrophages is either unexpressed or expressed but inactive until stimulation-induced activation occurs. The rapid elicitation of phagocytosis by PMA (<30 min) suggests the latter and that the PKC-Syk-mediated signaling pathway likely activates this phagocytic receptor through an "inside-out" mechanism. Along this line, it is possible that the CD47-SIRPα-mediated SHP activity inhibits this phagocytic receptor through protein dephosphorylation that counters the effect by Syk. The study has ruled out CRT-activated LRP1 and other known phagocytic receptors for mediating phagocytosis toward healthy self-cells. In particular, our data show that the CRT-LRP system controls phagocytosis toward apoptotic, but not healthy, self-cells. Interestingly, antibody inhibition of CD11b/CD18 impedes activated macrophage phagocytosis toward self.

Figure 8A:
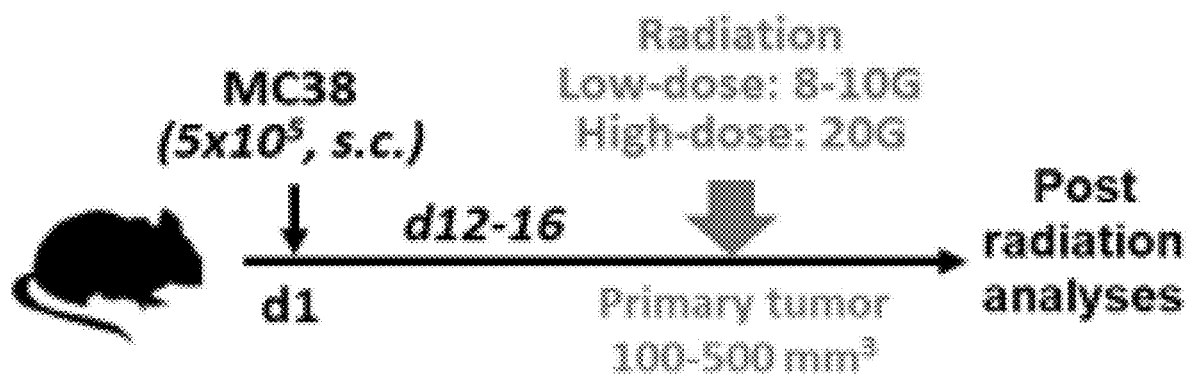
FIGS. 8A-8B include data showing SIRPα$^{-/-}$ mice eradicate MC38 carcinoma with low-dose radiation. 5×105 MC38 carcinoma cells were engrafted (s.c.) the right flank of WT and SIRPα$^{-/-}$ mice. After tumor reaching the size of 100-500 mm3, local tumor irradiation with low-dose X-ray of 8-10 Gy or 20 Gy was given.
Figure 8B:
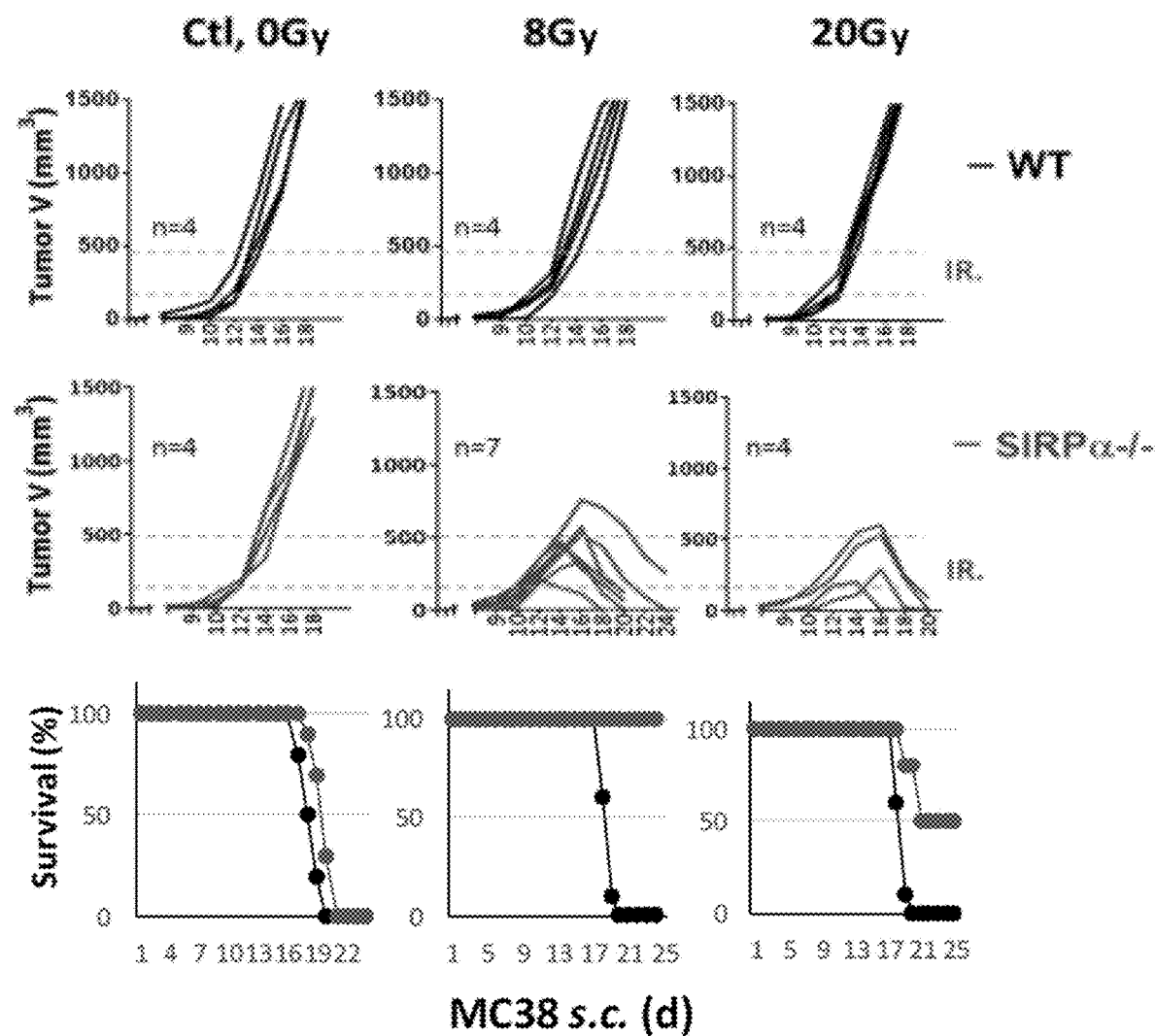

Example 9: SIRPα$^{-/-}$ Mice but not WT Mice Eradicate MC38 Colonic Carcinoma Following Low-Dose Radiation We tested tumor eradication in the second murine model, subcutaneous MC38 colonic carcinoma. As shown in FIG. 8, subcutaneous MC38 carcinoma was established by engrafting MC38 cells (5×10$^5$) into the right flank of WT and SIRPα-/- mice. Primary tumors were observed in both mice after 10 days with no significant differences in their growth rates, and both mice had tumors reach sizes of 100-500 mm$^3$ in 12-16 days. X-ray irradiation of tumors was performed at doses of 8 Gy or 20 Gy. As shown in the figure, these radiation dosages had no noticeable effects in WT mice, in which MC38 tumors continued growing and rapidly progressed beyond the endpoint (>1500 mm$^3$). In contrast, SIRPα$^{-/-}$ mice displayed drastic responses to irradiation, which led to rapid tumor reduction and eventually complete eradication of tumors in a few days (4-7 days). In particular, SIRPα-/- mice that received 8 Gy all survived after clearing the tumor and maintained a tumor-free condition thereafter. SIRPα$^{-/-}$ mice that received 20 Gy, though having exhibited rapid eradication of their tumors, developed severe adverse reactions suggestive of acute, sepsis-like inflammation, resulting in 50% mortality post-radiation.

Figure 9:
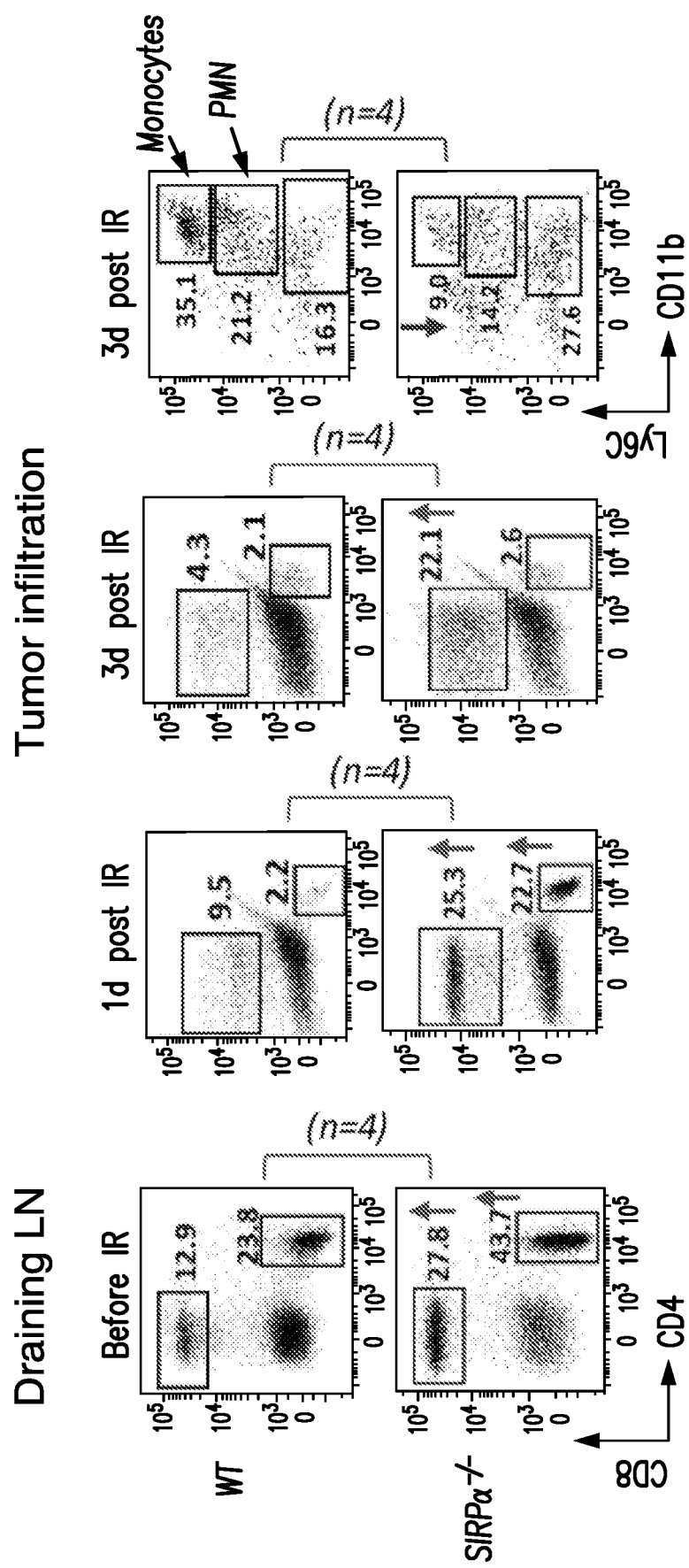
FIG. 9 includes data showing elimination of MC38 carcinoma in SIRPα-/- mice is associated with increased tumor-sensitive CD4 Th and CD8 CTL populations in the tumor-draining lymph nodes and intratumoral tissues right after tumor irradiation, and reduced monocyte infiltration into tumors.

Since studies by others have suggested that T cell-mediated anti-cancer immunity, especially the cytotoxicity of CD8 T cells, plays a critical role in the radiation-induced anti-cancer effect, we analyzed T cells before and after M38 tumor irradiation. As shown in FIG. 9, we found SIRPα$^{-/-}$ mice, as compared to WT mice, had significantly larger CD4 and CD8 T cell populations in tumor-draining lymph nodes (inguinal nodes) before X-ray radiation, and markedly increased T cell infiltration into tumors following radiation (24 h), suggesting that SIRPα$^{-/-}$ mice mounted a markedly greater, robust anti-tumor response. In addition, the increased population of CD8 T cells in SIRPα$^{-/-}$ mice remained in the tumor tissues for three additional days, suggestive of continued anti-tumor cytotoxicity and/or enhanced longevity. Interestingly, we observed that SIRPα$^{-/-}$ mice had less monocyte infiltration into the primary tumor following radiotherapy, suggesting a weaker wound-healing response that otherwise would support tumor recovery.

Similar to SIRPα$^{-/-}$ mice that eliminated B16 melanoma following IL-17A treatment, we found that radiation-induced MC38 eradication in SIRPα$^{-/-}$ mice also produced protective anti-MC38 immunity with IgG antibodies in the serum. This immunity was therapeutically effective, demonstrating abscopal effects and resistance to future engraftments of MC38 carcinoma.

Figure 10A:
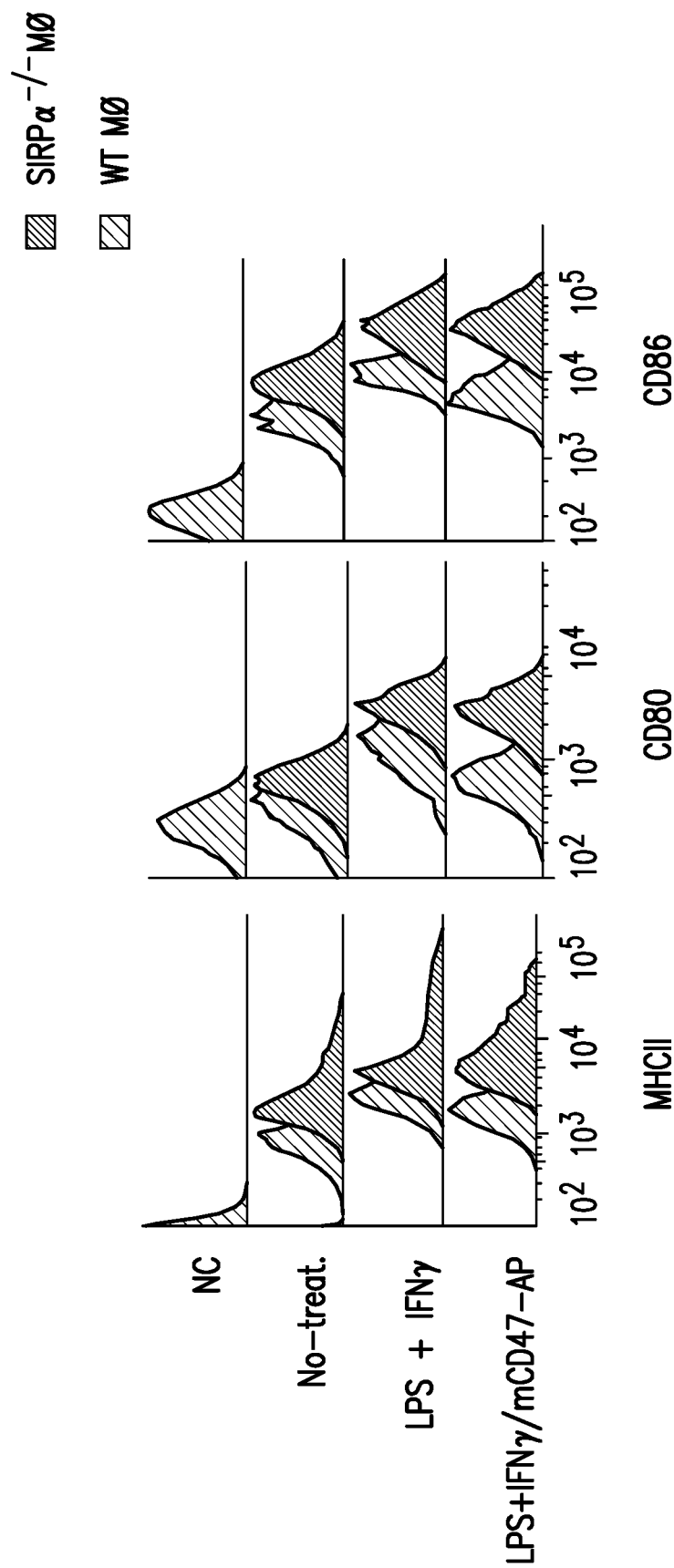
FIGS. 10A-10B includes data showing SIRPα signaling negatively regulates antigen-presentation through suppressing cell surface expressing MHCII, B7-family co-stimulatory molecules CD80 and CD86, and Th1/pro-immunity cytokines induced by LPS+IFNγ, whereas SIRPα depletion promotes expression of antigen-presentation molecules and cytokines.
Figure 10B:
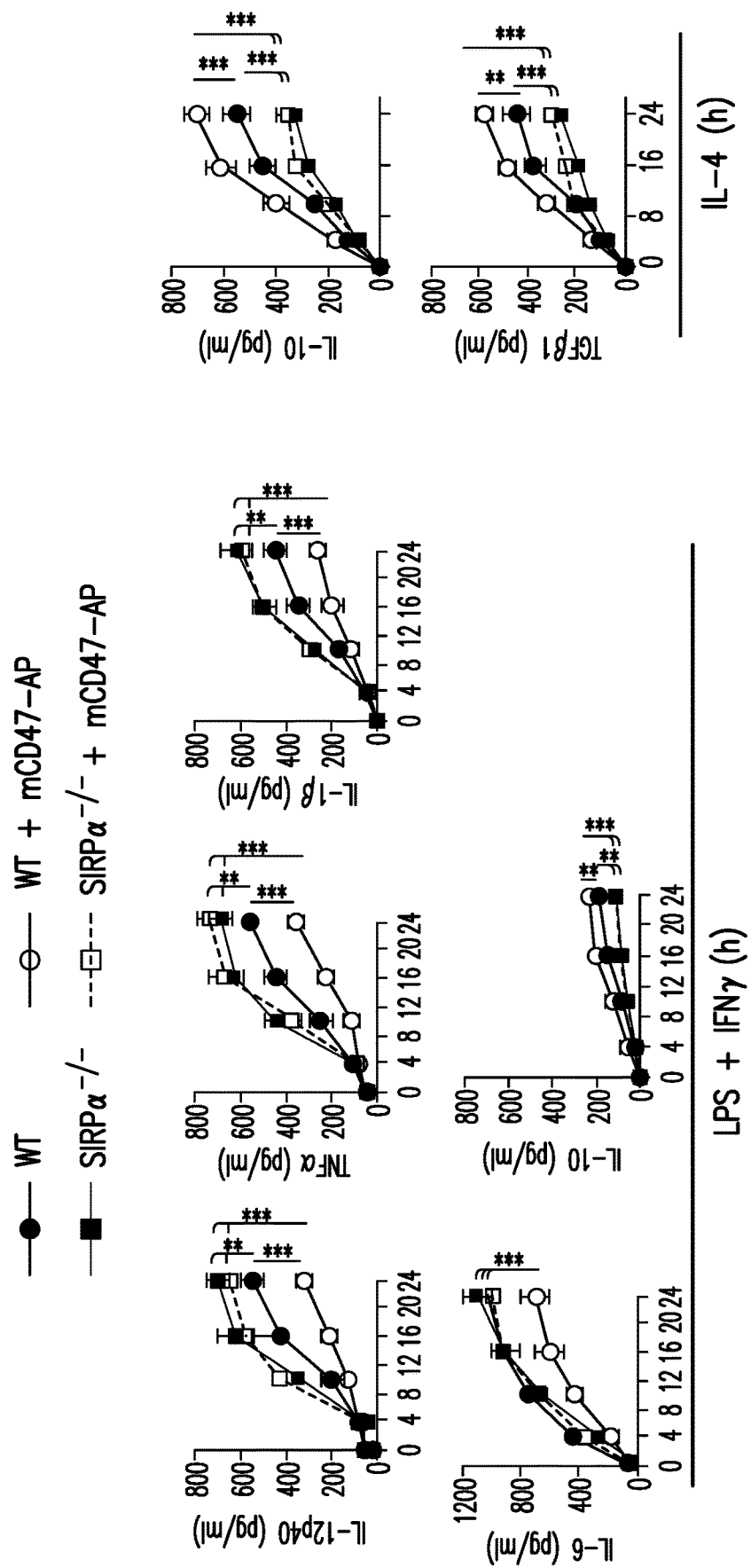

Example 10: SIRPα$^{-/-}$ Phagocytes Display Biased Activation Toward the Antigen Presentation Phenotype We found that SIRPα signaling negatively regulates the capacity of phagocytes to conduct antigen presentation, whereas SIRPα depletion prominently promotes the antigen presentation phenotype. As shown in FIG. 10, treating SIRPα-/- macrophages with LPS+IFNγ, both of which activate phagocytes for antigen presentation, induced higher levels of cell surface MHCII expression and positive costimulatory molecules B7-1/CD80 and B7-2/CD86 than the similarly treated WT macrophages, especially when SIRPα signaling in the latter was triggered by CD47 ligation. Note: mCD47-AP is a soluble murine CD47 extracellular domain fusion protein that directly binds to the SIRPα extracellular domain. Treatment with LPS+IFNγ, or with other factors, also induced higher levels of Th1/pro-immunity cytokines such as IL-12 and TNFα, but lower levels of tolerance-related cytokines such as IL-10 and TGFβ in SIRPα$^{-/-}$ macrophages than in WT macrophages. Together, these results suggest that CD47-SIRPα signaling suppresses antigen presentation that would otherwise induce immunity, whereas SIRPα deficiency promotes the potential to mount a non-tolerogenic adaptive immune response by increasing antigen presentation-associated cytokines and surface expression of costimulatory molecules.

It is to be understood that the foregoing description is intended to illustrate and not to limit the scope of the invention, which is defined by the scope of the appended claims.

---

What is claimed is:

1. A method of generating macrophages with enhanced cancer phagocytosis, the method comprising:
   (a) providing a biological sample from a subject, wherein the biological sample comprises macrophages;
   (b) exposing the sample to an effective amount of a first composition comprising at least 100 units/ml IFNγ to suppress the expression or activity of signal regulatory protein α (SIRPα); and
   (c) exposing the sample from step (b) to an effective amount of a second composition that activates Protein kinase C (PKC)-Spleen tyrosine kinase (Syk) pathway, thereby generating macrophages with enhanced cancer phagocytosis.

2. The method of claim 1, wherein the biological sample further comprises cancer cells.

3. The method of claim 1, wherein the biological sample further comprises dendritic cells.

4. The method of claim 1, wherein the biological sample has been enriched for myeloid cells.

5. The method of claim 1, wherein the first composition further comprises a Toll-like receptor (TLR) ligand.

6. The method of claim 5, wherein the TLR ligand comprises a CpG oligonucleotide or a polyinosinic:polycytidylic acid (poly I:C).

7. The method of claim 5, wherein the TLR ligand comprises GARDIQUIMOD or IMIQUIMOD.

8. The method of claim 1, wherein the first composition further comprises, IL-6.

9. The method of claim 1, wherein the first composition comprises a Toll-like receptor (TLR) ligand, IFNγ, and IL-6.

10. The method of claim 1, wherein the second composition comprises phorbol 12-myristate 13-acetate (PMA).

11. The method of claim 1, further comprising administering the macrophages with enhanced cancer phagocytosis to a subject.

* * * * *

SEQUENCE LISTING

<160> NUMBER OF SEQ ID NOS: 12

<210> SEQ ID NO 1
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1
caaagugcuu acagugcagg uag          23

<210> SEQ ID NO 2
<211> LENGTH: 23
<212> TYPE: RNA
<213> ORGANISM: Artificial Sequence
<220> FEATURE:
<223> OTHER INFORMATION: Synthetic Construct

<400> SEQUENCE: 2
uaaagugcuu auagugcagg uag          23

<210> SEQ ID NO 3
<211> LENGTH: 23
<212> TYPE: RNA
<213> ORGANISM: Artificial Sequence
<220> FEATURE:
<223> OTHER INFORMATION: Synthetic Construct

<400> SEQUENCE: 3
aaaagugcuu acagugcagg uag          23

<210> SEQ ID NO 4
<211> LENGTH: 23
<212> TYPE: RNA
<213> ORGANISM: Artificial Sequence
<220> FEATURE:
<223> OTHER INFORMATION: Synthetic Construct

<400> SEQUENCE: 4
cuaccugcac uguaagcacu uug          23

<210> SEQ ID NO 5
<211> LENGTH: 23

```
<212> TYPE: RNA
<213> ORGANISM: Artificial Sequence
<220> FEATURE:
<223> OTHER INFORMATION: Synthetic Construct

<400> SEQUENCE: 5
cuaccugcac uauaagcacu uua                                                  23

<210> SEQ ID NO 6
<211> LENGTH: 23
<212> TYPE: RNA
<213> ORGANISM: Artificial Sequence
<220> FEATURE:
<223> OTHER INFORMATION: Synthetic Construct

<400> SEQUENCE: 6
cuaccugcac uguaagcacu uuu                                                  23

<210> SEQ ID NO 7
<211> LENGTH: 24
<212> TYPE: DNA
<213> ORGANISM: Artificial Sequence
<220> FEATURE:
<223> OTHER INFORMATION: Synthetic Construct

<400> SEQUENCE: 7
ctgaaggtga ctcagcctga gaaa                                                 24

<210> SEQ ID NO 8
<211> LENGTH: 24
<212> TYPE: DNA
<213> ORGANISM: Artificial Sequence
<220> FEATURE:
<223> OTHER INFORMATION: Synthetic Construct

<400> SEQUENCE: 8
actgatacgg atggaaaagt ccat                                                 24

<210> SEQ ID NO 9
<211> LENGTH: 24
<212> TYPE: DNA
<213> ORGANISM: Artificial Sequence
<220> FEATURE:
<223> OTHER INFORMATION: Synthetic Construct

<400> SEQUENCE: 9
ttgccggtgg gacccattag gtgg                                                 24

<210> SEQ ID NO 10
<211> LENGTH: 24
<212> TYPE: DNA
<213> ORGANISM: Artificial Sequence
<220> FEATURE:
<223> OTHER INFORMATION: Synthetic Construct

<400> SEQUENCE: 10
agattgtatt tctgtgtcag gctc                                                 24

<210> SEQ ID NO 11
<211> LENGTH: 20
<212> TYPE: DNA
<213> ORGANISM: Artificial Sequence
<220> FEATURE:
<223> OTHER INFORMATION: Synthetic Construct

<400> SEQUENCE: 11
```

```
tgtgctcgac gttgtcactg                                            20

<210> SEQ ID NO 12
<211> LENGTH: 24
<212> TYPE: DNA
<213> ORGANISM: Artificial Sequence
<220> FEATURE:
<223> OTHER INFORMATION: Synthetic Construct

<400> SEQUENCE: 12
cgataccgta aagcacgagg aagc                                       24
```